(12) United States Patent
McElroy et al.

(10) Patent No.: US 8,138,209 B2
(45) Date of Patent: Mar. 20, 2012

(54) SUBSTITUTED PICOLINAMIDES AS MAO-B INHIBITORS USEFUL FOR TREATING OBESITY

(75) Inventors: John Francis McElroy, Wilmington, DE (US); Robert J. Chorvat, West Chester, PA (US); Rajagopalan Parthasarathi, Chennai (IN)

(73) Assignee: Jenrin Discovery, Inc., West Chester, PA (US)

( * ) Notice: Subject to any disclaimer, the term of this patent is extended or adjusted under 35 U.S.C. 154(b) by 1551 days.

(21) Appl. No.: 11/456,912

(22) Filed: Jul. 12, 2006

(65) Prior Publication Data

US 2007/0015734 A1   Jan. 18, 2007

Related U.S. Application Data

(60) Provisional application No. 60/698,867, filed on Jul. 13, 2005.

(51) Int. Cl.
*A61K 31/44* (2006.01)
(52) U.S. Cl. ........................................ 514/354; 546/323
(58) Field of Classification Search .................. 514/354; 546/323
See application file for complete search history.

(56) References Cited

U.S. PATENT DOCUMENTS

| | | | |
|---|---|---|---|
| 4,764,522 A | | 8/1988 | Imhof et al. |
| 5,238,962 A | | 8/1993 | Da Prada et al. |
| 5,360,808 A | | 11/1994 | Englert et al. |
| 5,380,861 A | | 1/1995 | Scalone et al. |
| 5,534,635 A | | 7/1996 | Scalone et al. |
| 6,762,320 B2 | | 7/2004 | Jolidon et al. |
| 6,900,354 B2 | | 5/2005 | Jolidon et al. |
| 6,951,884 B2 | | 10/2005 | Jolidon et al. |
| 2002/0019421 A1* | | 2/2002 | Biberman ..................... 514/343 |
| 2007/0078172 A1* | | 4/2007 | McElroy et al. ............. 514/355 |

FOREIGN PATENT DOCUMENTS

| | | |
|---|---|---|
| DE | 632257 C1 | 7/1936 |
| GB | 862721 A | 3/1961 |
| WO | 03/037847 A1 | 5/2003 |

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: WILEY-VCH Verlag GmbH & Co. KGaA, 2005, Preface.*
Visentin, Virgile et al.; Alteration of Amine Oxidase Activity in the Adipose Tissue of Obese Subjects; Obesity Research vol. 12 No. 3 Mar. 2004; 547-555.
Visentin, Virgile et al.; Inhibition of Rat Fat Cell Lipolysis by Monoamine Oxidase and Semicarbazide-Sensitive Amine Oxidase Substrates; European Journal of Pharmacology 466 (2003) 235-243.
Demolis, A et al., Local Anesthetic Properties of o-Alkoxybenzoic Acid Alkylaminoalkylamides, Arzneimittel-Forschung 1960, 10, 743-745 (only HCAPLUS abstract provided).

* cited by examiner

*Primary Examiner* — James O. Wilson
*Assistant Examiner* — Douglas M Willis
(74) *Attorney, Agent, or Firm* — Vance Intellectual Property, PC

(57) ABSTRACT

The invention provides novel compounds of formula I:

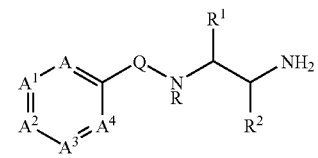

that are monoamine oxidase-B inhibitors, which can be useful in treating obesity, diabetes, and/or cardiometabolic disorders (e.g., hypertension, dyslipidemias, high blood pressure, and insulin resistance).

20 Claims, No Drawings

SUBSTITUTED PICOLINAMIDES AS MAO-B INHIBITORS USEFUL FOR TREATING OBESITY

CROSS-REFERENCE TO RELATED APPLICATIONS

This application claims the priority benefit of U.S. Provisional Application No. 60/698,867 filed Jul. 13, 2005, now pending, which is incorporated herein by reference.

FIELD OF THE INVENTION

The present invention provides compounds and pharmaceutical compositions thereof and methods of using the same for treating obesity, diabetes, and/or cardiometabolic disorders (e.g., hypertension, dyslipidemias, high blood pressure, and insulin resistance).

BACKGROUND OF THE INVENTION

Lazabemide is a monoamine oxidase (MAO) inhibitor that was developed for the treatment of neurological disorders such as Parkinson's disease and dementia. MAO is an enzyme responsible for metabolizing biogenic monoamines including serotonin, dopamine, histamine, and phenylethylamine. By inhibiting MAO located in the central nervous system (CNS), MAO inhibitors and their analogues increase the concentration of monoamines present within the brain synapses. This enhances monoamine-mediated neurotransmission, effectively treating neurological disorders such as Parkinson's disease and depression.

MAO enzymes are also located in a number of peripheral (non-CNS) tissues, including adipocytes; the cells that comprise body fat. The function of MAO enzymes in adipocytes has not been established. Currently, the only approved clinical use of L-selegiline and other MAO inhibitors is for the treatment of neurological disorders such as Parkinson's disease and depression.

Obesity is associated with an increase in the overall amount of adipose tissue (i.e., body fat), especially adipose tissue localized in the abdominal area. Obesity has reached epidemic proportions in the United States. The prevalence of obesity has steadily increased over the years among all racial and ethnic groups. According to the United States Surgeon General, 61% of the adult population and 14% of children are obese or overweight. Forty four million Americans are obese, with an additional eighty million deemed medically overweight. Obesity is responsible for more than 300,000 deaths annually, and will soon overtake tobacco usage as the primary cause of preventable death in the United States. Obesity is a chronic disease that contributes directly to numerous dangerous co-morbidities, including type 2 diabetes, cardiovascular disease, inflammatory diseases, premature aging, and some forms of cancer. Type 2 diabetes, a serious and life-threatening disorder with growing prevalence in both adult and childhood populations, is currently the $7^{th}$ leading cause of death in the United States. Since more than 80% of patients with type 2 diabetes are overweight, obesity is the greatest risk factor for developing type 2 diabetes. Increasing clinical evidence indicates that the best way to control type 2 diabetes is to reduce weight.

The most popular over-the counter drugs for the treatment of obesity, phenylpropanolamine and ephedrine, and the most popular prescription drug, fenfluramine, were removed from the marketplace as a result of safety concerns. Drugs currently approved for the long-term treatment of obesity fall into two categories: (a) CNS appetite suppressants such as sibutramine and (b) gut lipase inhibitors such as orlistat. CNS appetite suppressants reduce eating behavior through activation of the 'satiety center' in the brain and/or by inhibition of the 'hunger center' in the brain. Gut lipase inhibitors reduce the absorption of dietary fat from the gastrointestinal (GI) tract. Although sibutramine and orlistat work through very different mechanisms, they share in common the same overall goal of reducing body weight secondary to reducing the amount of calories that reach the systemic circulation. Unfortunately, these indirect therapies produce only a modest initial weight loss (approximately 5% compared to placebo) that is usually not maintained. After one or two years of treatment, most patients return to or exceed their starting weight. In addition, most approved anti-obesity therapeutics produce undesirable and often dangerous side effects that can complicate treatment and interfere with a patient's quality of life.

The lack of therapeutic effectiveness, coupled with the spiraling obesity epidemic, positions the 'treatment of obesity' as one of the largest and most urgent unmet medical needs. There is, therefore, a real and continuing need for the development of improved medications that treat obesity.

MAO-B inhibitors such as lazabemide have been clinically useful in the treatment of CNS disorders. They have now unexpectedly been discovered to also have anti-obesity activity. Even more surprising is that the anti-obesity activity effects of MAO-B inhibitors are mediated via a peripheral (i.e., non-CNS) mechanism. This new discovery provides a novel approach for the treatment of obesity. Moreover, if the CNS effects of these compounds can be reduced, their peripherally mediated anti-obesity properties should provide therapeutic agents with greater safety. It has, as a result, become highly desirable to find MAO-B inhibitors with limited or no CNS effects. Compounds of this sort are expected to be useful in treating obesity and the variety of co-morbidities to which it contributes.

SUMMARY OF THE INVENTION

Accordingly, in an aspect, the present invention provides novel MAO-B inhibitors or stereoisomers or pharmaceutically acceptable salts that are useful to treat obesity, diabetes, and/or cardiometabolic disorders (e.g., hypertension, dyslipidemias, high blood pressure, and insulin resistance).

In another aspect, the present invention provides novel pharmaceutical compositions, comprising: a pharmaceutically acceptable carrier and a therapeutically effective amount of at least one of the compounds of the present invention or a stereoisomer or pharmaceutically acceptable salt thereof.

In another aspect, the present invention provides novel methods for treating obesity, diabetes, and/or cardiometabolic disorders (e.g., hypertension, dyslipidemias, high blood pressure, and insulin resistance), comprising: administering to a patient in need thereof a therapeutically effective amount of at least one of the compounds of the present invention or a stereoisomer or pharmaceutically acceptable salt thereof.

In another aspect, the present invention provides novel methods for treating CNS disorders, comprising: administering to a patient in need thereof a therapeutically effective amount of at least one of the compounds of the present invention or a stereoisomer or pharmaceutically acceptable salt thereof.

In another aspect, the present invention provides processes for preparing novel compounds.

In another aspect, the present invention provides novel compounds or stereoisomers or pharmaceutically acceptable salts for use in therapy.

In another aspect, the present invention provides the use of novel compounds for the manufacture of a medicament for the treatment of obesity, diabetes, and/or cardiometabolic disorders.

In another aspect, the present invention provides the use of novel compounds for the manufacture of a medicament for the treatment of CNS disorders.

These and other aspects, which will become apparent during the following detailed description, have been achieved by the inventors' discovery that the presently claimed compounds or stereoisomers or pharmaceutically acceptable salts thereof are expected to be effective MAO-B inhibitors.

DETAILED DESCRIPTION OF THE INVENTION

The present invention is based on the unexpected finding that an MAO-B inhibitor is capable of reducing the amount of adipose tissue (i.e., body fat) in a warm-blooded mammal. This finding was unexpected because body fat can be reduced despite little, if any, concomitant reduction in food intake.

In an embodiment, the present invention provides novel compound AA or a stereoisomer or pharmaceutically acceptable salt thereof:

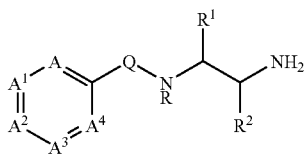

AA wherein: Q is C=O or $SO_2$; A, $A^1$, $A^2$, $A^3$, and $A^4$ are selected from $CA^5$, $N^+$—$O^-$, or N; and $A^5$ (independently at each occurrence), R, $R^1$, and $R^2$ are all independently selected from H and a group capable of reducing or limiting the CNS activity of compound A; and, provided that at least one of the A groups is other than H, halogen, nitro, $NH_2$, OH, $OC_{1-6}$ alkyl, $C_{1-6}$ alkyl, phenyl, and benzyloxy.

[1] In another embodiment, the present invention provides a novel compound of formula I, or a stereoisomer or a pharmaceutically acceptable salt thereof:

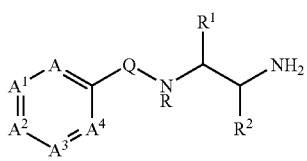

I wherein:

A, $A^1$, $A^2$, $A^3$, and $A^4$, are independently selected from CH, CX, CY, N, and $N^+$—$O^-$, provided that from 0-1 is $N^+$—$O^-$;

R, at each occurrence, is independently selected from H and $C_{1-6}$ alkyl;

$R^1$ is selected from H and $C_{1-6}$ alkyl;

$R^2$ is selected from H and $C_{1-6}$ alkyl;

Q is selected from C=O and $SO_2$;

X is selected from H, $OR^3$, $NR^3Z$, OZ, SZ, $SO_2OR^3$, $SO_2NR^3R^4$, $CO_2R^3$, $CONR^3R^4$, $PO(OR^3)_2$, $(CH_2)_m$-tetrazole, $O(CH_2)_n$-tetrazole, $(CH_2)_mCO_2R$, $(CH_2)_mCONR_2$, $(CH_2)_mCN$, NR—$C_{2-4}$ alkenyl, $NRSO_2CH_3$, $NR(CH_2)_nCO_2R$, $NR(CH_2)_n$-tetrazole, $CH_2$-aryl, $O(CH_2)_n$-biphenyl, $O(CH_2)_n$-biphenyl-$(CH_2)_mCO_2R$, $O(CH_2)_n$-biphenyl-$(CH_2)_m$tetrazole, $O(CH_2)_n$-biphenyl-$(CH_2)_mCN$, $O(CH_2)_n$-biphenyl-$(CH_2)_mCON(R)_2$, $NR(CH_2)_n$-biphenyl-$(CH_2)_mCO_2R$, $NR(CH_2)_n$-biphenyl-$(CH_2)_m$tetrazole, $NR(CH_2)_n$-biphenyl-$(CH_2)_mCN$, $NR(CH_2)_n$-biphenyl, $NR(CH_2)_n$-biphenyl-$(CH_2)_mCON(R)_2$, $O(CH_2)_n$-aryl, $O(CH_2)_n$-heteroaryl, $NR(CH_2)_n$-aryl, $NR(CH_2)_n$-heteroaryl, $O(CH_2)_n$-aryl$(CH_2)_mCO_2R$, $O(CH_2)_n$-aryl-$C_{2-6}$ alkenyl-$CO_2R$, $O(CH_2)_n$-aryl$(CH_2)_m$-tetrazole, $O(CH_2)_n$-aryl$(CH_2)_mCN$, $O(CH_2)_n$-aryl$(CH_2)_mCON(R)_2O(CH_2)_n$-aryl$(CH_2)_m$—$PO(OR)_2$, $O(CH_2)_n$-aryl-$O(CH_2)_nCO_2R$, $O(CH_2)_n$-aryl-$O$—$C_{2-6}$ alkenyl-$CO_2R$, $O(CH_2)_n$-arylO$(CH_2)_n$-tetrazole, $O(CH_2)_n$-arylO$(CH_2)_nCN$, $O(CH_2)_n$-arylO$(CH_2)_nCON(R)_2$, $O(CH_2)_n$-arylO$(CH_2)_n$—$PO(OR)_2$, $O(CH_2)_n$-aryl-NR$(CH_2)_nCO_2R$, $O(CH_2)_n$-aryl-NR$C_{2-6}$ alkenyl-$CO_2R$, $O(CH_2)_n$-aryl-NR$(CH_2)_n$-tetrazole, $O(CH_2)_n$-aryl-NR$(CH_2)_nCN$, $O(CH_2)_n$-aryl-NR$(CH_2)_nCON(R)_2$, $O(CH_2)_n$-aryl-NR$(CH_2)_n$—$PO(OR)_2$, $NR(CH_2)_n$-aryl$(CH_2)_mCO_2R$, $NR(CH_2)_n$-aryl-$C_{2-6}$ alkenyl-$CO_2R$, $NR(CH_2)_n$-aryl$(CH_2)_m$-tetrazole, $NR(CH_2)_n$-aryl$(CH_2)_mCN$, $NR(CH_2)_n$-aryl$(CH_2)_mCON(R)_2$, $NR(CH_2)_n$-aryl$(CH_2)_m$—$PO(OR)_2$, $NR(CH_2)_n$-aryl-NR$(CH_2)_nCO_2R$, $NR(CH_2)_n$-aryl-NR—$C_{2-6}$ alkenyl-$CO_2R$, $NR(CH_2)_n$-aryl-NR$(CH_2)_n$-tetrazole, $NR(CH_2)_n$-aryl-NR$(CH_2)_nCN$, $NR(CH_2)_n$-aryl-NR$(CH_2)_nCON(R)_2$, $NR(CH_2)_n$-aryl-NR$(CH_2)_nPO(OR)_2$, $NR(CH_2)_n$-arylO$(CH_2)_nCO_2R$, $NR(CH_2)_n$-aryl-O—$C_{2-6}$ alkenyl-$CO_2R$, $NR(CH_2)_n$-aryl-O$(CH_2)_n$-tetrazole, $NR(CH_2)_n$-arylO$(CH_2)_nCN$, $NR(CH_2)_n$-aryl-O$(CH_2)_nCON(R)_2$, $NR(CH_2)_n$-arylO$(CH_2)_nPO(OR)_2$, $O(CH_2)_n$-heteroaryl$(CH_2)_mCO_2R$, $O(CH_2)_n$-heteroaryl-$C_{2-6}$ alkenyl-$CO_2R$, $O(CH_2)_n$-heteroaryl$(CH_2)_m$-tetrazole, $O(CH_2)_n$-heteroaryl-$(CH_2)_mCN$, $O(CH_2)_n$-heteroaryl$(CH_2)_mCON(R)_2$, $O(CH_2)_n$-heteroaryl$(CH_2)_m$—$PO(OR)_2$, $O(CH_2)_n$-heteroaryl-O$(CH_2)_nCO_2R$, $O(CH_2)_n$-heteroaryl-O—$C_{2-6}$ alkenyl-$CO_2R$, $O(CH_2)_n$-heteroarylO$(CH_2)_n$-tetrazole, $O(CH_2)_n$-heteroarylO $(CH_2)_nCN$, $O(CH_2)_n$-heteroarylO$(CH_2)_nCON(R)_2$, $O(CH_2)_n$-heteroarylO$(CH_2)_n$—$PO(OR)_2$, $O(CH_2)_n$-heteroaryl-NR$(CH_2)_nCO_2R$, $O(CH_2)_n$-heteroaryl-NR—$C_{2-6}$ alkenyl-$CO_2R$, $O(CH_2)_n$-heteroaryl-NR$(CH_2)_n$-tetrazole, $O(CH_2)_n$-heteroaryl-NR$(CH_2)_nCN$, $O(CH_2)_n$-heteroaryl-NR$(CH_2)_nCON(R)_2$, $O(CH_2)_n$-heteroaryl-NR$(CH_2)_n$—$PO(OR)_2$, $NR(CH_2)_n$-heteroaryl$(CH_2)_mCO_2R$, $NR(CH_2)_n$-heteroaryl-$C_{2-6}$ alkenyl-$CO_2R$, $NR(CH_2)_n$-heteroaryl, $NR(CH_2)_n$-heteroaryl$(CH_2)_m$-tetrazole, $NR(CH_2)_n$-heteroaryl$(CH_2)_mCN$, $NR(CH_2)_n$-heteroaryl$(CH_2)_mCON(R)_2$, $NR(CH_2)_n$-heteroaryl$(CH_2)_m$—$PO(OR)_2$, $NR(CH_2)_n$-heteroaryl-NR$(CH_2)_nCO_2R$, $NR(CH_2)_n$-heteroaryl-NR—$C_{2-6}$ alkenyl-$CO_2R$, $NR(CH_2)_n$-heteroaryl-NR$(CH_2)_n$-tetrazole, $NR(CH_2)_n$ heteroaryl-NR$(CH_2)_nCN$, $NR(CH_2)_n$-heteroaryl-NR$(CH_2)_nCON(R)_2$, $NR(CH_2)_n$-heteroaryl-NR$(CH_2)_nPO(OR)_2$, $NR(CH_2)_n$-heteroaryl-O$(CH_2)_nCO_2R$, $NR(CH_2)_n$-heteroaryl-O—$C_{2-6}$ alkenyl-$CO_2R$, $NR(CH_2)_n$-heteroaryl-O$(CH_2)_n$-tetrazole, $NR(CH_2)_n$-heteroaryl-O$(CH_2)_nCN$, $NR(CH_2)_n$-heteroaryl-O$(CH_2)_nCON(R)_2$, $NR(CH_2)_n$-heteroarylO$(CH_2)_nPO(OR)_2$, and $O(CH_2CH_2O)_pCH_2CH_2OR^3$, where heteroaryl is a 5-12 membered ring system consisting of carbon atoms and from 1-4 heteroatoms selected from N, O, and S, and wherein aryl, heteroaryl, and biphenyl are substituted with 1-2 $X^2$ and tetrazole is substituted with 0-1 R;

$X^2$, at each occurrence, is independently selected from H, OR, $C_{1-4}$ alkyl, $C_{1-4}$ alkyloxy, fluoro-$C_{1-4}$ alkyloxy, $C_{2-4}$ alkenyl, $C_{2-4}$ alkynyl, halogen, $CF_3$, nitro, —CN, $CON(R)_2$, and $SO_2N(R)C_{1-4}$alkyl;

Y is selected from H, $OR^3$, $NR^3Z$, OZ, SZ, $SO_2OR^3$, $SO_2NR^3R^4$, $CO_2R^3$, $CONR^3R^4$, $PO(OR^3)_2$, $(CH_2)_m$-tetrazole, $O(CH_2)_n$-tetrazole, $C_{1-4}$ alkyl, halogen, $CF_3$, nitro, —CN, $CON(R)_2$, $SO_2N(R)C_{1-4}$alkyl and $NHSO_2R$;

provided that when Q is C=O and A, $A^1$, $A^2$, $A^3$, and $A^4$ are other than $N^+$—$O^-$ then at least one of X and Y is present and is other than H or $OR^3$;

Z, at each occurrence, is independently selected from H, $C_{1-6}$ alkyl, $(CH_2)_nCO_2R^3$, $CH_2CH$=$CHCO_2R^3$, $(CH_2)_nCN$, $(CH_2)_nCONR^3R^4$, $CH_2CH$=CHCN, $CH_2CH$=CHCON$(R^3)_2$, $(CH_2)_nPO(OR^3)_2$, $(CH_2)_nSO_3R^3$, $(CH_2)_nN(R^3)_2$, and $(CH_2)_nN^+(R^3)_3G^-$;

$G^-$ is a counterion;

$R^3$, at each occurrence, is independently selected from H, $C_{1-6}$ alkyl, $C_{2-6}$ alkenyl, and aryl-$C_{1-16}$ alkyl-;

$R^4$, at each occurrence, is independently selected from H, $C_{1-6}$ alkyl, phenyl, and $CH(L)CO_2R^3$;

L is selected from H, $C_{1-6}$ alkyl, —$(CH_2)_m$-phenyl, —$(CH_2)_n$—O—$C_{1-6}$ alkyl, and —$(CH_2)_n$—S—$C_{1-6}$ alkyl;

m, at each occurrence, is independently selected from 0, 1, 2, 3, and 4;

n, at each occurrence, is independently selected from 1, 2, 3, and 4; and, p is selected from 1, 2, 3, 4, 5, 6, 7, 8, 9, 10, and 11.

In another embodiment, the compounds of the present invention have from 0-1 acid functionalities.

[2] In another embodiment, the present invention provides a novel compound of formula Ia, or a stereoisomer or a pharmaceutically acceptable salt thereof:

Ia wherein:

A, $A^1$, and $A^3$, are independently selected from CH, CX, CY, N, and $N^+$—$O^-$, provided that from 0-1 is $N^+$—$O^-$;

R, at each occurrence, is independently selected from H and $C_{1-4}$ alkyl;

$R^1$ is selected from H and $C_{1-4}$ alkyl;

$R^2$ is selected from H and $C_{1-4}$ alkyl;

X is selected from H, $OR^3$, $NR^3Z$, OZ, SZ, $SO_2NR^3R^4$, $CONR^3R^4$, $NHSO_2R$, $(CH_2)_nCONR_2$, $(CH_2)_nCN$, NR—$C_{2-4}$ alkenyl, $NRSO_2CH_3$, $CH_2$-aryl, $O(CH_2)_n$-biphenyl, $O(CH_2)_n$-biphenyl-$(CH_2)_mCN$, $O(CH_2)_n$-biphenyl-$(CH_2)_mCON(R)_2$, $NR(CH_2)_n$-biphenyl, $NR(CH_2)_n$-biphenyl-$(CH_2)_mCN$, $NR(CH_2)_n$-biphenyl-$(CH_2)_mCON(R)_2$, O$(CH_2)_n$-aryl, $O(CH_2)_n$-heteroaryl, $NR(CH_2)_n$-aryl, $NR(CH_2)_n$-heteroaryl, $O(CH_2)_n$-aryl$(CH_2)_mCN$, $O(CH_2)_n$-aryl$(CH_2)_mCON(R)_2$, $O(CH_2)_n$-arylO$(CH_2)_nCN$, $O(CH_2)_n$-arylO$(CH_2)_nCON(R)_2$, $O(CH_2)_n$-aryl-$NR(CH_2)_nCN$, $O(CH_2)_n$-aryl-$NR(CH_2)_nCON(R)_2$, $NR(CH_2)_n$-aryl$(CH_2)_mCN$, $NR(CH_2)_n$-aryl$(CH_2)_mCON(R)_2$, $NR(CH_2)_n$-aryl-$NR(CH_2)_nCN$, $NR(CH_2)_n$-aryl-$NR(CH_2)_nCON(R)_2$, $NR(CH_2)_n$-arylO$(CH_2)_nCN$, $NR(CH_2)_n$-aryl-O$(CH_2)_nCON(R)_2$, $O(CH_2)_n$-heteroaryl-$(CH_2)_mCN$, $O(CH_2)_n$-heteroaryl$(CH_2)_mCON(R)_2$, $O(CH_2)_n$-heteroaryl O$(CH_2)_nCN$, $O(CH_2)_n$-heteroarylO$(CH_2)_nCON(R)_2$, $O(CH_2)_n$-heteroaryl-$NR(CH_2)_nCN$, $O(CH_2)_n$-heteroaryl-NR$(CH_2)_nCON(R)_2$, $NR(CH_2)_n$-heteroaryl$(CH_2)_mCN$, $NR(CH_2)_n$-heteroaryl$(CH_2)_mCON(R)_2$, $NR(CH_2)_n$-heteroaryl-$NR(CH_2)_nCN$, $NR(CH_2)_n$-heteroaryl-$NR(CH_2)_nCON(R)_2$, $NR(CH_2)_n$-heteroaryl-$O(CH_2)_nCN$, $NR(CH_2)_n$-heteroaryl-$O(CH_2)_nCON(R)_2$, and $O(CH_2CH_2O)_pCH_2CH_2OR^3$, where heteroaryl is a 5-12 membered ring system consisting of carbon atoms and from 1-4 heteroatoms selected from N, O, and S, and wherein aryl, heteroaryl, and biphenyl are substituted with 1-2 $X^2$;

provided that the heteroaryl in X is other than tetrazole;

$X^2$, at each occurrence, is independently selected from H, OR, $C_{1-4}$ alkyl, $C_{2-4}$ alkenyl, $C_{2-4}$ alkynyl, halogen, $CF_3$, nitro, —CN, $CON(R)_2$, and $SO_2N(R)C_{1-4}$alkyl;

Y is selected from $SO_2OR^3$, $CO_2R^3$, $PO(OR^3)_2$, $(CH_2)_m$-tetrazole, $O(CH_2)_n$-tetrazole, $SO_2N(R)C_{1-4}$alkyl, and $NHSO_2R$;

Z is selected from H, $C_{1-4}$ alkyl, $(CH_2)_nCONR^3R^4$, $CH_2CH$=$CHCON(R^3)_2$, $(CH_2)_nN(R^3)_2$, and $(CH_2)_nN^+(R^3)_3G^-$;

$G^-$ is selected from $Cl^-$ and $Br^-$;

$R^3$, at each occurrence, is independently selected from H, $C_{1-4}$ alkyl, $C_{2-4}$ alkenyl, and benzyl;

$R^4$, at each occurrence, is independently selected from H, $C_{1-4}$ alkyl, phenyl, and $CH(L)CO_2R^3$; and, L is selected from H, $CH_3$, $CH_2CH_3$, $CH(CH_3)_2$, $CH_2CH(CH_3)_2$, $CH(CH_3)CH_2CH_3$, $CH_2CH_2SCH_3$, phenyl, and benzyl.

[2a] In another embodiment, the present invention provides a novel compound of formula $Ia_1$, or a stereoisomer or a pharmaceutically acceptable salt thereof:

$Ia_1$ wherein:

Y is selected from $OR^3$ and $O(CH_2)_nCO_2R^3$; and,

Z is selected from $(CH_2)_nCO_2R^3$, $CH_2CH$=$CHCO_2R^3$, $CH_2$=$CHCON(R^3)_2$, $(CH_2)_nCONR^3R^4$, $(CH_2)_nPO(OR^3)_2$, and $(CH_2)_nSO_3R^3$.

[3] In another embodiment, the present invention provides a novel compound of formula Ia, or a stereoisomer or a pharmaceutically acceptable salt thereof:

Ia wherein:

A, $A^1$, and $A^3$, are independently selected from CH, CX, CY, N, and $N^+$—$O^-$, provided that from 0-1 is $N^+$—$O^-$;

R, at each occurrence, is independently selected from H and $C_{1-4}$ alkyl;

$R^1$ is selected from H and $C_{1-4}$ alkyl;

$R^2$ is selected from H and $C_{1-4}$ alkyl;

X is selected from $SO_2OR^3$, $PO(OR^3)_2$, $(CH_2)_m$-tetrazole, $O(CH_2)_n$-tetrazole, $(CH_2)_nCO_2R$, $NR(CH_2)_nCO_2R$, $NR(CH_2)_n$-tetrazole, $O(CH_2)_n$-biphenyl-$(CH_2)_mCO_2R$, O(CH$_2$)$_n$-biphenyl-(CH$_2$)$_m$tetrazole, NR(CH$_2$)$_n$-biphenyl-(CH$_2$)$_m$CO$_2$R, NR(CH$_2$)$_n$-biphenyl-(CH$_2$)$_m$tetrazole, O(CH$_2$)$_n$-aryl(CH$_2$)$_m$CO$_2$R, O(CH$_2$)$_n$-aryl-C$_{2-6}$ alkenyl-CO$_2$R, O(CH$_2$)$_n$-aryl(CH$_2$)$_m$-tetrazole, O(CH$_2$)$_n$-aryl(CH$_2$)$_m$—PO(OR)$_2$, O(CH$_2$)$_n$-aryl-O(CH$_2$)$_n$CO$_2$R, O(CH$_2$)$_n$-aryl-O—C$_{2-6}$ alkenyl-CO$_2$R, O(CH$_2$)$_n$-arylO(CH$_2$)$_n$-tetrazole, O(CH$_2$)$_n$-arylO(CH$_2$)$_n$—PO(OR)$_2$, O(CH$_2$)$_n$-aryl-NR(CH$_2$)$_n$CO$_2$R, O(CH$_2$)$_n$-aryl-NRC$_{2-6}$ alkenyl-CO$_2$R, O(CH$_2$)$_n$-aryl-NR(CH$_2$)$_n$-tetrazole, O(CH$_2$)$_n$-aryl-NR(CH$_2$)$_n$—PO(OR)$_2$, NR(CH$_2$)$_n$-aryl(CH$_2$)$_m$CO$_2$R, NR(CH$_2$)$_n$-aryl-C$_{2-6}$ alkenyl-CO$_2$R, NR(CH$_2$)$_n$-aryl(CH$_2$)$_m$-tetrazole, NR(CH$_2$)$_n$-aryl(CH$_2$)$_m$—PO(OR)$_2$, NR(CH$_2$)$_n$-aryl-NR(CH$_2$)$_n$CO$_2$R, NR(CH$_2$)$_n$-aryl-NR—C$_{2-6}$ alkenyl-CO$_2$R, NR(CH$_2$)$_n$-aryl-NR(CH$_2$)$_n$-tetrazole, NR(CH$_2$)$_n$-aryl-NR(CH$_2$)$_n$PO(OR)$_2$, NR(CH$_2$)$_n$-arylO(CH$_2$)$_n$CO$_2$R, NR(CH$_2$)$_n$-aryl-O—C$_{2-6}$ alkenyl-CO$_2$R, NR(CH$_2$)$_n$-aryl-O(CH$_2$)$_n$-tetrazole, NR(CH$_2$)$_n$-arylO(CH$_2$)$_n$PO(OR)$_2$, O(CH$_2$)$_n$-heteroaryl(CH$_2$)$_m$CO$_2$R, O(CH$_2$)$_n$-heteroaryl-C$_{2-6}$ alkenyl-CO$_2$R, O(CH$_2$)$_n$-heteroaryl(CH$_2$)$_m$-tetrazole, O(CH$_2$)$_n$-heteroaryl(CH$_2$)$_m$—PO(OR)$_2$, O(CH$_2$)$_n$-heteroaryl-O(CH$_2$)$_n$CO$_2$R, O(CH$_2$)$_n$-heteroaryl-O—C$_{2-6}$ alkenyl-CO$_2$R, O(CH$_2$)$_n$-heteroarylO(CH$_2$)$_n$-tetrazole, O(CH$_2$)$_n$-heteroarylO(CH$_2$)$_n$—PO(OR)$_2$, O(CH$_2$)$_n$-heteroaryl-NR(CH$_2$)$_n$CO$_2$R, O(CH$_2$)$_n$-heteroaryl-NR—C$_{2-6}$ alkenyl-CO$_2$R, O(CH$_2$)$_n$-heteroaryl-NR(CH$_2$)$_n$-tetrazole, O(CH$_2$)$_n$-heteroaryl-NR(CH$_2$)$_n$—PO(OR)$_2$, NR(CH$_2$)$_n$-heteroaryl(CH$_2$)$_m$CO$_2$R, NR(CH$_2$)$_n$-heteroaryl-C$_{2-6}$ alkenyl-CO$_2$R, NR(CH$_2$)$_n$-heteroaryl(CH$_2$)$_m$-tetrazole, NR(CH$_2$)$_n$-heteroaryl(CH$_2$)$_m$—PO(OR)$_2$, NR(CH$_2$)$_n$-heteroaryl-NR(CH$_2$)$_n$CO$_2$R, NR(CH$_2$)$_n$-heteroaryl-NR—C$_{2-6}$ alkenyl-CO$_2$R, NR(CH$_2$)$_n$-heteroaryl-NR(CH$_2$)$_n$-tetrazole, NR(CH$_2$)$_n$-heteroaryl-NR(CH$_2$)$_n$PO(OR)$_2$, NR(CH$_2$)$_n$-heteroaryl-O(CH$_2$)$_n$CO$_2$R, NR(CH$_2$)$_n$-heteroaryl-O—C$_{2-6}$ alkenyl-CO$_2$R, NR(CH$_2$)$_n$-heteroaryl-O(CH$_2$)$_n$-tetrazole, NR(CH$_2$)$_n$-heteroarylO(CH$_2$)$_n$PO(OR)$_2$, and O(CH$_2$CH$_2$O)$_p$CH$_2$CH$_2$OR$^3$, where heteroaryl is a 5-12 membered ring system consisting of carbon atoms and from 1-4 heteroatoms selected from N, O, and S, and wherein aryl, heteroaryl, and biphenyl are substituted with 1-2 X$^2$ and tetrazole is substituted with 0-1 R;

X$^2$, at each occurrence, is independently selected from H, OR, C$_{1-4}$ alkyl, C$_{2-4}$ alkenyl, C$_{2-4}$ alkynyl, halogen, CF$_3$, nitro, —CN, CON(R)$_2$, and SO$_2$N(R)C$_{1-4}$alkyl;

Y is selected from H, OR$^3$, NR$^3$Z, OZ, SZ, SO$_2$NR$^3$R$^4$, CONR$^3$R$^4$, C$_{1-4}$ alkyl, halogen, CF$_3$, nitro, —CN, CON(R)$_2$, SO$_2$N(R)C$_{1-4}$alkyl, and NHSO$_2$R;

provided that when A, A$^1$, and A$^3$ are other than N$^+$—O$^−$, then at least one of X and Y is present and is other than H or OR$^3$;

Z is selected from H, C$_{1-4}$ alkyl, (CH$_2$)$_n$CONR$^3$R$^4$, CH$_2$CH=CHCON(R$^3$)$_2$, (CH$_2$)$_n$N(R$^3$)$_2$, and (CH$_2$)$_n$N$^+$(R$^3$)$_3$G$^−$;

G$^−$ is selected from Cl$^−$ and Br$^−$;

R$^3$, at each occurrence, is independently selected from H, C$_{1-4}$ alkyl, C$_{2-4}$ alkenyl, and benzyl;

R$^4$, at each occurrence, is independently selected from H, C$_{1-4}$ alkyl, phenyl, and CH(L)CO$_2$R$^3$; and, L is selected from H, CH$_3$, CH$_2$CH$_3$, CH(CH$_3$)$_2$, CH$_2$CH(CH$_3$)$_2$, CH(CH$_3$)CH$_2$CH$_3$, CH$_2$CH$_2$SCH$_3$, phenyl, and benzyl.

[3a] In another embodiment, the present invention provides a novel compound of formula Ia$_1$, or a stereoisomer or a pharmaceutically acceptable salt thereof:

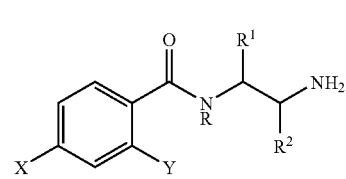

wherein:

Z is selected from (CH$_2$)$_n$CO$_2$R$^3$, CH$_2$CH=CHCO$_2$R$^3$, CH$_2$=CHCON(R$^3$)$_2$, (CH$_2$)$_n$CONR$^3$R$^4$, (CH$_2$)$_n$PO(OR$^3$)$_2$, and (CH$_2$)$_n$SO$_3$R$^3$

[4] In another embodiment, the present invention provides a novel compound of formula Ib, or a stereoisomer or a pharmaceutically acceptable salt thereof:

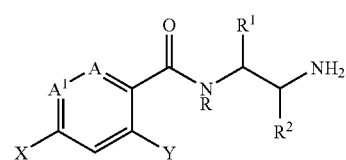

wherein:

A and A$^1$, are independently selected from CH and N;

R, at each occurrence, is independently selected from H and C$_{1-4}$ alkyl;

R$^1$ is selected from H and C$_{1-4}$ alkyl;

R$^2$ is selected from H and C$_{1-4}$ alkyl;

X is selected from H, OR$^3$, NR$^3$Z, OZ, SZ, SO$_2$NR$^3$R$^4$, CONR$^3$R$^4$, NHSO$_2$R, (CH$_2$)$_n$CONR$_2$, (CH$_2$)$_n$CN, NR—C$_{2-4}$ alkenyl, NRSO$_2$CH$_3$, CH$_2$-aryl, O(CH$_2$)$_n$-biphenyl, O(CH$_2$)$_n$-biphenyl-(CH$_2$)$_m$CN, O(CH$_2$)$_n$-biphenyl-(CH$_2$)$_m$CON(R)$_2$, NR(CH$_2$)$_n$-biphenyl, NR(CH$_2$)$_n$-biphenyl-(CH$_2$)$_m$CN, NR(CH$_2$)$_n$-biphenyl-(CH$_2$)$_m$CON(R)$_2$, O(CH$_2$)$_n$-aryl, O(CH$_2$)$_n$-heteroaryl, NR(CH$_2$)$_n$-aryl, NR(CH$_2$)$_n$-heteroaryl, O(CH$_2$)$_n$-aryl(CH$_2$)$_m$CN, O(CH$_2$)$_n$-aryl(CH$_2$)$_m$CON(R)$_2$, O(CH$_2$)$_n$-arylO(CH$_2$)$_n$CN, O(CH$_2$)$_n$-arylO(CH$_2$)$_n$CON(R)$_2$, O(CH$_2$)$_n$-aryl-NR(CH$_2$)$_n$CN, O(CH$_2$)$_n$-aryl-NR(CH$_2$)$_n$CON(R)$_2$, NR(CH$_2$)$_n$-aryl(CH$_2$)$_m$CN, NR(CH$_2$)$_n$-aryl(CH$_2$)$_m$CON(R)$_2$, NR(CH$_2$)$_n$-aryl-NR(CH$_2$)$_n$CN, NR(CH$_2$)$_n$-aryl-NR(CH$_2$)$_n$CON(R)$_2$, NR(CH$_2$)$_n$-arylO(CH$_2$)$_n$CN, NR(CH$_2$)$_n$-aryl-O(CH$_2$)$_n$CON(R)$_2$, O(CH$_2$)$_n$-heteroaryl-(CH$_2$)$_m$CN, O(CH$_2$)$_n$-heteroaryl(CH$_2$)$_m$CON(R)$_2$, O(CH$_2$)$_n$-heteroaryl O(CH$_2$)$_n$CN, O(CH$_2$)$_n$-heteroarylO(CH$_2$)$_n$CON(R)$_2$, O(CH$_2$)$_n$-heteroaryl-NR(CH$_2$)$_n$CN, O(CH$_2$)$_n$-heteroaryl-NR(CH$_2$)$_n$CON(R)$_2$, NR(CH$_2$)$_n$-heteroaryl(CH$_2$)$_m$CN, NR(CH$_2$)$_n$-heteroaryl(CH$_2$)$_m$CON(R)$_2$, NR(CH$_2$)$_n$ heteroaryl-NR(CH$_2$)$_n$CN, NR(CH$_2$)$_n$-heteroaryl-NR(CH$_2$)$_n$CON(R)$_2$, NR(CH$_2$)$_n$-heteroaryl-O(CH$_2$)$_n$CN, NR(CH$_2$)$_n$-heteroaryl-O(CH$_2$)$_n$CON(R)$_2$, and O(CH$_2$CH$_2$O)$_p$CH$_2$CH$_2$OR$^3$, where heteroaryl is a 5-12 membered ring system consisting of carbon atoms and from 1-4 heteroatoms selected from N, O, and S, and wherein aryl, heteroaryl, and biphenyl are substituted with 1-2 X$^2$;

provided that the heteroaryl in X is other than tetrazole;

X$^2$, at each occurrence, is independently selected from H, OR, C$_{1-4}$ alkyl, C$_{2-4}$ alkenyl, C$_{2-4}$ alkynyl, halogen, CF$_3$, nitro, —CN, CON(R)$_2$, and SO$_2$N(R)C$_{1-4}$alkyl;

Y is selected from SO$_2$OR$^3$, CO$_2$R$^3$, PO(OR$^3$)$_2$, (CH$_2$)$_m$-tetrazole, O(CH$_2$)$_n$-tetrazole, SO$_2$N(R)C$_{1-4}$alkyl and NHSO$_2$R;

9

Z is selected from H, $C_{1-4}$ alkyl, $(CH_2)_nCONR^3R^4$, $CH_2CH=CHCON(R^3)_2$, $(CH_2)_nN(R^3)_2$, and $(CH_2)_nN^+(R^3)_3G^-$;

$G^-$ is selected from $Cl^-$ and $Br^-$;

$R^3$, at each occurrence, is independently selected from H, $C_{1-4}$ alkyl, $C_{2-4}$ alkenyl, and benzyl;

$R^4$, at each occurrence, is independently selected from H, $C_{1-4}$ alkyl, phenyl, and $CH(L)CO_2R^3$; and, L is selected from H, $CH_3$, $CH_2CH_3$, $CH(CH_3)_2$, $CH_2CH(CH_3)_2$, $CH(CH_3)CH_2CH_3$, $CH_2CH_2SCH_3$, phenyl, and benzyl.

[5] In another embodiment, the present invention provides a novel compound of formula Ib, or a stereoisomer or a pharmaceutically acceptable salt thereof:

Ib wherein:

A and $A^1$, are independently selected from CH and N;

R, at each occurrence, is independently selected from H and $C_{1-4}$ alkyl;

$R^1$ is selected from H and $C_{1-4}$ alkyl;

$R^2$ is selected from H and $C_{1-4}$ alkyl;

X is selected from $SO_2OR^3$, $PO(OR^3)_2$, $(CH_2)_m$-tetrazole, $O(CH_2)_n$-tetrazole, $(CH_2)_mCO_2R$, $NR(CH_2)_nCO_2R$, $NR(CH_2)$-tetrazole, $O(CH_2)_n$-biphenyl-$(CH_2)_mCO_2R$, $O(CH_2)_n$-biphenyl-$(CH_2)_m$tetrazole, $NR(CH_2)_n$-biphenyl-$(CH_2)_mCO_2R$, $NR(CH_2)_n$-biphenyl-$(CH_2)_m$tetrazole, $O(CH_2)_n$-aryl$(CH_2)_mCO_2R$, $O(CH_2)_n$-aryl-$C_{2-6}$ alkenyl-$CO_2R$, $O(CH_2)_n$-aryl$(CH_2)$ m-tetrazole, $O(CH_2)_n$-aryl$(CH_2)_m$—$PO(OR)_2$, $O(CH_2)_n$-aryl-$O(CH_2)_nCO_2R$, $O(CH_2)_n$-aryl-O—$C_{2-6}$ alkenyl-$CO_2R$, $O(CH_2)_n$-arylO$(CH_2)_n$-tetrazole, $O(CH_2)_n$-arylO$(CH_2)_n$—$PO(OR)_2$, $O(CH_2)_n$-aryl-$NR(CH_2)_nCO_2R$, $O(CH_2)_n$-aryl-$NRC_{2-6}$ alkenyl-$CO_2R$, $O(CH_2)_n$-aryl-$NR(CH_2)_n$-tetrazole, $O(CH_2)_n$-aryl-$NR(CH_2)_n$—$PO(OR)_2$, $NR(CH_2)_n$-aryl$(CH_2)_mCO_2R$, $NR(CH_2)_n$-aryl-$C_{2-6}$ alkenyl-$CO_2R$, $NR(CH_2)_n$-aryl$(CH_2)_m$-tetrazole, $NR(CH_2)_n$-aryl$(CH_2)_m$—$PO(OR)_2$, $NR(CH_2)_n$-aryl-$NR(CH_2)_nCO_2R$, $NR(CH_2)_n$-aryl-NR—$C_{2-6}$ alkenyl-$CO_2R$, $NR(CH_2)_n$-aryl-$NR(CH_2)_n$-tetrazole, $NR(CH_2)_n$-aryl-$NR(CH_2)_nPO(OR)_2$, $NR(CH_2)_n$-arylO$(CH_2)_nCO_2R$, $NR(CH_2)_n$-aryl-O—$C_{2-6}$ alkenyl-$CO_2R$, $NR(CH_2)$-aryl-O$(CH_2)_n$-tetrazole, $NR(CH_2)_n$-arylO$(CH_2)_nPO(OR)_2$, $O(CH_2)_n$-heteroaryl$(CH_2)_mCO_2R$, $O(CH_2)_n$-heteroaryl-$C_{2-6}$ alkenyl-$CO_2R$, $O(CH_2)_n$-heteroaryl$(CH_2)_m$-tetrazole, $O(CH_2)$ n-heteroaryl$(CH_2)_m$—$PO(OR)_2$, $O(CH_2)_n$-heteroaryl-$O(CH_2)_nCO_2R$, $O(CH_2)_n$-heteroaryl-O—$C_{2-6}$ alkenyl-$CO_2R$, $O(CH_2)_n$-heteroarylO$(CH_2)_n$-tetrazole, $O(CH_2)_n$-heteroarylO$(CH_2)_n$—$PO(OR)_2$, $O(CH_2)_n$-heteroaryl-$NR(CH_2)_nCO_2R$, $O(CH_2)_n$-heteroaryl-NR—$C_{2-6}$ alkenyl-$CO_2R$, $O(CH_2)_n$-heteroaryl-$NR(CH_2)_n$-tetrazole, $O(CH_2)_n$-heteroaryl-$NR(CH_2)_n$—$PO(OR)_2$, $NR(CH_2)_n$-heteroaryl$(CH_2)_mCO_2R$, $NR(CH_2)_n$-heteroaryl-$C_{2-6}$ alkenyl-$CO_2R$, $NR(CH_2)_n$-heteroaryl$(CH_2)_m$-tetrazole, $NR(CH_2)_n$-heteroaryl$(CH_2)_m$—$PO(OR)_2$, $NR(CH_2)_n$-heteroaryl-$NR(CH_2)_nCO_2R$, $NR(CH_2)_n$-heteroaryl-NR—$C_{2-6}$ alkenyl-$CO_2R$, $NR(CH_2)_n$-heteroaryl-$NR(CH_2)_n$-tetrazole, $NR(CH_2)_n$-heteroaryl-$NR(CH_2)_nPO(OR)_2$, $NR(CH_2)_n$-heteroaryl-$O(CH_2)_nCO_2R$, $NR(CH_2)_n$-heteroaryl-O—$C_{2-6}$ alkenyl-$CO_2R$, $NR(CH_2)_n$-heteroaryl-$O(CH_2)_n$-tetrazole,

10

$NR(CH_2)_n$-heteroarylO$(CH_2)_nPO(OR)_2$, and $O(CH_2CH_2O)_pCH_2CH_2OR^3$, where heteroaryl is a 5-12 membered ring system consisting of carbon atoms and from 1-4 heteroatoms selected from N, O, and S, and wherein aryl, heteroaryl, and biphenyl are substituted with 1-2 $X^2$ and tetrazole is substituted with 0-1 R;

$X^2$, at each occurrence, is independently selected from H, OR, $C_{1-4}$ alkyl, $C_{2-4}$ alkenyl, $C_{2-4}$ alkynyl, halogen, $CF_3$, nitro, —CN, $CON(R)_2$, and $SO_2N(R)C_{1-4}$alkyl;

Y is selected from H, $OR^3$, $NR^3Z$, OZ, SZ, $SO_2NR^3R^4$, $CONR^3R^4$, $C_{1-4}$ alkyl, halogen, $CF_3$, nitro, —CN, $CON(R)_2$, $SO_2N(R)C_{1-4}$alkyl and $NHSO_2R$;

provided that when A, $A^1$, and $A^3$ are other than $N^+$—$O^-$, then at least one of X and Y is present and is other than H or $OR^3$;

Z is selected from H, $C_{1-4}$ alkyl, $(CH_2)_nCONR^3R^4$, $CH_2CH=CHCON(R^3)_2$, $(CH_2)_nN(R^3)_2$, and $(CH_2)_nN^+(R^3)_3G^-$;

$G^-$ is selected from $Cl^-$ and $Br^-$;

$R^3$, at each occurrence, is independently selected from H, $C_{1-4}$ alkyl, $C_{2-4}$ alkenyl, and benzyl;

$R^4$ at each occurrence, is independently selected from H, $C_{1-4}$ alkyl, phenyl, and $CH(L)CO_2R^3$; and, L is selected from H, $CH_3$, $CH_2CH_3$, $CH(CH_3)_2$, $CH_2CH(CH_3)_2$, $CH(CH_3)CH_2CH_3$, $CH_2CH_2SCH_3$, phenyl, and benzyl.

[6] In another embodiment, the present invention provides a novel compound of formula Ic, or a stereoisomer or a pharmaceutically acceptable salt thereof:

Ic wherein:

A and $A^1$, are independently selected from CH and N;

R, at each occurrence, is independently selected from H and $C_{1-4}$ alkyl;

$R^1$ is selected from H and $C_{1-4}$ alkyl;

$R^2$ is selected from H and $C_{1-4}$ alkyl;

X is selected from H, $OR^3$, $NR^3Z$, OZ, SZ, $SO_2NR^3R^4$, $CONR^3R^4$, $NHSO_2R$, $(CH_2)_nCONR_2$, $(CH_2)_nCN$, NR—$C_{2-4}$ alkenyl, $NRSO_2CH_3$, $CH_2$-aryl, $O(CH_2)_n$-biphenyl, $O(CH_2)_n$-biphenyl-$(CH_2)_mCN$, $O(CH_2)_n$-biphenyl-$(CH_2)_mCON(R)_2$, $NR(CH_2)_n$-biphenyl, $NR(CH_2)_n$-biphenyl-$(CH_2)_mCN$, $NR(CH_2)_n$-biphenyl-$(CH_2)_mCON(R)_2$, $O(CH_2)_n$-aryl, $O(CH_2)_n$-heteroaryl, $NR(CH_2)_n$-aryl, $NR(CH_2)_n$-heteroaryl, $O(CH_2)_n$-aryl$(CH_2)_mCN$, $O(CH_2)_n$-aryl$(CH_2)_mCON(R)_2$, $O(CH_2)_n$-arylO$(CH_2)_nCN$, $O(CH_2)_n$-arylO$(CH_2)_nCON(R)_2$, $O(CH_2)_n$-aryl-$NR(CH_2)_nCN$, $O(CH_2)_n$-aryl-$NR(CH_2)_nCON(R)_2$, $NR(CH_2)_n$-aryl$(CH_2)_mCN$, $NR(CH_2)_n$-aryl$(CH_2)_mCON(R)_2$, $NR(CH_2)_n$-aryl-NR$(CH_2)_nCN$, $NR(CH_2)_n$-aryl-$NR(CH_2)_nCON(R)_2$, $NR(CH_2)_n$-arylO$(CH_2)_nCN$, $NR(CH_2)_n$-aryl-$O(CH_2)_nCON(R)_2$, $O(CH_2)_n$-heteroaryl-$(CH_2)_mCN$, $O(CH_2)_n$-heteroaryl$(CH_2)_mCON(R)_2$, $O(CH_2)_n$-heteroaryl $O(CH_2)_nCN$, $O(CH_2)_n$-heteroarylO$(CH_2)_nCON(R)_2$, $O(CH_2)_n$-heteroaryl-$NR(CH_2)_nCN$, $O(CH_2)_n$-heteroaryl-$NR(CH_2)_nCON(R)_2$, $NR(CH_2)_n$-heteroaryl$(CH_2)_mCN$, $NR(CH_2)_n$-heteroaryl$(CH_2)_mCON(R)_2$, $NR(CH_2)_n$ heteroaryl$NR(CH_2)_nCN$, $NR(CH_2)_n$-heteroaryl-$NR(CH_2)_nCON(R)_2$, $NR(CH_2)_n$-heteroaryl-$O(CH_2)_nCN$, $NR(CH_2)_n$-heteroaryl-$O(CH_2)_nCON$ (R)$_2$, and O(CH$_2$CH$_2$O)$_p$CH$_2$CH$_2$OR$^3$, where heteroaryl is a 5-12 membered ring system consisting of carbon atoms and from 1-4 heteroatoms selected from N, O, and S, and wherein aryl, heteroaryl, and biphenyl are substituted with 1-2 X$^2$;

provided that the heteroaryl in X is other than tetrazole;

X$^2$, at each occurrence, is independently selected from H, OR, C$_{1-4}$ alkyl, C$_{2-4}$ alkenyl, C$_{2-4}$ alkynyl, halogen, CF$_3$, nitro, —CN, CON(R)$_2$, and SO$_2$N(R)C$_{1-4}$alkyl;

Z is selected from H, C$_{1-4}$ alkyl, (CH$_2$)$_n$N(R$^3$)$_2$, and (CH$_2$)$_n$N$^+$(R$^3$)$_3$G$^-$;

G$^-$ is selected from Cl$^-$ and Br$^-$;

R$^3$ at each occurrence, is independently selected from H, C$_{1-4}$ alkyl, and benzyl;

R$^4$ at each occurrence, is independently selected from H, C$_{1-4}$ alkyl, and CH(L)CO$_2$R$^3$; and, L is selected from H, CH$_3$, CH$_2$CH$_3$, CH(CH$_3$)$_2$, CH$_2$CH(CH$_3$)$_2$, CH(CH$_3$)CH$_2$CH$_3$, CH$_2$CH$_2$SCH$_3$, phenyl, and benzyl.

[7] In another embodiment, the present invention provides a novel compound of formula Id, or a stereoisomer or a pharmaceutically acceptable salt thereof:

Id wherein:

A is CH or N;

R, at each occurrence, is independently selected from H and C$_{1-4}$ alkyl;

R$^1$ is selected from H and C$_{1-4}$ alkyl;

R$^2$ is selected from H and C$_{1-4}$ alkyl;

X is selected from H, OR$^3$, NR$^3$Z, OZ, SZ, SO$_2$NR$^3$R$^4$, CONR$^3$R$^4$, NHSO$_2$R, (CH$_2$)$_n$CONR$_2$, (CH$_2$)$_n$CN, NR—C$_{2-4}$ alkenyl, NRSO$_2$CH$_3$, CH$_2$-aryl, O(CH$_2$)$_n$-biphenyl, O(CH$_2$)$_n$-biphenyl-(CH$_2$)$_m$CN, O(CH$_2$)$_n$-biphenyl-(CH$_2$)$_m$CON(R)$_2$, NR(CH$_2$)$_n$-biphenyl, NR(CH$_2$)$_n$-biphenyl-(CH$_2$)$_m$CN, NR(CH$_2$)$_n$-biphenyl-(CH$_2$)$_m$CON(R)$_2$, O(CH$_2$)$_n$-aryl, O(CH$_2$)$_n$-heteroaryl, NR(CH$_2$)$_n$-aryl, NR(CH$_2$)$_n$-heteroaryl, O(CH$_2$)$_n$-aryl(CH$_2$)$_m$CN, O(CH$_2$)$_n$-aryl(CH$_2$)$_m$CON(R)$_2$, O(CH$_2$)$_n$-arylO(CH$_2$)$_n$CN, O(CH$_2$)$_n$-arylO(CH$_2$)$_n$CON(R)$_2$, O(CH$_2$)$_n$-aryl-NR(CH$_2$)$_n$CN, O(CH$_2$)$_n$-aryl-NR(CH$_2$)$_n$CON(R)$_2$, NR(CH$_2$)$_n$-aryl(CH$_2$)$_m$CN, NR(CH$_2$)$_n$-aryl(CH$_2$)$_m$CON(R)$_2$, NR(CH$_2$)$_n$-aryl-NR(CH$_2$)$_n$CN, NR(CH$_2$)$_n$-aryl-NR(CH$_2$)$_n$CON(R)$_2$, NR(CH$_2$)$_n$-arylO(CH$_2$)$_n$CN, NR(CH$_2$)$_n$-aryl-O(CH$_2$)$_n$CON(R)$_2$, O(CH$_2$)$_n$-heteroaryl-(CH$_2$)$_m$CN, O(CH$_2$)$_n$-heteroaryl(CH$_2$)$_m$CON(R)$_2$, O(CH$_2$)$_n$-heteroaryl O(CH$_2$)$_n$CN, O(CH$_2$)$_n$-heteroarylO(CH$_2$)$_n$CON(R)$_2$, O(CH$_2$)$_n$-heteroaryl-NR(CH$_2$)$_n$CN, O(CH$_2$)$_n$-heteroaryl-NR(CH$_2$)$_n$CON(R)$_2$, NR(CH$_2$)$_n$-heteroaryl(CH$_2$)$_m$CN, NR(CH$_2$)$_n$ heteroaryl-NR(CH$_2$)$_n$CN, NR(CH$_2$)$_n$-heteroaryl-NR(CH$_2$)$_n$CON(R)$_2$, NR(CH$_2$)$_n$-heteroaryl-O(CH$_2$)$_n$CN, NR(CH$_2$)$_n$-heteroaryl-O(CH$_2$)$_n$CON(R)$_2$, and O(CH$_2$CH$_2$O)$_p$CH$_2$CH$_2$OR$^3$, where heteroaryl is a 5-12 membered ring system consisting of carbon atoms and from 1-4 heteroatoms selected from N, O, and S, and wherein aryl, heteroaryl, and biphenyl are substituted with 1-2 X$^2$;

provided that the heteroaryl in X is other than tetrazole;

X$^2$, at each occurrence, is independently selected from H, OR, C$_{1-4}$ alkyl, C$_{2-4}$ alkenyl, C$_{2-4}$ alkynyl, halogen, CF$_3$, nitro, —CN, CON(R)$_2$, and SO$_2$N(R)C$_{1-4}$alkyl;

Z is selected from H, C$_{1-4}$ alkyl, (CH$_2$)$_n$CONR$^3$R$^4$, CH$_2$CH=CHCON(R$^3$)$_2$, (CH$_2$)$_n$N(R$^3$)$_2$, and (CH$_2$)$_n$N$^+$(R$^3$)$_3$G$^-$;

G$^-$ is selected from Cl$^-$ and Br$^-$;

R$^3$ at each occurrence, is independently selected from H, C$_{1-4}$ alkyl, and benzyl;

R$^4$ at each occurrence, is independently selected from H, C$_{1-4}$ alkyl, and CH(L)CO$_2$R$^3$; and, L is selected from H, CH$_3$, CH$_2$CH$_3$, CH(CH$_3$)$_2$, CH$_2$CH(CH$_3$)$_2$, CH(CH$_3$)CH$_2$CH$_3$, CH$_2$CH$_2$SCH$_3$, phenyl, and benzyl.

[8] In another embodiment, the present invention provides a novel compound of formula Ie, or a stereoisomer or a pharmaceutically acceptable salt thereof:

Ie wherein:

R, at each occurrence, is independently selected from H and C$_{1-4}$ alkyl;

R$^1$ is selected from H and C$_{1-4}$ alkyl;

R$^2$ is selected from H and C$_{1-4}$ alkyl;

X is selected from H, OR$^3$, NR$^3$Z, OZ, SZ, SO$_2$NR$^3$R$^4$, CONR$^3$R$^4$, NHSO$_2$R, (CH$_2$)$_n$CONR$_2$, (CH$_2$)$_n$CN, NR—C$_{2-4}$ alkenyl, NRSO$_2$CH$_3$, CH$_2$-aryl, O(CH$_2$)$_n$-biphenyl, O(CH$_2$)$_n$-biphenyl-(CH$_2$)$_m$CN, O(CH$_2$)$_n$-biphenyl-(CH$_2$)$_m$CON(R)$_2$, NR(CH$_2$)$_n$-biphenyl, NR(CH$_2$)$_n$-biphenyl-(CH$_2$)$_m$CN, NR(CH$_2$)$_n$-biphenyl-(CH$_2$)$_m$CON(R)$_2$, O(CH$_2$)$_n$-aryl, O(CH$_2$)$_n$-heteroaryl, NR(CH$_2$)$_n$-aryl, NR(CH$_2$)$_n$-heteroaryl, O(CH$_2$)$_n$-aryl(CH$_2$)$_m$CN, O(CH$_2$)$_n$-aryl(CH$_2$)$_m$CON(R)$_2$, O(CH$_2$)$_n$-arylO(CH$_2$)$_n$CN, O(CH$_2$)$_n$-arylO(CH$_2$)$_n$CON(R)$_2$, O(CH$_2$)$_n$-aryl-NR(CH$_2$)$_n$CN, O(CH$_2$)$_n$-aryl-NR(CH$_2$)$_n$CON(R)$_2$ 5 NR(CH$_2$)$_n$-aryl(CH$_2$)$_m$CN, NR(CH$_2$)$_n$-aryl(CH$_2$)$_m$CON(R)$_2$, NR(CH$_2$)$_n$-aryl-NR(CH$_2$)$_n$CN, NR(CH$_2$)$_n$-aryl-NR(CH$_2$)$_n$CON(R)$_2$, NR(CH$_2$)$_n$-arylO(CH$_2$)$_n$CN, NR(CH$_2$)$_n$-aryl-O(CH$_2$)$_n$CON(R)$_2$, O(CH$_2$)$_n$-heteroaryl-(CH$_2$)$_m$CN, O(CH$_2$)$_n$-heteroaryl(CH$_2$)$_m$CON(R)$_2$, O(CH$_2$)$_n$-heteroaryl O(CH$_2$)$_n$CN, O(CH$_2$)$_n$-heteroarylO(CH$_2$)$_n$CON(R)$_2$, O(CH$_2$)$_n$-heteroaryl-NR(CH$_2$)$_n$CN, O(CH$_2$)$_n$-heteroaryl-NR(CH$_2$)$_n$CON(R)$_2$, NR(CH$_2$)$_n$-heteroaryl(CH$_2$)$_m$CN, NR(CH$_2$)$_n$-heteroaryl(CH$_2$)$_m$CON(R)$_2$, NR(CH$_2$)$_n$ heteroaryl-NR(CH$_2$)$_n$CN, NR(CH$_2$)$_n$-heteroaryl-NR(CH$_2$)$_n$CON(R)$_2$, NR(CH$_2$)$_n$-heteroaryl-O(CH$_2$)$_n$CN, NR(CH$_2$)$_n$-heteroaryl-O(CH$_2$)$_n$CON(R)$_2$, and O(CH$_2$CH$_2$O)$_p$CH$_2$CH$_2$OR$^3$, where heteroaryl is a 5-12 membered ring system consisting of carbon atoms and from 1-4 heteroatoms selected from N, O, and S, and wherein aryl, heteroaryl, and biphenyl are substituted with 1-2 X$^2$;

provided that the heteroaryl in X is other than tetrazole;

X$^2$, at each occurrence, is independently selected from H, OR, C$_{1-4}$ alkyl, C$_{2-4}$ alkenyl, C$_{2-4}$ alkynyl, halogen, CF$_3$, nitro, —CN, CON(R)$_2$, and SO$_2$N(R)C$_{1-4}$alkyl;

Z is selected from H, C$_{1-4}$ alkyl, (CH$_2$)$_n$CONR$^3$R$^4$, CH$_2$CH=CHCON(R$^3$)$_2$, (CH$_2$)$_n$N(R$^3$)$_2$, and (CH$_2$)$_n$N$^+$(R$^3$)$_3$G$^-$;

Y is selected from H, OR$^3$, NR$^3$Z, and NHSO$_2$R;

provided that at least one of X and Y is other than H or OR$^3$;

G$^-$ is selected from Cl$^-$ and Br$^-$;

R$^3$ at each occurrence, is independently selected from H, C$_{1-4}$ alkyl, and benzyl;

$R^4$ at each occurrence, is independently selected from H, $C_{1-4}$ alkyl, and $CH(L)CO_2R^3$; and, L is selected from H, $CH_3$, $CH_2CH_3$, $CH(CH_3)_2$, $CH_2CH(CH_3)_2$, $CH(CH_3)CH_2CH_3$, $CH_2CH_2SCH_3$, phenyl, and benzyl.

In another embodiment, the present invention provides novel pharmaceutical compositions, comprising: a pharmaceutically acceptable carrier and a therapeutically effective amount of a compound of the present invention or a stereoisomer or pharmaceutically acceptable salt thereof.

In another embodiment, the present invention provides a novel method for treating a disease, comprising: administering to a patient in need thereof a therapeutically effective amount of a compound of the present invention or a stereoisomer or pharmaceutically acceptable salt thereof, wherein the disease is selected from obesity, diabetes, cardiometabolic disorders, and a combination thereof.

In another embodiment, the cardiometabolic disorder is selected from hypertension, dyslipidemias (e.g., undesirable blood lipid levels, elevated cholesterol levels, and lowered LDL levels), high blood pressure, and insulin resistance.

In another embodiment, the present invention provides a novel method for treating a co-morbidity of obesity, comprising: administering to a patient in need thereof a therapeutically effective amount of a compound of the present invention or a stereoisomer or pharmaceutically acceptable salt thereof.

In another embodiment, the co-morbidity is selected from diabetes, Metabolic Syndrome, dementia, and heart disease.

In another embodiment, the co-morbidity is selected from hypertension; gallbladder disease; gastrointestinal disorders; menstrual irregularities; degenerative arthritis; venous statis ulcers; pulmonary hypoventilation syndrome; sleep apnea; snoring; coronary artery disease; arterial sclerotic disease; pseudotumor cerebri; accident proneness; increased risks with surgeries; osteoarthritis; high cholesterol; and, increased incidence of malignancies of the ovaries, cervix, uterus, breasts, prostrate, and gallbladder.

In another embodiment, the present invention provides a novel method for treating a CNS disorder, comprising: administering to a patient in need thereof a therapeutically effective amount of a compound of the present invention or a stereoisomer or pharmaceutically acceptable salt thereof.

In another embodiment, the CNS disorder is selected from acute and chronic neurological disorders, cognitive disorders, and memory deficits. Examples of these disorders include chronic or traumatic degenerative processes of the nervous system, which include Alzheimer's disease, other types of dementia, minimal cognitive impairment, and Parkinson's disease. Other examples of CNS disorders include psychiatric diseases, which include depression, anxiety, panic attack, social phobia, schizophrenia, and anorexia. Further examples of CNS disorders include withdrawal syndromes induced by alcohol, nicotine and other addictive drugs. Additional examples of CNS disorders include neuropathic pain and neuroinflamatory diseases (e.g., multiple sclerosis).

In another embodiment, the present invention also provides a method of preventing or reversing the deposition of adipose tissue in a mammal by the administration of a MAO-B inhibitor. By preventing or reversing the deposition of adipose tissue, MAO-B inhibitors are expected to reduce the incidence or severity of obesity, thereby reducing the incidence or severity of associated co-morbidities.

In another embodiment, the present invention provides a compound of the present invention for use in therapy.

In another embodiment, the present invention provides the use of compounds of the present invention for the manufacture of a medicament for the treatment of obesity, diabetes, cardiometabolic disorders, and a combination thereof.

In another embodiment, the present invention provides the use of novel compounds for the manufacture of a medicament for the treatment of CNS disorders.

The present invention may be embodied in other specific forms without departing from the spirit or essential attributes thereof. This invention encompasses all combinations of preferred or narrowed aspects/embodiments of the invention noted herein. Any and all embodiments of the present invention may be taken in conjunction with any other embodiment or embodiments to describe an additional embodiment. Each individual element of an embodiment is intended to be taken individually as its own independent embodiment. Furthermore, any element of an embodiment is meant to be combined with any and all other elements from any embodiment to describe an additional embodiment.

Definitions

The examples provided in the definitions present in this application are non-inclusive unless otherwise stated. They include but are not limited to the recited examples.

Acid functionalities include carboxylic acids, carboxylic acid esters, tetrazole, $SO_2OR^3$, and $PO(OR^3)_2$.

The compounds herein described may have asymmetric centers, geometric centers (e.g., double bond), or both. All chiral, diastereomeric, racemic forms and all geometric isomeric forms of a structure are intended, unless the specific stereochemistry or isomeric form is specifically indicated. Compounds of the present invention containing an asymmetrically substituted atom may be isolated in optically active or racemic forms. It is well known in the art how to prepare optically active forms, such as by resolution of racemic forms, by synthesis from optically active starting materials, or through use of chiral auxiliaries. Geometric isomers of olefins, C=N double bonds, or other types of double bonds may be present in the compounds described herein, and all such stable isomers are included in the present invention. Specifically, cis and trans geometric isomers of the compounds of the present invention may also exist and may be isolated as a mixture of isomers or as separated isomeric forms. All processes used to prepare compounds of the present invention and intermediates made therein are considered to be part of the present invention. All tautomers of shown or described compounds are also considered to be part of the present invention.

The present invention includes all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

Examples of the molecular weight of the compounds of the present invention include (a) less than about 500, 550, 600, 650, 700, 750, 800, 850, 900, 950, or 1000 grams per mole; (b) less than about 950 grams per mole; (c) less than about 850 grams per mole; and, (d) less than about 750 grams per mole.

"Alkyl" includes both branched and straight-chain saturated aliphatic hydrocarbon groups having the specified number of carbon atoms. $C_{1-6}$ alkyl, for example, includes $C_1$, $C_2$, $C_3$, $C_4$, $C_5$, and $C_6$ alkyl groups. Examples of alkyl include methyl, ethyl, n-propyl, i-propyl, n-butyl, s-butyl, t-butyl, n-pentyl, and s-pentyl.

"Alkenyl" includes the specified number of hydrocarbon atoms in either straight or branched configuration with one or more unsaturated carbon-carbon bonds that may occur in any stable point along the chain, such as ethenyl and propenyl. $C_{2-6}$ alkenyl includes $C_2$, $C_3$, $C_4$, $C_5$, and $C_6$ alkenyl groups.

"Alkynyl" includes the specified number of hydrocarbon atoms in either straight or branched configuration with one or more triple carbon-carbon bonds that may occur in any stable point along the chain, such as ethynyl and propynyl. $C_{2-6}$ Alkynyl includes $C_2$, $C_3$, $C_4$, $C_5$, and $C_6$ alkynyl groups.

"Cycloalkyl" includes the specified number of hydrocarbon atoms in a saturated ring, such as cyclopropyl, cyclobutyl, cyclopentyl, cyclohexyl, cycloheptyl, and cyclooctyl. $C_{3-8}$ cycloalkyl includes $C_3$, $C_4$, $C_5$, $C_6$, $C_7$, and $C_8$ cycloalkyl groups.

"Alkoxy" represents an alkyl group as defined above with the indicated number of hydrocarbon atoms attached through an oxygen bridge. $C_{1-6}$ alkoxy, includes $C_1$, $C_2$, $C_3$, $C_4$, $C_5$, and $C_6$ alkoxy groups. Examples of alkoxy include methoxy, ethoxy, n-propoxy, i-propoxy, n-butoxy, s-butoxy, t-butoxy, n-pentoxy, and s-pentoxy.

"Halo" or "halogen" refers to fluoro, chloro, bromo, and iodo.

"Counterion" is used to represent a small, negatively charged species, such as chloride, bromide, hydroxide, acetate, and sulfate.

"Aryl" refers to any stable 6, 7, 8, 9, 10, 11, 12, or 13 membered monocyclic, bicyclic, or tricyclic ring, wherein at least one ring, if more than one is present, is aromatic. Examples of aryl include fluorenyl, phenyl, naphthyl, indanyl, adamantyl, and tetrahydronaphthyl.

"Heteroaryl" refers to any stable 5, 6, 7, 8, 9, 10, 11, or 12 membered monocyclic, bicyclic, or tricyclic heterocyclic ring that is aromatic, and which consists of carbon atoms and 1, 2, 3, or 4 heteroatoms independently selected from the group consisting of N, O, and S. If the heteroaryl group is bicyclic or tricyclic, then at least one of the two or three rings must contain a heteroatom, though both or all three may each contain one or more heteroatoms. If the heteroaryl group is bicyclic or tricyclic, then only one of the rings must be aromatic. The N group may be N, NH, or N-substituent, depending on the chosen ring and if substituents are recited. The nitrogen and sulfur heteroatoms may optionally be oxidized (e.g., S, S(O), S(O)$_2$, and N—O). The heteroaryl ring may be attached to its pendant group at any heteroatom or carbon atom that results in a stable structure. The heteroaryl rings described herein may be substituted on carbon or on a nitrogen atom if the resulting compound is stable.

Examples of heteroaryl includes acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, naphthyridinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, pteridinyl, pyranyl, pyrazinyl, pyrazolyl, pyridazinyl, pyridooxazole, pyridoimidazole, pyridothiazole, pyridinyl, pyridyl, pyrimidinyl, 2H-pyrrolyl, pyrrolyl, quinazolinyl, quinolinyl, 4H-quinolizinyl, quinoxalinyl, quinuclidinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

Preventing the deposition of adipose tissue covers methods of treating wherein the levels of adipose tissue of a subject remain about the same as prior to being treated in accordance with the present invention (i.e., its pre-administration level) or not more than about 1, 2, 3, 4, 5, 6, 7, 8, 9, or 10% greater than pre-administration level (particularly when the subject is pre-disposed to increasing adipose tissue levels).

Reversing the deposition of adipose tissue covers methods of treating wherein the levels of adipose tissue of a subject are lower than those prior to being treated in accordance with the present invention (i.e., its pre-administration level). Examples of lower include 1, 2, 3, 4, 5, 6, 7, 8, 9, 10, 11, 12, 13, 14, 15, 16, 17, 18, 19, 20% or more lower than pre-administration level.

Mammal and patient covers warm blooded mammals that are typically under medical care (e.g., humans and domesticated animals). Examples of mammals include (a) feline, canine, equine, bovine, and human and (b) human.

"Treating" or "treatment" covers the treatment of a disease-state in a mammal, and includes: (a) preventing the disease-state from occurring in a mammal, in particular, when such mammal is predisposed to the disease-state but has not yet been diagnosed as having it; (b) inhibiting the disease-state, e.g., arresting it development; and/or (c) relieving the disease-state, e.g., causing regression of the disease state until a desired endpoint is reached. Treating also includes the amelioration of a symptom of a disease (e.g., lessen the pain or discomfort), wherein such amelioration may or may not be directly affecting the disease (e.g., cause, transmission, expression, etc.).

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 1,2-ethanedisulfonic, 2-acetoxybenzoic, 2-hydroxyethanesulfonic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methanesulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluenesulfonic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 18th ed., Mack Publishing Company, Easton, Pa., 1990, p 1445, the disclosure of which is hereby incorporated by reference.

"Therapeutically effective amount" includes an amount of a compound of the present invention that is effective when administered alone or in combination to treat obesity or another indication listed herein. "Therapeutically effective amount" also includes an amount of the combination of compounds claimed that is effective to treat the desired indication. The combination of compounds is preferably a synergistic combination. Synergy, as described, for example, by Chou and Talalay, *Adv. Enzyme Regul.* 1984, 22:27-55, occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased effect, or some other beneficial effect of the combination compared with the individual components.

Utility

Obesity is defined as having a body mass index (BMI) of 30 or above. The index is a measure of an individual's body weight relative to height. BMI is calculated by dividing body weight (in kilograms) by height (in meters) squared. Normal and healthy body weight is defined as having a BMI between 20 and 24.9. Overweight is defined as having a BMI of 25 or above. Obesity has reached epidemic proportions in the U.S., with 44 million obese Americans, and an additional eighty million deemed medically overweight.

Obesity is a disease characterized as a condition resulting from the excess accumulation of adipose tissue, especially adipose tissue localized in the abdominal area. It is desirable to treat overweight or obese patients by reducing their amount of adipose tissue, and thereby reducing their overall body weight to within the normal range for their sex and height. In this way, their risk for co-morbidities such as diabetes and cardiovascular disease will be reduced. It is also desirable to prevent normal weight individuals from accumulating additional, excess adipose tissue, effectively maintaining their body weights at a BMI<25, and preventing the development of co-morbidities. It is also desirable to control obesity, effectively preventing overweight and obese individuals from accumulating additional, excess adipose tissue, reducing the risk of further exacerbating their co-morbidities.

There exist two forms of MAO, designated MAO-A and MAO-B. The two forms differ with respect to substrate and inhibitor specificities and amino acid number and sequence. A preferred substrate for MAO-B is beta-phenylethylamine. In contrast, a preferred substrate for MAO-A is serotonin. Some MAO inhibitors show selectivity for MAO-A or for MAO-B, whereas other MAO inhibitors show little, if any selectivity. For example, the MAO inhibitor clorgyline preferentially inhibits MAO-A; the MAO inhibitor L-selegiline preferentially inhibits MAO-B; and, the MAO inhibitor iproniazid is non-selective (i.e., has a similar affinity for both). Examples of selectivity include a compound having about 2, 3, 4, 5, 6, 7, 8, 9, 10, 20, 30, 40, 50, 100, 200, 300, 400, 500, 600, 700, 800, 900, 1000, or more fold higher affinity for one form of MAO than for the other form. One of ordinary skill in the art recognizes that there can be some difficulty in classifying MAO inhibitors. Some compounds may selectively inhibit one form of MAO in vitro and then lose their selectivity in vivo. Also, selectivity of a compound may vary from species to species or from tissue to tissue. In the context of the present invention, it is desirable to inhibit MAO-B activity in vivo in a mammal. Thus, selectivity and affinity are based on the in vivo activity of the MAO inhibitor and the mammalian species to which it is being or to be administered. Examples of the selectivity of a MAO-B inhibitor of the present invention include (a) at least a 2, 3, 4, 5, 6, 7, 8, 9, 10, 20, 30, 40, 50, to 100-fold greater affinity for MAO-B than MAO-A in the mammalian species (e.g., human) to be treated and (b) at least 100-fold greater affinity for MAO-B than MAO-A in the mammalian species (e.g., human) to be treated.

Some of the compounds of the present invention have been designed to have reduced CNS exposure by virtue of their inability or limited ability to penetrate the blood-brain barrier (e.g., quaternary salts or acid substituents) or by their participation in active transport systems, thus reducing centrally mediated side-effects, a potential problem with many anti-obesity agents.

Other compounds of the present invention are expected to penetrate the blood-brain barrier and therefore also be useful to treat CNS disorders (e.g., Parkinson's disease, depression, and Alzheimer's disease).

MAO enzymes are also located in a number of peripheral (non-CNS) tissues, including adipose tissue, muscle and liver. In order to treat non-CNS disorders (e.g., obesity, diabetes, and/or cardiometabolic disorders), it is necessary to administer enough of a drug sufficient to inhibit MAO in peripheral tissues. MAO inhibitors in use today to treat various psychiatric and neurological diseases, regardless of route of administration, enter the CNS from the systemic circulation. While present in the systemic circulation, such drugs have access to peripheral tissues, including adipose tissue, liver, and muscle. One of skill in the art recognizes that MAO inhibitors intended to enter the CNS from the systemic circulation in order to treat psychiatric and neurological diseases also have access to MAO in peripheral tissues, including adipose tissue, liver, and muscle. Thus, an MAO inhibitor useful for treating non-CNS disorders may have some access to the CNS from the systemic circulation.

Drugs enter the CNS from the systemic circulation by crossing the blood-brain barrier (BBB). The BBB is a highly specialized 'gate-keeper' that protects the brain by preventing the entry of many potentially harmful substances into the CNS from the systemic circulation. Much is known about the BBB, and of the physical-chemical properties required for compounds transported across it.

Drugs that do not cross the BBB into the CNS or that are readily eliminated through transport mechanisms (J Clin Invest. 97, 2517 (1996)) are known in the literature and have low CNS activity due to their inability to develop brain levels necessary for pharmacological action. The BBB has at least one mechanism to remove drugs prior to their accumulation in the CNS. P-Glycoproteins (P-gp) localized in plasma membrane of the BBB can influence the brain penetration and pharmacological activity of many drugs through translocation across membranes. The lack of accumulation into the brain by some drugs can be explained by their active removal from the brain by P-gp residing in the BBB. For example, the typical opioid drug loperamide, clinically used as an antidiarrheal, is actively removed from the brain by P-gp, thus explaining its lack of opiate-like CNS effects. Another example is domperidone, a dopamine receptor blocker that participates in the P-gp transport (J Clin Invest. 97, 2517 (1996)). Whereas dopamine receptor blockers that cross the BBB can be used to treat schizophrenia, the readily-eliminated domperidone can be used to prevent emesis, without the likelihood of producing adverse CNS effects.

In addition to the above compounds, agents possessing structural characteristics that retard or prevent BBB penetration or contribute to participation in active elimination processes have been identified in various classes of therapeutics.

These include antihistamines (Drug Metab. Dispos. 31, 312 (2003)), beta-adrenergic receptor antagonists (B-blockers) (Eur. J. Clin. Pharmacol. 28, Suppl: 21-3 (1985); Br. J. Clin. Pharmacol., 11 (6), 549-553 (1981)), non-nucleoside reverse transcriptase inhibitors (NNRTIs)(J. Pharm Sci., 88 (10) 950-954 (1999)), and opioid antagonists. This latter group has been tested in relation to their activity in the GI tract. These peripherally selective opioid antagonists are described in various US patents as being useful in the treatment of non-CNS pathologies in mammals, in particular those of the GI tract (see U.S. Pat. No. 5,260,542; U.S. Pat. No. 5,434,171; U.S. Pat. No. 5,159,081; and U.S. Pat. No. 5,270,238).

Other types of non-brain penetrant compounds can be prepared through the creation of a charge within the molecule. Thus, the addition of a methyl group to the tertiary amine functionality of the drugs scopolamine or atropine, unlike the parent molecules, prevents their passage across the BBB through the presence of a positive charge. However, the new molecules (methyl-scopolamine and methyl-atropine) retain their full anticholinergic pharmacological properties. As such, these drugs can also be used to treat peripheral diseases, without the concern of adverse CNS effects. The quaternary ammonium compound methylnaltrexone is also used for the prevention and/or treatment of opioid and non-opioid induced side effects associated with opioid administration.

MAO-B inhibitors such as selegiline have been useful in the treatment of CNS disorders. The unexpected discovery that the anti-obesity activity mediated by these agents is mediated by a non-CNS mechanism may make it desirable that the compounds of the present invention be peripherally restricted, i.e., have an inability or limited ability to cross the BBB or be readily eliminated from the brain through active transport systems, when a non-CNS disorder is to be treated. It may be desirable for the compounds of the present invention to be peripherally restricted, which in turn will result in no or very limited CNS effects. Compounds that provide peripherally mediated anti-obesity properties should result in therapeutic agents with greater safety, as previously demonstrated in earlier classes of peripherally restricted agents. It can be desirable that the compounds of the present invention, when administered in a therapeutically effective amount, have no or very limited CNS effects. It can also be desirable that the lack of CNS effects is a result of the compounds of the present invention having minimal brain concentrations when administered in therapeutically effective amounts. In this context, minimal brain concentrations means levels that are too low to be therapeutically effective for the treatment of a CNS indication or too low to cause significant or measurable deleterious or undesired side effects. It is noted that CNS activity is desirable when seeking to treat a CNS disorder.

Compound A is lazabemide when $A^1$ is N; $A^2$ is C—Cl; A, $A^3$, and $A^4$ are all CH; Q is C=O; and R, $R^1$, and $R^2$ are all H. Lazabemide is a drug that crosses the BBB and is indicated, but not marketed, for the treatment of Parkinson's disease. In compound A, one of A, $A^1$, $A^2$, $A^3$, $A^4$, and Q is a group capable of reducing or limiting the CNS activity of compound A. This reduced or limited CNS activity occurs via at least one of A, $A^1$, $A^2$, $A^3$, $A^4$, and Q being a group that either limits compound A's ability to cross the BBB relative to that of lazabemide or enables it to be actively removed at a rate greater than that of lazabemide. Examples of brain levels of compound A include levels that are (a) from 50, 55, 60, 65, 70, 75, 80, 85, 90, 91, 92, 93, 94, 95, 96, 97, 98, 99, to 100% lower than lazabemide, when administered at the same dosage; (b) from 90, 91, 92, 93, 94, 95, 96, 97, 98, 99, to 100% lower than lazabemide, when administered at the same dosage; and, (c) from 98, 99, to 100% lower than lazabemide, when administered at the same dosage.

Most methods of treating obesity are dependent on a significant reduction in energy intake, either by a decrease in food intake (e.g., sibutramine) or by inhibition of fat absorption (e.g., orlistat). In the present invention, it can be desirable for adipose tissue to be significantly reduced in the absence of a significant reduction in food intake. The weight loss, as a result of the present invention, comes from the treatment with an MAO-B inhibitor, largely independent of appetite and food intake. Examples of the level of food intake during adipose tissue loss include (a) food intake is maintained, increased or about 0, 1, 2, 3, 4, 5, 6, 7, 8, 9, 10, 11, 12, 13, 14, 15, 16, 17, 18, 19, or 20% below the normal range of the subject prior to being treated in accordance with the present invention (i.e., its pre-administration level); (b) food intake is maintained, increased, or about 0, 1, 2, 3, 4, 5, 6, 7, 8, 9, 10, 11, 12, 13, 14, or 15% below its pre-administration level; (c) food intake is maintained, increased or about 0, 1, 2, 3, 4, 5, 6, 7, 8, 9, or 10% below its pre-administration level; and (d) food intake level is maintained, increased or about 0, 1, 2, 3, 4, or 5% below its pre-administration level.

In some cases, loss of adipose tissue can be accompanied by a concomitant loss of lean muscle mass. This is particularly evident in cancer patients who show a wasting of all body tissue components, including adipose tissue and lean muscle mass. In the present invention, however, it can be desirable for body fat to be significantly reduced in the absence of a significant reduction in lean body mass. Adipose tissue loss comes from treatment with an MAO-B inhibitor, independent of a significant change in lean body mass. Examples of the level of lean body mass during adipose tissue loss include (a) lean body mass is maintained, increased, or is no more than about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30% below the normal range of the subject prior to being treated in accordance with the present invention (i.e., its pre-administration level); (b) lean body mass is maintained, increased, or is no more than about 1, 2, 3, 4, 5, 6, 7, 8, 9, 10, 11, 12, 13, 14, or 15% below pre-administration levels; (c) lean body mass is maintained, increased, or is no more than about 1, 2, 3, 4, 5, 6, 7, 8, 9, or 10% below pre-administration levels; and (d) lean body mass is maintained, increased, or is no more than about 1, 2, 3, 4, or 5% below pre-administration levels.

In some cases, loss of adipose tissue can be accompanied by a concomitant loss of water mass. This is particularly evident with diet regimens that promote dehydration. In the present invention, it can be desirable for body fat to be significantly reduced in the absence of a significant reduction in water mass. In other words, adipose tissue loss comes from treatment with an MAO-B inhibitor, independent of a significant change in water mass. Examples of the level of water mass during adipose tissue loss include (a) water mass is maintained, increased, or is no more than about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30% below the normal range of the subject prior to being treated in accordance with the present invention (i.e., its pre-administration level); (b) water mass is maintained, increased, or is no more than about 1, 2, 3, 4, 5, 6, 7, 8, 9, 10, 11, 12, 13, 14, or 15% below pre-administration levels; (c) water mass is maintained, increased, or is no more than about 1, 2, 3, 4, 5, 6, 7, 8, 9, or 10% below pre-administration levels; and (d) water mass is maintained, increased, or is no more than about 1, 2, 3, 4, or 5% below pre-administration levels.

Sibutramine and orlistat are currently marketed for use in the treatment of obesity. These two compounds achieve weight loss through entirely different mechanisms. Sibutramine, a CNS appetite suppressant, inhibits the neuronal reuptake of serotonin and noradrenaline. Orlistat inhibits gut lipase enzymes that are responsible for breaking down ingested fat.

The mechanism of action of MAO-B inhibitors is believed to be entirely different from appetite suppressants, gut lipase inhibitors, and other agents with similar indications (e.g., serotonin agonists, leptin, and fatty acid synthase inhibitors). Co-administration of a MAO-B inhibitor together with one or more other agents that are useful for treating the indications described above (e.g., obesity, diabetes, cardiometabolic disorders, and a combination thereof) is expected to be beneficial, by producing, for example, either additive or synergistic effects. Examples of additional agents include an appetite suppressant and a lipase inhibitor. Therefore, the present invention provides a method of treating obesity, diabetes, and/or cardiometabolic disorders, comprising administering a therapeutically effective amount of a compound of the present invention and a second component selected from an appetite suppressant (e.g., sibutramine, phentermine, fenfluramine) and a gut lipase inhibitor (e.g., orlistat).

MAO-B inhibitors are expected to promote weight loss without appreciably reducing caloric intake. Co-administration of an MAO-B inhibitor together with an appetite suppressant is expected to produce either additive or synergistic effects on weight loss. Similarly, co-administration of an MAO-B inhibitor together with a lipase inhibitor is expected to produce either additive or synergistic effects on weight loss.

The ability of compounds to inhibit MAOs can be determined using the method of R. Uebelhack et al., Pharmacopsychiatry 31, 187-192 (1988)(as described below).

Preparation of platelet-rich plasma and platelets. Venous blood from healthy subjects was collected between 8 and 8.30 a.m. after an overnight fast into EDTA-containing vacutainer tubes (11.6 mg EDTA/ml blood). After centrifugation of the blood at 250×g for 15 minutes at 20° C., the supernatant platelet-rich plasma (PRP) was collected and the number of platelets in PRP counted with a cell counter (MOIAB, Hilden, Germany). 2 ml of PRP was spun at 1500×g for 10 min to yield a platelet pellet. The pellet was washed three times with ice-cold saline, resuspended in 2 ml Soerensen phoshate buffer, pH 7.4 and stored at −18° C. for one day.

MAO assay. Fresh PRP or frozen platelet suspension (100 µL) was generally preincubated for 10 min in the absence or presence of drugs at 37° C. in 100 µL of 0.9% NaCl solution or phosphate buffer pH 7.4, respectively, at 37° C. 50 µL of 2-phenylethylamine-[ethyl-1-14C]hydrochloride (PEA) solution (specific activity 56 Ci/mol, Amersham) was then added in a final concentration of 5 µM, and the incubation was continued for 30 min. The reaction was terminated by the addition of 50 µL of 4M $HClO_4$. The reaction product of MAO, phenylacetaldehyde, was extracted into 2 mL of n-hexane. An aliquot of the organic phase was added to scintillator cocktail and the radioactivity was determined using a liquid scintillation counter. Product formation was linear with time for at least 60 min with appropriate platelet numbers. Blank values were obtained by including 2 mM pargyline in the incubation mixtures. All assays were performed in duplicate.

The ability of compounds to inhibit MAO activity can also be determined using the following method. cDNA's encoding human MAO-B can be transiently transfected into EBNA cells using the procedure described by E.-J. Schlaeger and K. Christensen (Transient Gene Expression in Mammalian Cells Grown in Serum-free Suspension Culture; Cytotechnology, 15: 1-13, 1998). After transfection, cells are homogeneized by means of a Polytron homogeneiser in 20 mM Tris HCl buffer, pH 8.0, containing 0.5 mM EGTA and 0.5 mM phenylmethanesulfonyl fluoride. Cell membranes are obtained by centrifugation at 45,000×g and, after two rinsing steps with 20 mM Tris HCl buffer, pH 8.0, containing 0.5 mM EGTA, membranes are eventually re-suspended in buffer and aliquots stored at −80° C. until use.

MAO-B enzymatic activity can be assayed using a spectrophotometric assay adapted from the method described by M. Zhou and N. Panchuk-Voloshina (A One-Step Fluorometric Method for the Continuous Measurement of Monoamine Oxidase Activity, Analytical Biochemistry, 253: 169-174, 1997). Briefly, membrane aliquots are incubated in 0.1 M potassium phosphate buffer, pH 7.4, for 30 min at 37° C. with or without various concentrations of the compounds. After incubation, the enzymatic reaction is started by the addition of the MAO substrate tyramine together with 1 U/ml horseradish peroxidase (Roche Biochemicals) and 80 µM N-acetyl-3,7,-dihydroxyphenoxazine (Amplex Red, Molecular Probes). The samples are further incubated for 30 min at 37° C. in a final volume of 200 µl and absorbance is determined at a wavelength of 570 nm using a SpectraMax plate reader (Molecular Devices). Background (non-specific) absorbance is determined in the presence of 10 µM L-deprenyl for MAO-B. $IC_{50}$ values are determined from inhibition curves obtained using nine inhibitor concentrations in duplicate, by fitting data to a four parameter logistic equation.

Compounds of the present invention are expected to be MAO-B inhibitors. Representative compounds have been tested, as measured in the assay described herein, and have been shown to be active as their $IC_{50}$ values were found to be in the range of ≦10 µM. Compounds of the present invention are considered to be MAO-B inhibitors if they have an $IC_{50}$ value less than or equal to 10 µM. Additional examples of desirable activity levels of MAO-B inhibitors useful in the present invention include (a) an $IC_{50}$ value of 1 µM or lower, (b) an $IC_{50}$ value of 0.1 µM or lower, (c) an $IC_{50}$ value of 0.01 µM or lower, (d) an $IC_{50}$ value of 0.001 µM or lower, and (e) an $IC_{50}$ value of 0.0001 µM or lower.

In the present invention, MAO-B inhibitor(s) can be administered enterally, parenterally, orally, and transdermally. One skilled in this art is aware that the routes of administering the compounds of the present invention may vary significantly. In addition to other oral administrations, sustained release compositions may be favored. Other examples of routes include injections (e.g., intravenous, intramuscular, and intraperitoneal); subcutaneous; subdermal implants; buccal, sublingual, topical (e.g., a dermal or transdermal patch), rectal, vaginal, and intranasal administrations. Bioerodible, non-bioerodible, biodegradable, and non-biodegradable systems of administration may also be used.

If a solid composition in the form of tablets is prepared, the main active ingredient can be mixed with a pharmaceutical vehicle, examples of which include silica, starch, lactose, magnesium stearate, and talc. The tablets can be coated with sucrose or another appropriate substance or they can be treated so as to have a sustained or delayed activity and so as to release a predetermined amount of active ingredient continuously. Gelatin capsules can be obtained by mixing the active ingredient with a diluent and incorporating the resulting mixture into soft or hard gelatin capsules. A syrup or elixir can contain the active ingredient in conjunction with a sweetener, which is preferably calorie-free, an antiseptic (e.g., methylparaben and/or propylparaben), a flavoring, and an appropriate color. Water-dispersible powders or granules can contain the active ingredient mixed with dispersants or wetting agents or with suspending agents such as polyvinylpyrrolidone, as well as with sweeteners or taste correctors. Rectal administration can be effected using suppositories, which are prepared with binders melting at the rectal temperature (e.g., cocoa butter and/or polyethylene glycols). Parenteral administration can be effected using aqueous suspensions, isotonic saline solutions, or injectable sterile solutions, which contain pharmacologically compatible dispersants and/or wetting agents (e.g., propylene glycol and/or polyethylene glycol). The active ingredient can also be formulated as microcapsules or microspheres, optionally with one or more carriers or additives. The active ingredient can also be presented in the form of a complex with a cyclodextrin, for example α-, β-, or γ-cyclodextrin, 2-hydroxypropyl-β-cyclodextrin, and/or methyl-β-cyclodextrin.

The dose of the MAO-B inhibitor administered daily will vary on an individual basis and to some extent may be determined by the severity of the disease being treated (e.g., obesity). The dose of the MAO-B inhibitor will also vary depending on the MAO-B inhibitor administered. An example of a range of dosages of an MAO-B inhibitor is about from 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 2, 3, 4, 5, 6, 7, 8, 9, 10, 15, 20, 25, 30, 35, 40, 45, 50, 55, 60, 65, 70, 76, 80, 85, 90, 95, to 100 mg/kg of mammal body weight. The MAO-B inhibitor can be administered in a single dose or in a number of smaller doses over a period of time. The length of time during which the MAO-B inhibitor is administered varies on an individual basis, and can continue until the desired results are achieved (i.e., reduction of body fat, or prevention of a gain in body fat). Therapy could, therefore, last from 1 day to weeks, months, or even years depending upon the subject being treated, the desired results, and how quickly the subject responds to treatment in accordance with the present invention.

A possible example of a tablet of the present invention is as follows.

| Ingredient | mg/Tablet |
|---|---|
| Active ingredient | 100 |
| Powdered lactose | 95 |
| White corn starch | 35 |
| Polyvinylpyrrolidone | 8 |
| Na carboxymethylstarch | 10 |
| Magnesium stearate | 2 |
| Tablet weight | 250 |

A possible example of a capsule of the present invention is as follows.

| Ingredient | mg/Tablet |
|---|---|
| Active ingredient | 50 |
| Crystalline lactose | 60 |
| Microcrystalline cellulose | 34 |
| Talc | 5 |
| Magnesium stearate | 1 |
| Capsule fill weight | 150 |

In the above capsule, the active ingredient has a suitable particle size. The crystalline lactose and the microcrystalline cellulose are homogeneously mixed with one another, sieved, and thereafter the talc and magnesium stearate are admixed. The final mixture is filled into hard gelatin capsules of suitable size.

A possible example of an injection solution of the present invention is as follows.

| Ingredient | mg/Tablet |
|---|---|
| Active substance | 1.0 mg |
| 1 N HCl | 20.0 μl |
| acetic acid | 0.5 mg |
| NaCl | 8.0 mg |
| Phenol | 10.0 mg |
| 1 N NaOH | q.s. ad pH 5 |
| $H_2O$ | q.s. ad 1 mL |

Synthesis

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley and Sons, 1991). All references cited herein are hereby incorporated in their entirety herein by reference.

Scheme 1

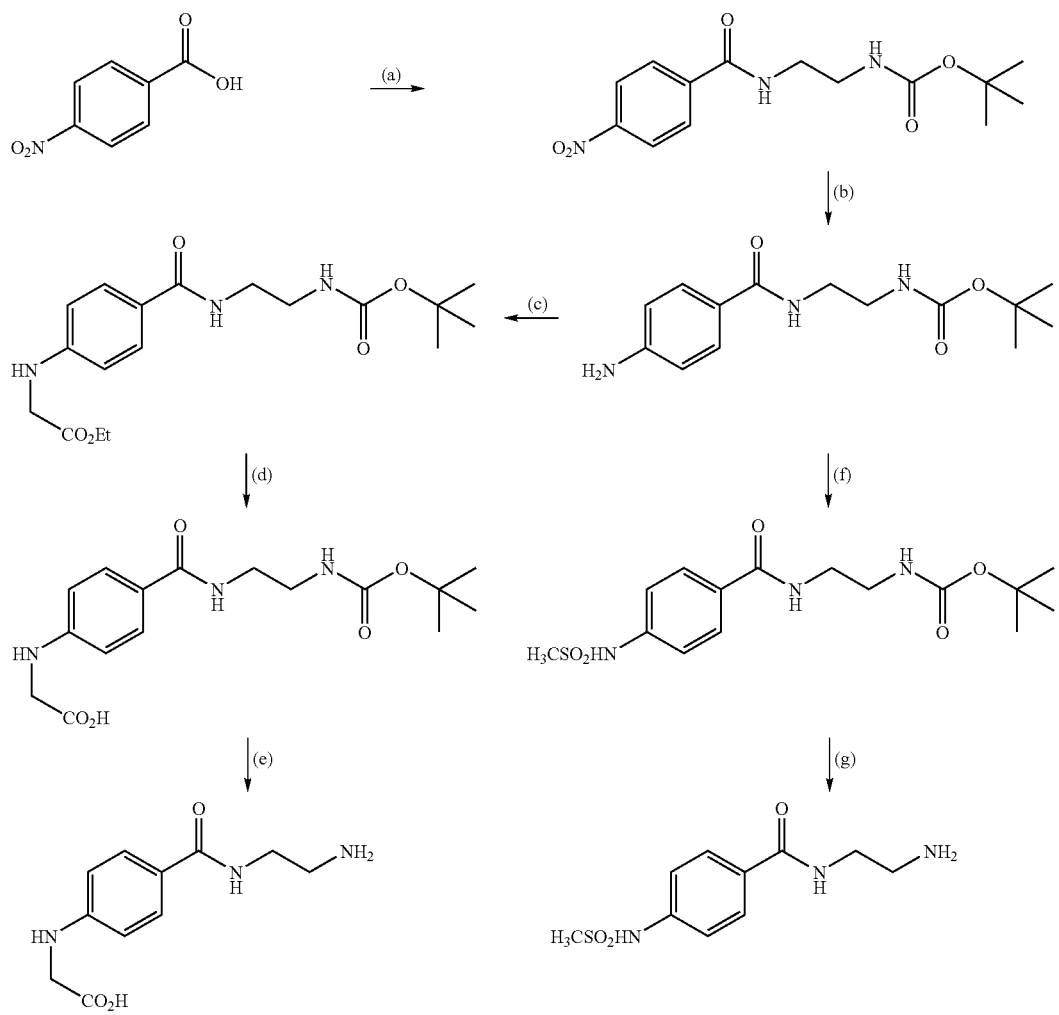

As shown in Scheme 1, nitrobenzoic acid can be treated with ethyl chloroformate in an appropriate solvent such as methylene chloride in the presence of triethylamine and the mixed anhydride that should be formed can be reacted with t-butyl (2-aminoethyl)carbamate to afford the benzamide derivative (step a). The nitrobenzene when treated with sodium dithionite in aqueous dioxane containing ammonium hydroxide solution should yield the aniline derivative (step b). Alkylation of the aniline with ethyl bromoacetate under basic conditions should give the ester (step c) that can be hydrolyzed with lithium hydroxide in aqueous THF to give the acid (step d). Removal of the t-BOC group using TFA in methylene chloride should produce the amino acid (step e). Alternatively, the aniline derivative can be sulfonylated with methanesulfonyl chloride to give the sulfonamide (step f), and subsequent removal of the t-BOC group using TFA in methylene chloride should give the aminoethylbenzamide derivative (step g).

Scheme 2

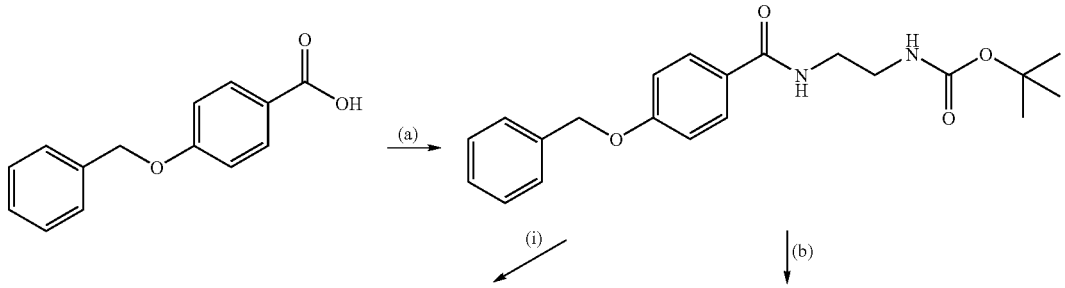

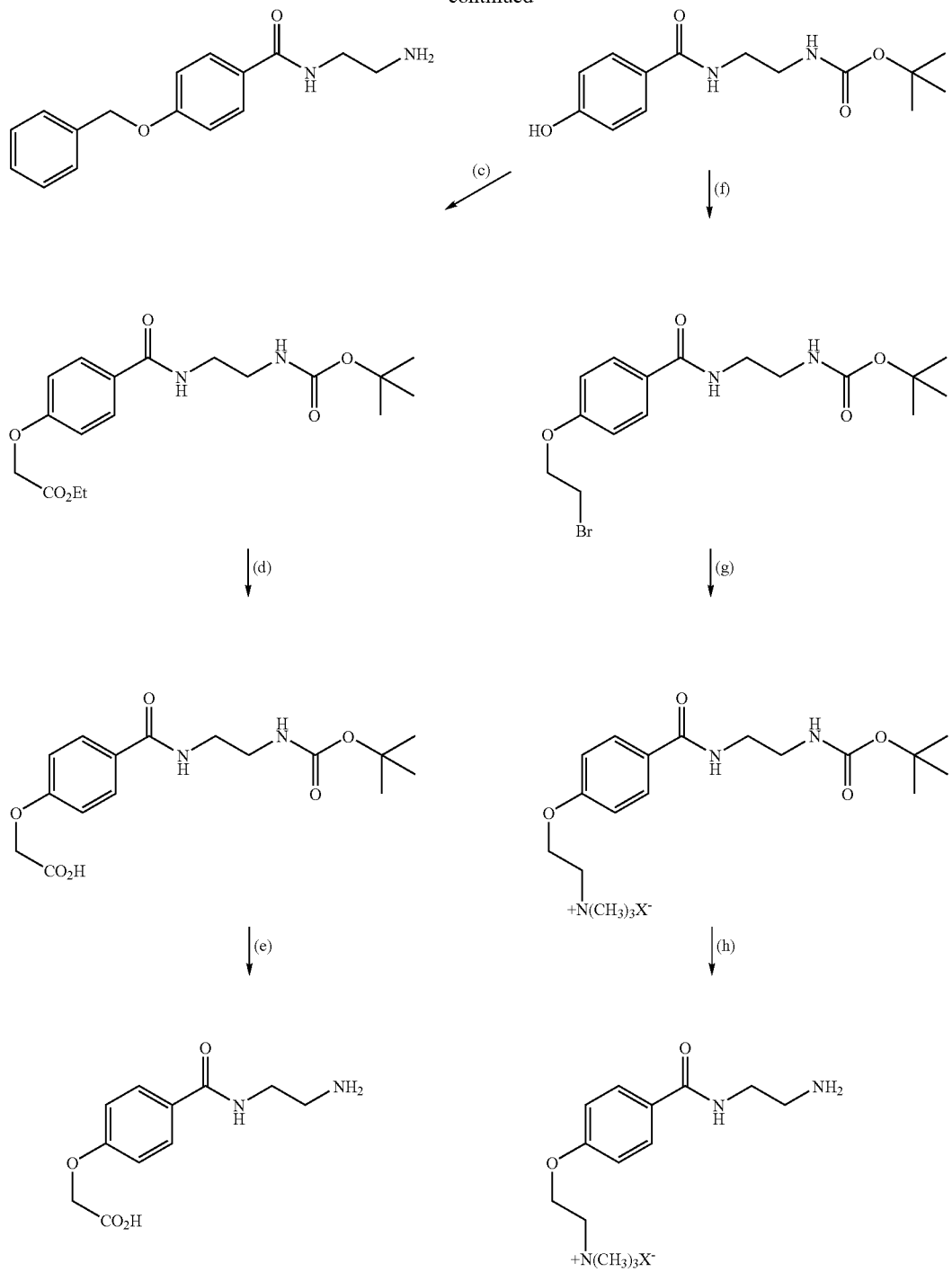

As described in Scheme 2, benzyloxybenzoic acid can be treated with ethyl chloroformate in an appropriate solvent such as methylene chloride in the presence of triethylamine and the mixed anhydride that should be formed can be reacted with t-butyl (2-aminoethyl)carbamate to afford the benzamide derivative (step a). Removal of the benzyl group can be achieved using palladium-catalyzed hydrogenolysis in ethanol to yield the phenol (step b). The phenol can be alkylated with ethyl bromoacetate under basic conditions to give the ester (step c) that can be hydrolyzed with lithium hydroxide in aqueous THF to give the acid (step d). Removal of the t-BOC group using TFA in methylene chloride should produce the amino acid (step e). Alternatively, the phenol can be alkylated with 1,2 dibromoethane to give the alkyl halide (step f). Treatment of the alkyl halide with trimethylamine should give the quaternary ammonium salt (step g) and subsequent removal of the t-BOC group with TFA in methylene chloride solution should afford the aminoethylbenzamide derivative (step h). Removal of the t-BOC group from the product of step a using TFA in methylene chloride will provide the benzyloxy amino compound (step i).

Scheme 3
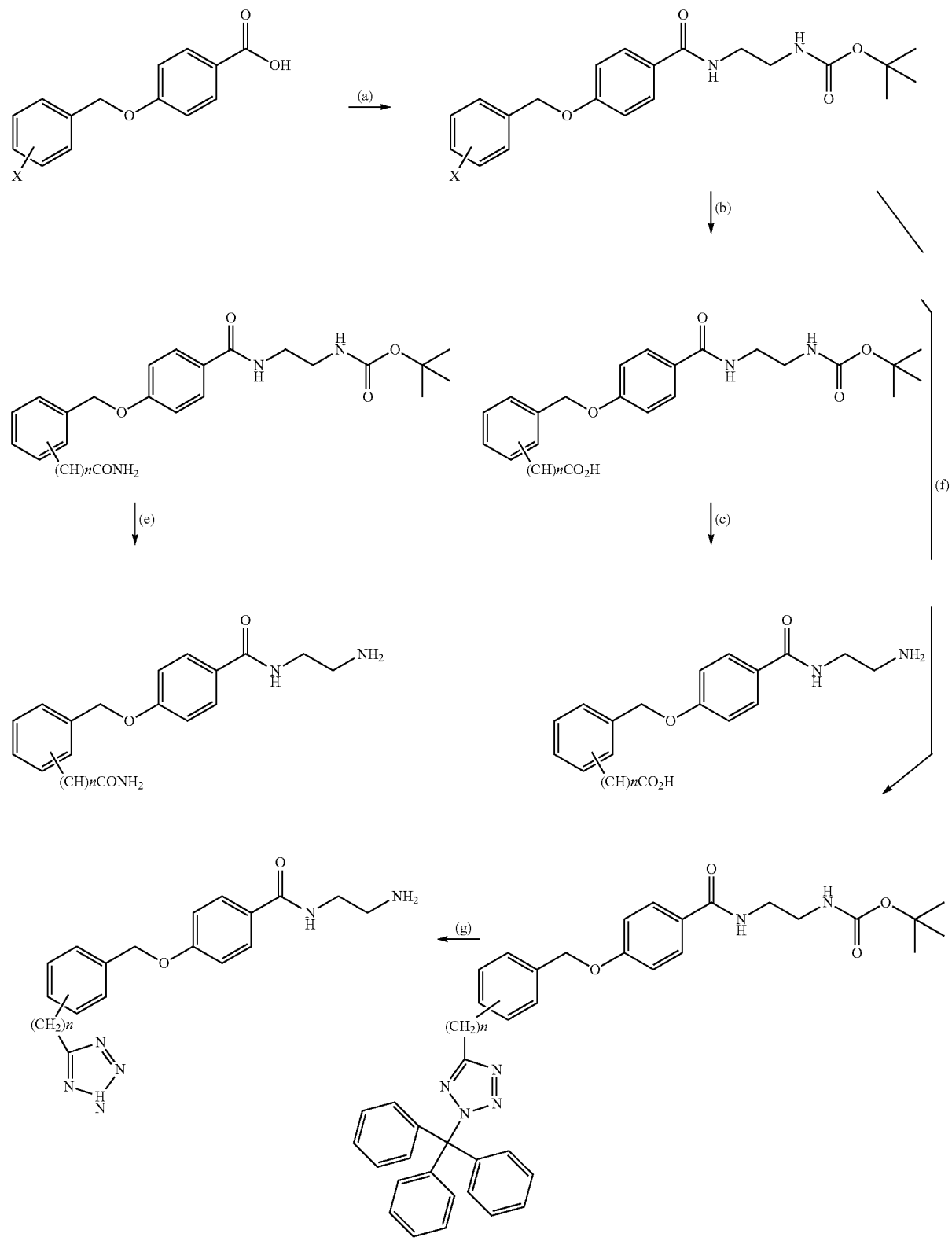
n = 0, 1, 2

Alternatively as shown in Scheme 3, a substituted benzyloxyacetic acid can be treated with ethyl chloroformate in an appropriate solvent such as methylene chloride in the presence of triethylamine, and the mixed anhydride that should form can be reacted with t-butyl(2-aminoethyl)carbamate to afford the benzamide derivative (step a). If this benzyloxy-substituent possesses an ester functionality, it can be hydrolyzed with lithium hydroxide in aqueous THF to give the acid (step b). Removal of the t-BOC group using TFA in methylene chloride should produce the amino acid (step c). If this benzyloxy-substituent possesses a nitrile group it can hydrated using aqueous hydrogen peroxide in DMSO in the presence of a base such as potassium carbonate to give the carboxamido group (step d). Removal of the t-BOC group using TFA in methylene chloride should produce the amino carboxamides (step e). A nitrile-substituted benzyloxy compound can also be treated with sodium azide and trioctyl tin chloride in xylene at elevated temperatures to give the tetrazole derivative which can be immediately reacted with trityl chloride in sodium hydroxide solution to afford the tritylated tetrazole (step f). Removal of the trityl group using aqueous hydrochloric acid in THF at about 20-30° C. can be followed by removal of the t-BOC group using TFA in methylene chloride to produce the amino tetrazole (step g).

As illustrated in Scheme 4, a nitrobenzoic acid can be treated with ethyl chloroformate in an appropriate solvent such as methylene chloride in the presence of triethylamine and the mixed anhydride that should form can be reacted with t-butyl(2-aminoethyl)carbamate to afford the benzamide derivative (step a). The nitrobenzene derivative can be reduced with Pd/C in the presence of ammonium formate in methanol solution to yield the aniline derivative (step b). Reductive amination of the aniline with a benzaldehyde using sodium triacetoxyborohydride and acetic acid in dichoroethane at about ambient temperature will give the benzyl amine derivative (step c) Removal of the t-BOC group using TFA in methylene chloride should produce the aminoamide (step d). Alternatively, the aniline can be treated with a biphenylbenzaldehyde using conditions described above to afford the phenylbenzylamine derivative (step e). Removal of the t-BOC group using TFA in methylene chloride should produce the aminoamide (step f). If either the phenyl- or biphenyl-amine contains substituents such as esters or nitriles, or alkylidene or oxaklylidene derivatives thereof, the corresponding acids, carboxamides, or tetrazoles can be prepared as described in Scheme 3 above.

Scheme 4

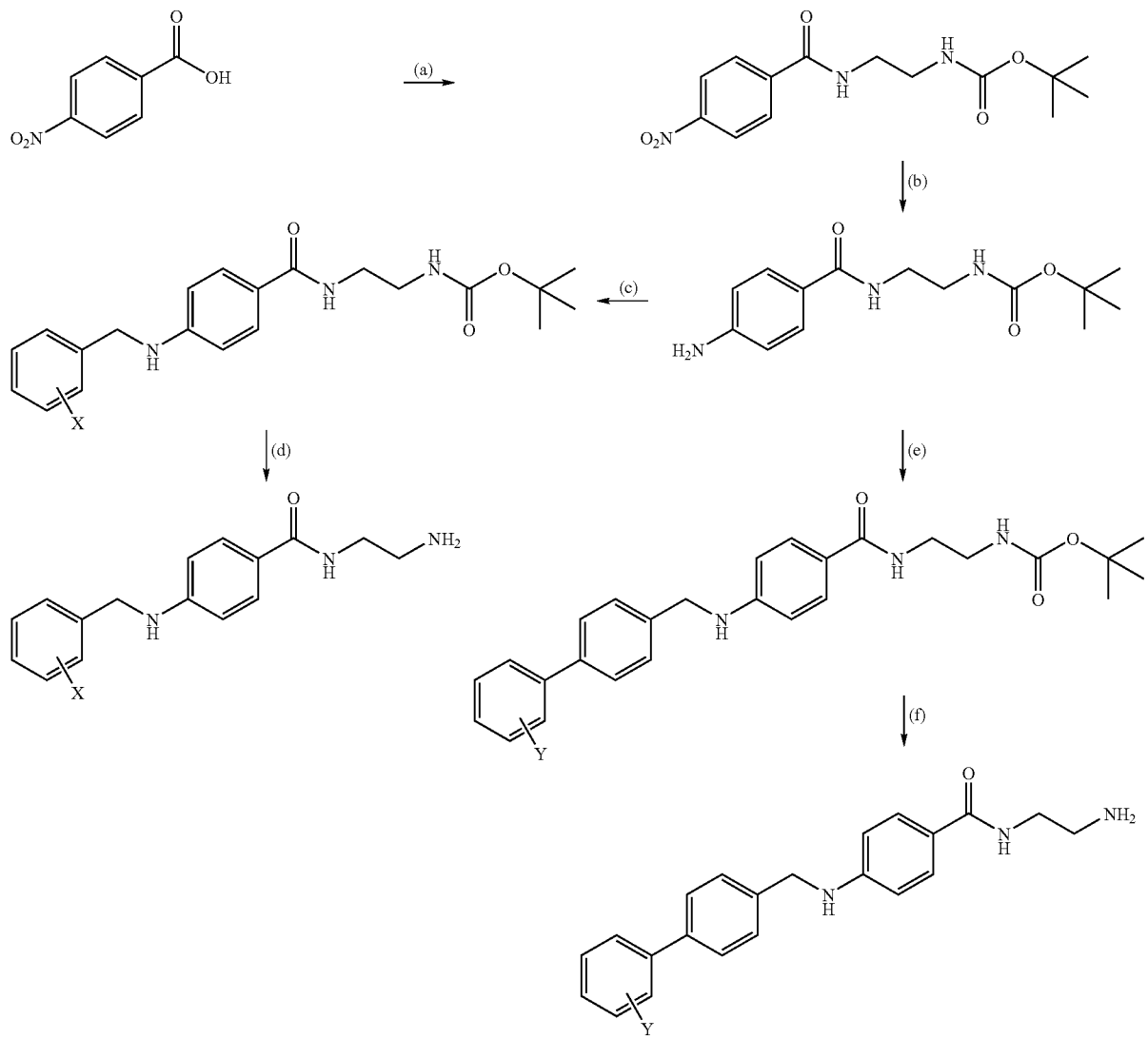

Scheme 5

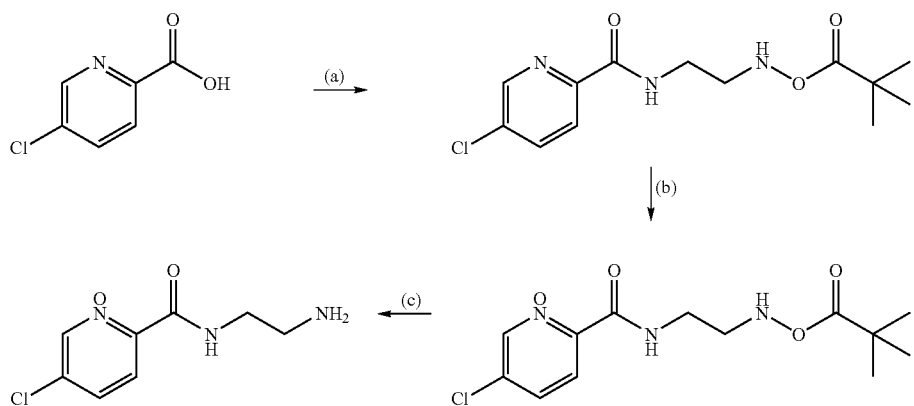

Scheme 5 depicts how 4-chloro-2-pyridinecarboxylic acid can be treated with ethyl chloroformate in an appropriate solvent such as methylene chloride in the presence of triethylamine and the mixed anhydride thus formed can be reacted with t-butyl (2-aminoethyl)carbamate to afford the chloropyridine derivative (step a). Treatment of the pyridine carboxamido compound with a peracid should give the pyridine N-oxide (step b), and subsequent removal of the t-BOC group with TFA in methylene chloride solution should afford the aminoethylbenzamide derivative (step c).

Scheme 6

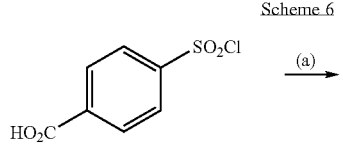

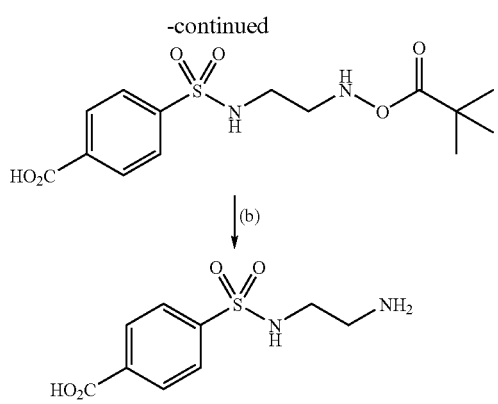

As indicated in Scheme 6, 4-chlorosulfonylbenzoic acid or alkylidene analogs thereof can be treated with t-butyl(2-aminoethyl)carbamate to give the benzene sulfonamide derivative (step a), and subsequent removal of the t-BOC group with TFA in methylene chloride solution should afford the aminoethylbenzenesulfonamide derivative (step c).

Scheme 7

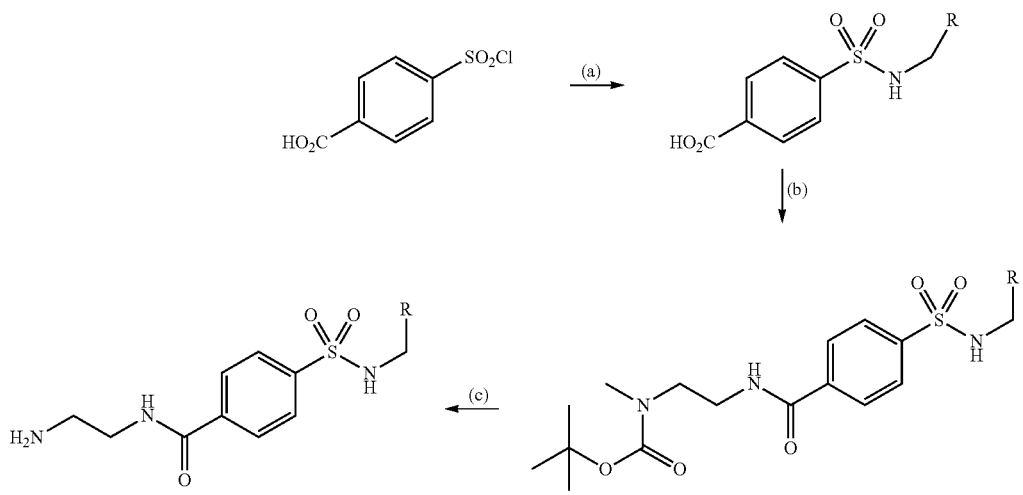

R = H, alkyl, phenyl, substituted-phenyl, heteroaryl

As noted in Scheme 7, 4-chlorosulfonylbenzoic acid or alkylidene analogs thereof can be treated with an alkylamine or a benzyl amine to give the benzene sulfonamide derivative (step a). Treatment of this acid with ethyl chloroformate in an appropriate solvent such as methylene chloride in the presence of triethylamine and the mixed anhydride thus formed can be reacted with t-butyl(2-aminoethyl)carbamate to afford the benzamide derivative (step b). Subsequent removal of the t-BOC group with TFA in methylene chloride solution should afford the aminoethylbenzamide derivative (step c).

Scheme 8

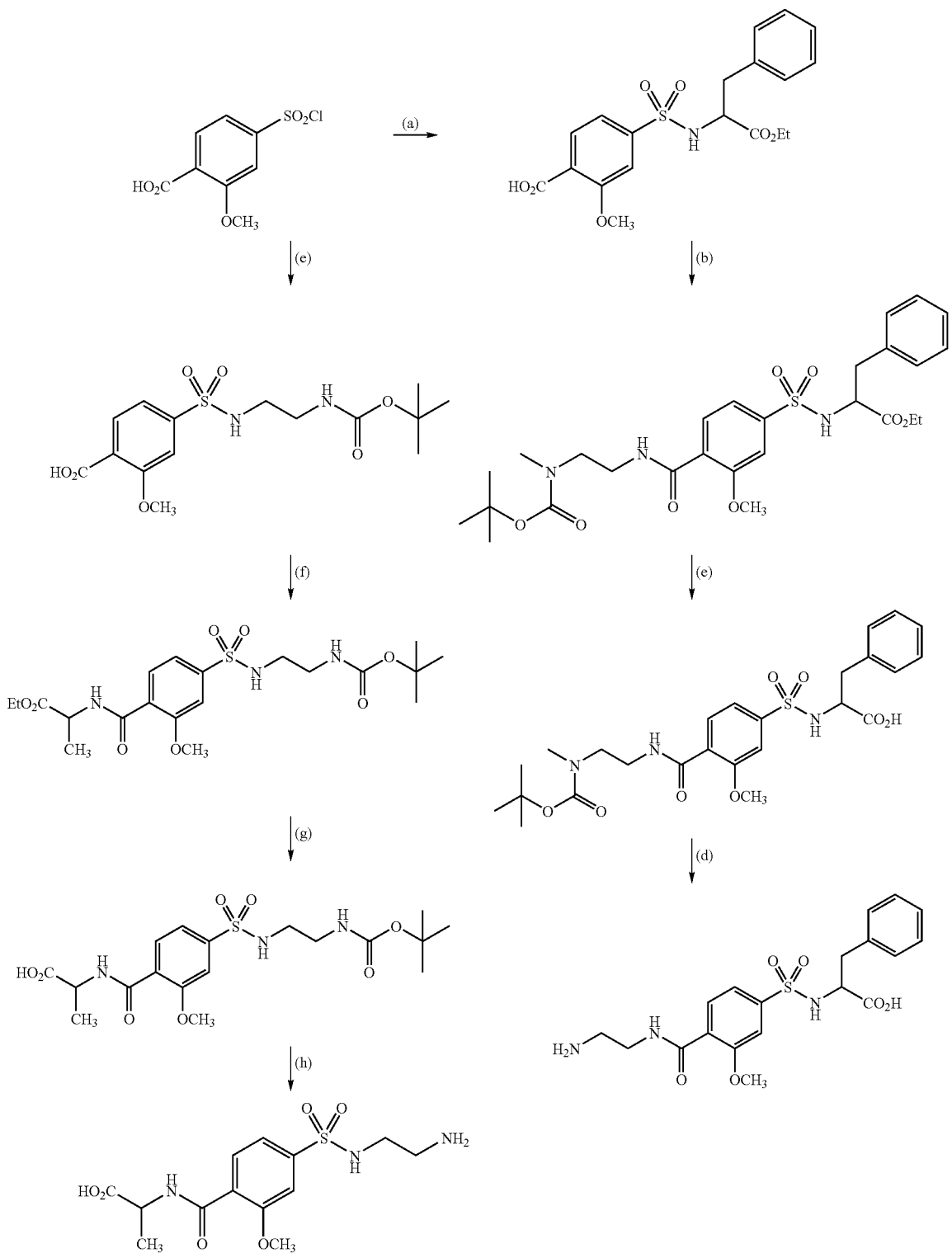

Scheme 8 describes how 4-chlorosulfony-3-methoxylbenzoic acid can be treated with phenylalanine ethyl ester in the presence of triethylamine to give the benzene sulfonamide derivative (step a). Treatment of this acid with ethyl chloroformate in an appropriate solvent such as methylene chloride in the presence of triethylamine and treatment of the mixed anhydride that should be formed with t-butyl(2-aminoethyl)carbamate should afford the benzamide derivative (step b). The ester can be hydrolyzed using lithium hydroxide in aqueous THF solution (step c), and subsequent removal of the t-BOC group with TFA in methylene chloride solution should afford the aminoethylbenzamide derivative (step d). Alternatively, 4-chlorosulfony-3-methoxylbenzoic acid can be treated with t-butyl(2-aminoethyl)carbamate in the presence of triethylamine to give the benzene sulfonamide derivative (step e). Formation of the mixed anhydride using ethyl chloroformate in an appropriate solvent such as methylene chloride in the presence of triethylamine, and treatment of the mixed anhydride thus formed with an amino acid ester such as alanine ethyl ester should produce the benzoylated amino ester derivative (step f). Hydrolysis of the ester using lithium hydroxide in aqueous THF solution (step g), and subsequent removal of the t-BOC group with TFA in methylene chloride solution should afford the aminoethylphenylsulfonamide derivative (step h).

As described in Scheme 9, 4-chlorosulfonyl-2-ethoxycarbonylmethoxy-benzoic acid can be treated with methyl amine in the presence of triethylamine to give the benzene sulfonamide derivative (step a). Treatment of this acid with ethyl chloroformate in an appropriate solvent such as methylene chloride in the presence of triethylamine and exposure of the mixed anhydride thus formed to t-butyl(2-aminoethyl)carbamate should afford the benzamide derivative (step b). The ester can be hydrolyzed using lithium hydroxide in aqueous THF solution (step c), and subsequent removal of the t-BOC group with TFA in methylene chloride solution should afford the aminoethylbenzamide derivative (step d).

Scheme 10

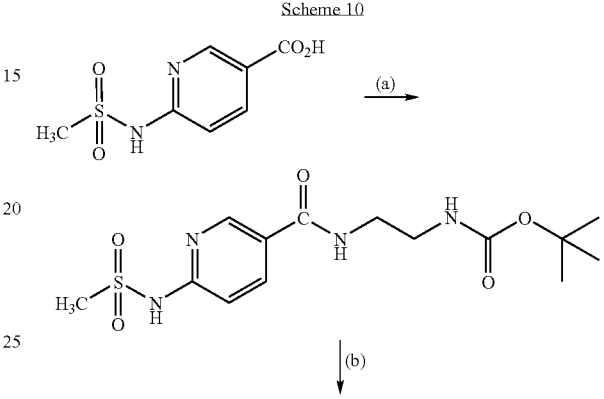

Scheme 9

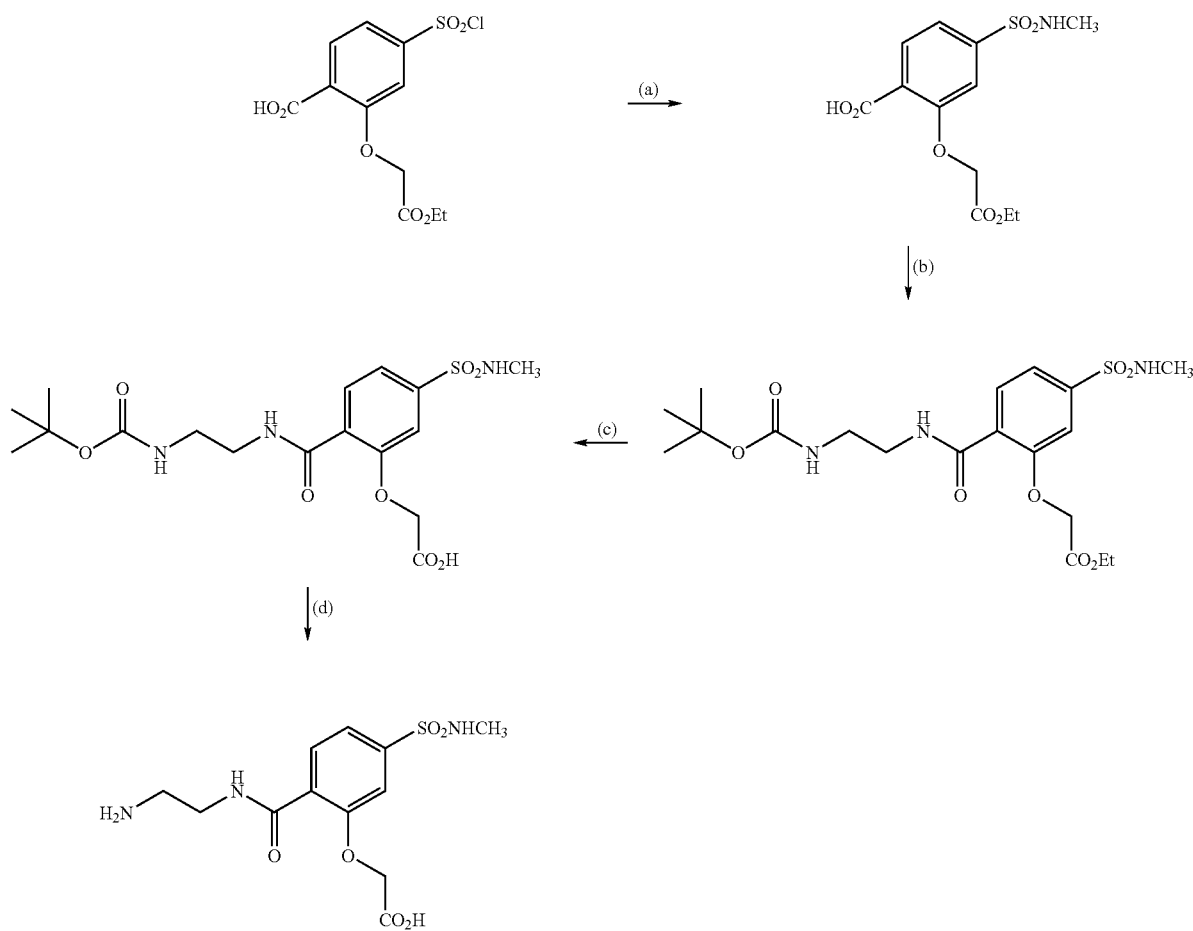

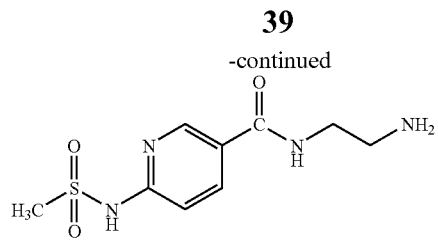

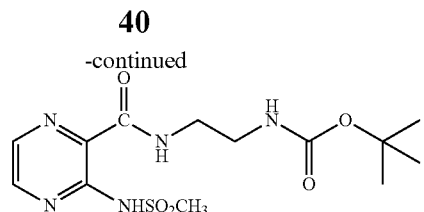

Scheme 10 shows 6-methylsulfonamidonicotinic acid can be treated with ethyl chloroformate in an appropriate solvent such as methylene chloride in the presence of triethylamine and the mixed anhydride thus formed can be reacted with t-butyl(2-aminoethyl)carbamate to afford the substituted pyridyl-carboxamido derivative (step a). Subsequent removal of the t-BOC group with TFA in methylene chloride solution should afford the aminoethylnicotinamide derivative (step b).

Scheme 11

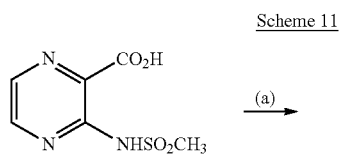

As shown in Scheme 11, 3-methylsulfonamido-2-pyrazine carboxylic acid can be treated with ethyl chloroformate in an appropriate solvent such as methylene chloride in the presence of triethylamine and the mixed anhydride thus formed can be reacted with t-butyl(2-aminoethyl)carbamate to afford the substituted pyrazinecarboxamido derivative (step a). Subsequent removal of the t-BOC group with TFA in methylene chloride solution should afford the aminoethylpyrazinecarboxamide derivative (step b).

Scheme 12

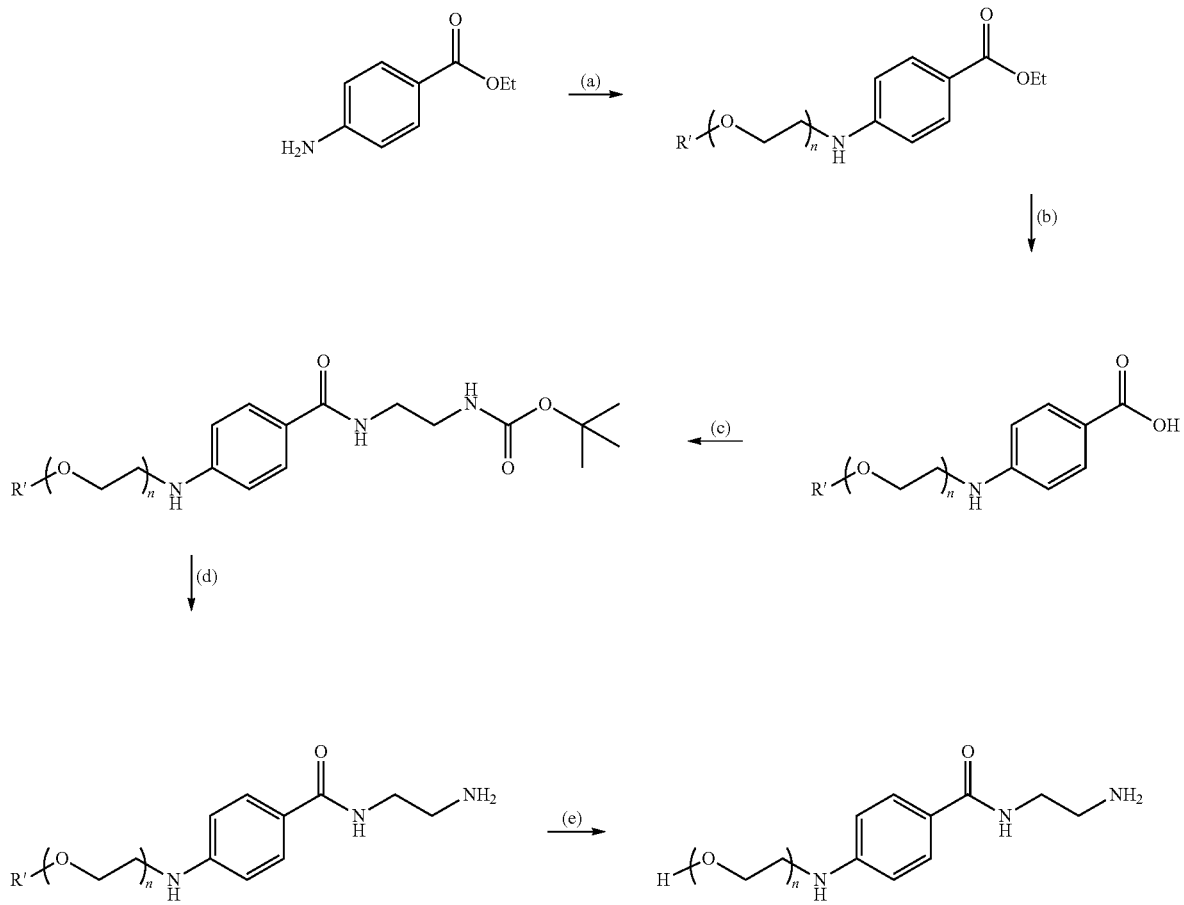

R' = TBDMS, alkyl, aralkyl

Scheme 12 depicts how monoalkylation of ethyl 4-aminobenzoate with a halo-polyethylene glycol (PEG), optionally substituted with a terminal t-butyldimethylsilyl (TBDMS), alkyl, benzyl or aralkyl group, in DMF in the presence of potassium carbonate at 60-100 degrees C. with stirring for 12-24 hours will afford the PEG anilino ester (step a). Hydrolysis of the ester using lithium hydroxide in aqueous DMF will afford the acid (step b). Treatment of the acid with ethyl chloroformate in an appropriate solvent such as methylene chloride in the presence of triethylamine will produce the mixed anhydride that will react with t-butyl(2-aminoethyl)carbamate to afford the benzamide derivative (step c). Subsequent removal of the t-BOC group with TFA in methylene chloride solution should afford the aminoethylbenzamide derivative (step d). In the case where R' is t-butyldimethylsilyl, further treatment with tetrabutylammonium fluoride in THF will give the PEG pendants with terminal hydroxyl groups (step e). The various PEG-halides can be prepared by procedures described in Nuclear Medicine and Biology, 32, 799 (2005), or are commercially available.

mide derivative (step d). In the case where R' is t-butyldimethylsilyl, further treatment with tetrabutylammonium fluoride in THF will give the PEG pendants with terminal hydroxyl groups (step e). The various PEG-halides can be prepared by procedures described in Nuclear Medicine and Biology, 32, 799 (2005), or are commercially available.

One stereoisomer of a compound of the present invention may be a more potent MAO-B inhibitor than its counterpart(s). Thus, stereoisomers are included in the present invention. Some of these stereoisomers are shown below in Scheme 14. When required, separation of the racemic material can be achieved by HPLC using a chiral column or by a resolution using a resolving agent such as described in Wilen, S. H. *Tables of Resolving Agents and Optical Resolutions* 1972, 308 or using enantiomerically pure acids and bases. A chiral compound of the present invention may also be directly synthesized using a chiral catalyst or a chiral ligand, e.g., Jacobsen, E. *Acc. Chem. Res.* 2000, 33, 421-431 or using other enantio- and diastereo-selective reactions and reagents known to one skilled in the art of asymmetric synthesis.

Scheme 13

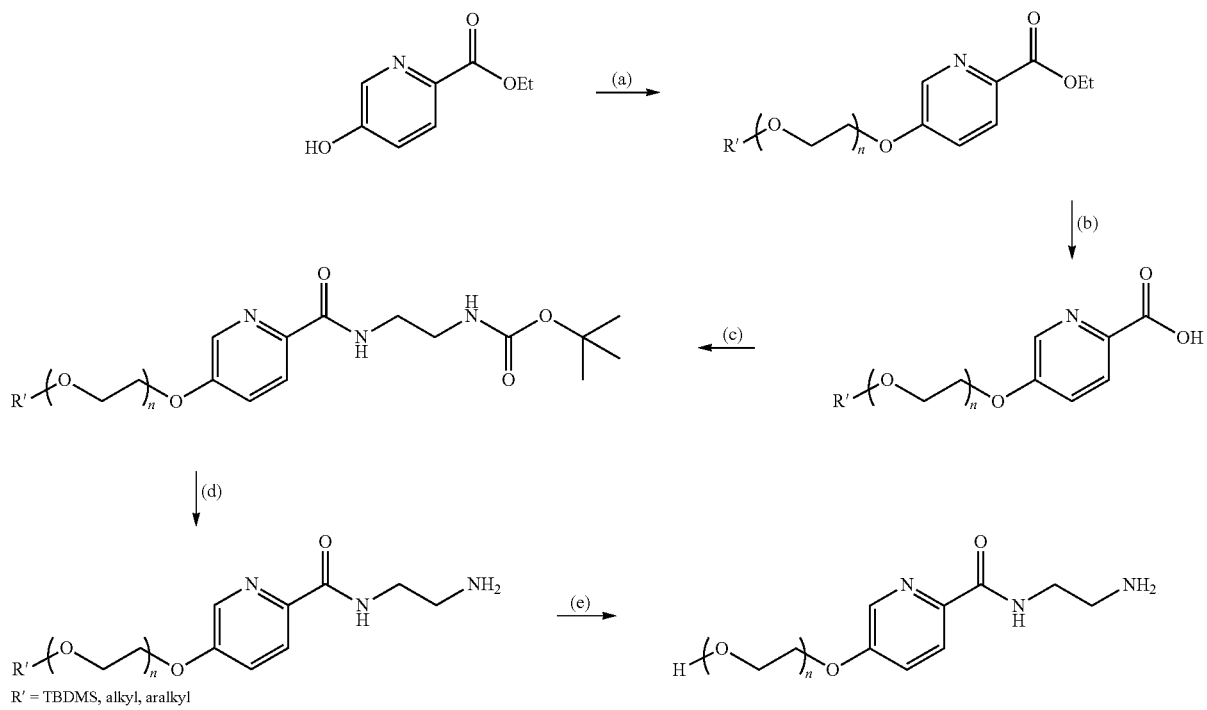

As illustrated in Scheme 13, alkylation of ethyl 5-hydroxypicolinate with a halo-polyethylene glycol (PEG), optionally substituted with a terminal t-butyldimethylsilyl (TBDMS), alkyl, benzyl or aralkyl group, in DMF in the presence of potassium carbonate at 60-100 degrees C. with stirring for 12-24 hours will afford the PEG-ether picolinate ester (step a). Hydrolysis of the ester using lithium hydroxide in aqueous DMF will afford the acid (step b). Treatment of the acid with ethyl chloroformate in an appropriate solvent such as methylene chloride in the presence of triethylamine will produce the mixed anhydride that will react with t-butyl(2-aminoethyl)carbamate to afford the benzamide derivative (step c). Subsequent removal of the t-BOC group with TFA in methylene chloride solution should afford the aminoethylbenza- Scheme 14

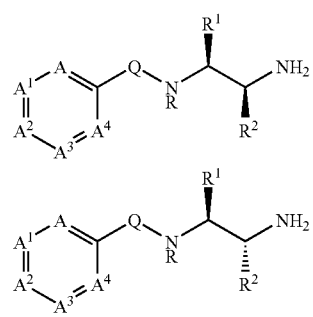

-continued

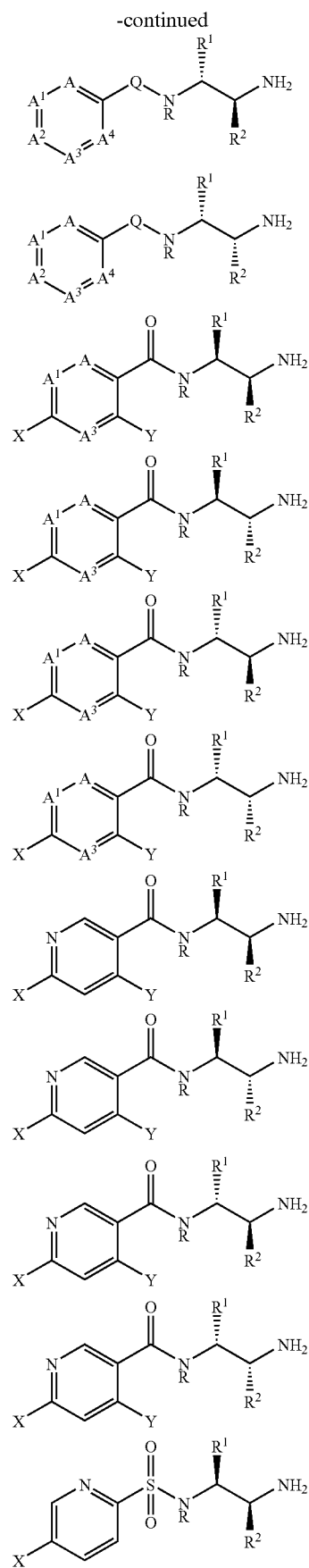

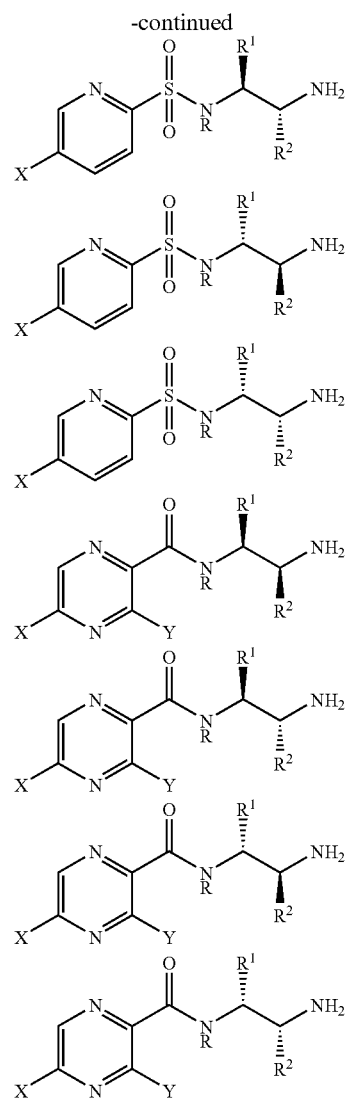

Other features of the invention will become apparent in the course of the following descriptions of exemplary embodiments that are given for illustration of the invention and are not intended to be limiting thereof.

EXAMPLES

Tables I-XIV show representative examples of the compounds of the present invention. Each example in each table represents an individual species of the present invention.

TABLE I

| Ex. # | X | Y | A | $A^1$ | $A^3$ |
|---|---|---|---|---|---|
| 1 | $CO_2Et$ | H | CH | CH | CH |
| 2 | $CO_2H$ | H | CH | CH | CH |
| 3 | $SO_3Et$ | H | CH | CH | CH |

TABLE I-continued

Structure: benzamide with A, A¹, A³ ring positions, X and Y substituents, -C(O)NH-CH₂CH₂-NH₂ group

| Ex. # | X | Y | A | A¹ | A³ |
|---|---|---|---|---|---|
| 4 | SO₃H | H | CH | CH | CH |
| 5 | PO(OEt)₂ | H | CH | CH | CH |
| 6 | PO(OH)₂ | H | CH | CH | CH |
| 7 | NHCH₂CO₂Et | H | CH | CH | CH |
| 8 | NHCH₂CO₂H | H | CH | CH | CH |
| 9 | OCH₂CO₂Et | H | CH | CH | CH |
| 10 | OCH₂CO₂H | H | CH | CH | CH |
| 11 | NHCH₂CH₂CO₂Et | H | CH | CH | CH |
| 12 | NHCH₂CH₂CO₂H | H | CH | CH | CH |
| 13 | OCH₂CH₂CO₂Et | H | CH | CH | CH |
| 14 | OCH₂CH₂CO₂H | H | CH | CH | CH |
| 15 | NHCH₂CH=CHCO₂Et | H | CH | CH | CH |
| 16 | NHCH₂CH=CHCO₂H | H | CH | CH | CH |
| 17 | OCH₂CH=CHCO₂Et | H | CH | CH | CH |
| 18 | OCH₂CH=CHCO₂H | H | CH | CH | CH |
| 19 | OCH₂CH₂PO(OEt)₂ | H | CH | CH | CH |
| 20 | OCH₂CH₂PO(OH)₂ | H | CH | CH | CH |
| 21 | OCH₂CH₂N(CH₃)₂ | H | CH | CH | CH |
| 22 | OCH₂CH₂N⁺(CH₃)₃ Cl⁻ | H | CH | CH | CH |
| 23 | SO₂NHEt | H | CH | CH | CH |
| 24 | CONHCH(CH₃)CO₂Et | H | CH | CH | CH |
| 25 | CONHCH(CH₃)CO₂H | H | CH | CH | CH |
| 26 | CONHCH(CH₂C₆H₅)CO₂Et | H | CH | CH | CH |
| 27 | CONHCH(CH₂C₆H₅)CO₂H | H | CH | CH | CH |
| 28 | NHCH₂CONH₂ | H | CH | CH | CH |
| 29 | NHCH₂CH₂CONH₂ | H | CH | CH | CH |
| 30 | OCH₂CONH₂ | H | CH | CH | CH |
| 31 | OCH₂CH₂CONH₂ | H | CH | CH | CH |
| 32 | OCH₂CH₂-tetrazole | H | CH | CH | CH |

TABLE II

| Ex. # | X | Y | A | A¹ | A³ |
|---|---|---|---|---|---|
| 1 | CO₂Et | OCH₃ | CH | CH | CH |
| 2 | CO₂H | OCH₃ | CH | CH | CH |
| 3 | SO₃Et | OCH₃ | CH | CH | CH |
| 4 | SO₃H | OCH₃ | CH | CH | CH |
| 5 | PO(OEt)₂ | OCH₃ | CH | CH | CH |
| 6 | PO(OH)₂ | OCH₃ | CH | CH | CH |
| 7 | NHCH₂CO₂Et | OCH₃ | CH | CH | CH |
| 8 | NHCH₂CO₂H | OCH₃ | CH | CH | CH |
| 9 | OCH₂CO₂Et | OCH₃ | CH | CH | CH |
| 10 | OCH₂CO₂H | OCH₃ | CH | CH | CH |
| 11 | NHCH₂CH₂CO₂Et | OCH₃ | CH | CH | CH |
| 12 | NHCH₂CH₂CO₂H | OCH₃ | CH | CH | CH |
| 13 | OCH₂CH₂CO₂Et | OCH₃ | CH | CH | CH |
| 14 | OCH₂CH₂CO₂H | OCH₃ | CH | CH | CH |
| 15 | NHCH₂CH=CHCO₂Et | OCH₃ | CH | CH | CH |
| 16 | NHCH₂CH=CHCO₂H | OCH₃ | CH | CH | CH |
| 17 | OCH₂CH=CHCO₂Et | OCH₃ | CH | CH | CH |
| 18 | OCH₂CH=CHCO₂H | OCH₃ | CH | CH | CH |
| 19 | OCH₂CH₂PO(OEt)₂ | OCH₃ | CH | CH | CH |
| 20 | OCH₂CH₂PO(OH)₂ | OCH₃ | CH | CH | CH |
| 21 | OCH₂CH₂N(CH₃)₂ | OCH₃ | CH | CH | CH |
| 22 | OCH₂CH₂N⁺(CH₃)₃ Cl⁻ | OCH₃ | CH | CH | CH |
| 23 | SO₂NHEt | OCH₃ | CH | CH | CH |
| 24 | CONHCH(CH₃)CO₂Et | OCH₃ | CH | CH | CH |
| 25 | CONHCH(CH₃)CO₂H | OCH₃ | CH | CH | CH |
| 26 | CONHCH(CH₂C₆H₅)CO₂Et | OCH₃ | CH | CH | CH |
| 27 | CONHCH(CH₂C₆H₅)CO₂H | OCH₃ | CH | CH | CH |
| 28 | NHCH₂CONH₂ | OCH₃ | CH | CH | CH |
| 29 | NHCH₂CH₂CONH₂ | OCH₃ | CH | CH | CH |
| 30 | OCH₂CONH₂ | OCH₃ | CH | CH | CH |
| 31 | OCH₂CH₂CONH₂ | OCH₃ | CH | CH | CH |
| 32 | OCH₂CH₂-tetrazole | OCH₃ | CH | CH | CH |
| 34 | OCH₂C₆H₅ | OCH₃ | CH | CH | CH |
| 35 | OCH₂C₆H₄—Cl(3) | OCH₃ | CH | CH | CH |
| 36 | OCH₂C₆H₄—Cl(4) | OCH₃ | CH | CH | CH |
| 37 | OCH₂C₆H₄—F(3) | OCH₃ | CH | CH | CH |
| 38 | OCH₂C₆H₄—F(4) | OCH₃ | CH | CH | CH |
| 39 | OCH₂C₆H₄—CF₃(3) | OCH₃ | CH | CH | CH |
| 40 | OCH₂C₆H₄—CF₃(4) | OCH₃ | CH | CH | CH |
| 41 | OCH₂C₆H₄—NO₂(3) | OCH₃ | CH | CH | CH |
| 42 | OCH₂C₆H₄—NO₂(4) | OCH₃ | CH | CH | CH |
| 43 | OCH₂C₆H₄—CH₃(3) | OCH₃ | CH | CH | CH |
| 44 | OCH₂C₆H₄—CH₃(4) | OCH₃ | CH | CH | CH |
| 45 | OCH₂C₆H₄—OCH₃(3) | OCH₃ | CH | CH | CH |
| 46 | OCH₂C₆H₄—OCH₃(4) | OCH₃ | CH | CH | CH |
| 47 | OCH₂C₆H₄—NHSO₂CH₃(3) | OCH₃ | CH | CH | CH |
| 48 | OCH₂C₆H₄—NHSO₂CH₃(4) | OCH₃ | CH | CH | CH |
| 49 | OCH₂C₆H₄—CN(3) | OCH₃ | CH | CH | CH |
| 50 | OCH₂C₆H₄—CN(4) | OCH₃ | CH | CH | CH |
| 51 | OCH₂C₆H₄—CONH₂(3) | OCH₃ | CH | CH | CH |
| 52 | OCH₂C₆H₄—CONH₂(4) | OCH₃ | CH | CH | CH |
| 53 | OCH₂C₆H₄—OCH₂CN(3) | OCH₃ | CH | CH | CH |
| 54 | OCH₂C₆H₄—OCH₂CN(4) | OCH₃ | CH | CH | CH |
| 55 | OCH₂C₆H₄—OCH₂CONH₂(3) | OCH₃ | CH | CH | CH |
| 56 | OCH₂C₆H₄—OCH₂CONH₂(4) | OCH₃ | CH | CH | CH |
| 57 | OCH₂C₆H₄CH₂CN(3) | OCH₃ | CH | CH | CH |
| 58 | OCH₂C₆H₄CH₂CN(4) | OCH₃ | CH | CH | CH |
| 59 | OCH₂C₆H₄CH₂CONH₂(3) | OCH₃ | CH | CH | CH |
| 60 | OCH₂C₆H₄CH₂CONH₂(4) | OCH₃ | CH | CH | CH |
| 61 | OCH₂C₆H₃(CN)₂(3,5) | OCH₃ | CH | CH | CH |
| 62 | OCH₂C₆H₃(CN)₂(3,5) | OCH₃ | CH | CH | CH |
| 63 | OCH₂C₆H₃(CONH₂)₂(3,5) | OCH₃ | CH | CH | CH |
| 64 | OCH₂C₆H₃(CONH₂)₂(3,5) | OCH₃ | CH | CH | CH |
| 65 | OCH₂C₆H₄C₆H₄CN(2, 3, or 4) | OCH₃ | CH | CH | CH |
| 66 | OCH₂C₆H₄C₆H₄CONH₂(2, 3, or 4) | OCH₃ | CH | CH | CH |

TABLE III

| Ex. # | X | Y | A | A¹ | A³ |
|---|---|---|---|---|---|
| 1. | SO₂NHEt | OCH₂CO₂Et | CH | CH | CH |
| 2. | NHCH₂CONH₂ | OCH₂CO₂Et | CH | CH | CH |
| 3. | SO₂NHCH₂C₆H₅ | OCH₂CO₂Et | CH | CH | CH |
| 4. | SO₂NHC₆H₅ | OCH₂CO₂Et | CH | CH | CH |
| 5. | SO₂NHEt | OCH₂CO₂H | CH | CH | CH |

TABLE III-continued

![Structure: benzamide with X, Y, A, A¹, A³ substituents linked to NHCH₂CH₂NH₂]

| Ex. # | X | Y | A | A¹ | A³ |
|---|---|---|---|---|---|
| 6. | NHCH₂CONH₂ | OCH₂CO₂H | CH | CH | CH |
| 7. | SO₂NHCH₂C₆H₅ | OCH₂CO₂H | CH | CH | CH |
| 8. | SO₂NHC₆H₅ | OCH₂CO₂H | CH | CH | CH |
| 9. | H | OCH₂CO₂Et | CH | CH | CH |
| 10. | H | OCH₂CO₂H | CH | CH | CH |

TABLE IV

| Ex. # | X | Y | A | A¹ | A³ |
|---|---|---|---|---|---|
| 1 | CO₂Et | H | N | CH | CH |
| 2 | CO₂H | H | N | CH | CH |
| 3 | SO₃Et | H | N | CH | CH |
| 4 | SO₃H | H | N | CH | CH |
| 5 | PO(OEt)₂ | H | N | CH | CH |
| 6 | PO(OH)₂ | H | N | CH | CH |
| 7 | NHCH₂CO₂Et | H | N | CH | CH |
| 8 | NHCH₂CO₂H | H | N | CH | CH |
| 9 | OCH₂CO₂Et | H | N | CH | CH |
| 10 | OCH₂CO₂H | H | N | CH | CH |
| 11 | NHCH₂CH₂CO₂Et | H | N | CH | CH |
| 12 | NHCH₂CH₂CO₂H | H | N | CH | CH |
| 13 | OCH₂CH₂CO₂Et | H | N | CH | CH |
| 14 | OCH₂CH₂CO₂H | H | N | CH | CH |
| 15 | NHCH₂CH=CHCO₂Et | H | N | CH | CH |
| 16 | NHCH₂CH=CHCO₂H | H | N | CH | CH |
| 17 | OCH₂CH=CHCO₂Et | H | N | CH | CH |
| 18 | OCH₂CH=CHCO₂H | H | N | CH | CH |
| 19 | OCH₂CH₂PO(OEt)₂ | H | N | CH | CH |
| 20 | OCH₂CH₂PO(OH)₂ | H | N | CH | CH |
| 21 | OCH₂CH₂N(CH₃)₂ | H | N | CH | CH |
| 22 | OCH₂CH₂N⁺(CH₃)₃ Cl⁻ | H | N | CH | CH |
| 23 | SO₂NHEt | H | N | CH | CH |
| 24 | CONHCH(CH₃)CO₂Et | H | N | CH | CH |
| 25 | CONHCH(CH₃)CO₂H | H | N | CH | CH |
| 26 | CONHCH(CH₂C₆H₅)CO₂Et | H | N | CH | CH |
| 27 | CONHCH(CH₂C₆H₅)CO₂H | H | N | CH | CH |
| 28 | NHCH₂CONH₂ | H | N | CH | CH |
| 29 | NHCH₂CH₂CONH₂ | H | N | CH | CH |
| 30 | OCH₂CONH₂ | H | N | CH | CH |
| 31 | OCH₂CH₂CONH₂ | H | N | CH | CH |
| 32 | OCH₂CH₂-tetrazole | H | N | CH | CH |

TABLE V

| Ex. # | X | Y | A | A¹ | A³ |
|---|---|---|---|---|---|
| 1 | CO₂Et | H | CH | N | CH |
| 2 | CO₂H | H | CH | N | CH |
| 3 | SO₃Et | H | CH | N | CH |
| 4 | SO₃H | H | CH | N | CH |
| 5 | PO(OEt)₂ | H | CH | N | CH |
| 6 | PO(OH)₂ | H | CH | N | CH |
| 7 | NHCH₂CO₂Et | H | CH | N | CH |
| 8 | NHCH₂CO₂H | H | CH | N | CH |
| 9 | OCH₂CO₂Et | H | CH | N | CH |
| 10 | OCH₂CO₂H | H | CH | N | CH |
| 11 | NHCH₂CH₂CO₂Et | H | CH | N | CH |
| 12 | NHCH₂CH₂CO₂H | H | CH | N | CH |
| 13 | OCH₂CH₂CO₂Et | H | CH | N | CH |
| 14 | OCH₂CH₂CO₂H | H | CH | N | CH |
| 15 | NHCH₂CH=CHCO₂Et | H | CH | N | CH |
| 16 | NHCH₂CH=CHCO₂H | H | CH | N | CH |
| 17 | OCH₂CH=CHCO₂Et | H | CH | N | CH |
| 18 | OCH₂CH=CHCO₂H | H | CH | N | CH |
| 19 | OCH₂CH₂PO(OEt)₂ | H | CH | N | CH |
| 20 | OCH₂CH₂PO(OH)₂ | H | CH | N | CH |
| 21 | OCH₂CH₂N(CH₃)₂ | H | CH | N | CH |
| 22 | OCH₂CH₂N⁺(CH₃)₃ Cl⁻ | H | CH | N | CH |
| 23 | SO₂NHEt | H | CH | N | CH |
| 24 | CONHCH(CH₃)CO₂Et | H | CH | N | CH |
| 25 | CONHCH(CH₃)CO₂H | H | CH | N | CH |
| 26 | CONHCH(CH₂C₆H₅)CO₂Et | H | CH | N | CH |
| 27 | CONHCH(CH₂C₆H₅)CO₂H | H | CH | N | CH |
| 28 | NHCH₂CONH₂ | H | CH | N | CH |
| 29 | NHCH₂CH₂CONH₂ | H | CH | N | CH |
| 30 | OCH₂CONH₂ | H | CH | N | CH |
| 31 | OCH₂CH₂CONH₂ | H | CH | N | CH |
| 32 | OCH₂CH₂-tetrazole | H | CH | N | CH |
| 33 | OCH₂CH₂C₆H₅ | H | CH | N | CH |
| 34 | OCH₂C₆H₅ | H | CH | N | CH |
| 35 | OCH₂C₆H₄—Cl(3) | H | CH | N | CH |
| 36 | OCH₂C₆H₄—Cl(4) | H | CH | N | CH |
| 37 | OCH₂C₆H₄—F(3) | H | CH | N | CH |
| 38 | OCH₂C₆H₄—F(4) | H | CH | N | CH |
| 39 | OCH₂C₆H₄—CF₃(3) | H | CH | N | CH |
| 40 | OCH₂C₆H₄—CF₃(4) | H | CH | N | CH |
| 41 | OCH₂C₆H₄—NO₂(3) | H | CH | N | CH |
| 42 | OCH₂C₆H₄—NO₂(4) | H | CH | N | CH |
| 43 | OCH₂C₆H₄—CH₃(3) | H | CH | N | CH |
| 44 | OCH₂C₆H₄—CH₃(4) | H | CH | N | CH |
| 45 | OCH₂C₆H₄—OCH₃(3) | H | CH | N | CH |
| 46 | OCH₂C₆H₄—OCH₃(4) | H | CH | N | CH |
| 47 | OCH₂C₆H₄—NHSO₂CH₃(3) | H | CH | N | CH |
| 48 | OCH₂C₆H₄—NHSO₂CH₃(4) | H | CH | N | CH |
| 49 | OCH₂C₆H₄—CN(3) | H | CH | N | CH |
| 50 | OCH₂C₆H₄—CN(4) | H | CH | N | CH |
| 51 | OCH₂C₆H₄—CONH₂(3) | H | CH | N | CH |
| 52 | OCH₂C₆H₄—CONH₂(4) | H | CH | N | CH |
| 53 | OCH₂C₆H₄—OCH₂CN(3) | H | CH | N | CH |
| 54 | OCH₂C₆H₄—OCH₂CN(4) | H | CH | N | CH |
| 55 | OCH₂C₆H₄—OCH₂CONH₂(3) | H | CH | N | CH |
| 56 | OCH₂C₆H₄—OCH₂CONH₂(4) | H | CH | N | CH |
| 57 | OCH₂C₆H₄CH₂CN(3) | H | CH | N | CH |
| 58 | OCH₂C₆H₄CH₂CN(4) | H | CH | N | CH |
| 59 | OCH₂C₆H₄CH₂CONH₂(3) | H | CH | N | CH |
| 60 | OCH₂C₆H₄CH₂CONH₂(4) | H | CH | N | CH |
| 61 | OCH₂C₆H₃(CN)₂(3,5) | H | CH | N | CH |
| 62 | OCH₂C₆H₃(CN)₂(3,5) | H | CH | N | CH |
| 63 | OCH₂C₆H₃(CONH₂)₂(3,5) | H | CH | N | CH |
| 64 | OCH₂C₆H₃(CONH₂)₂(3,5) | H | CH | N | CH |
| 65 | OCH₂C₆H₄C₆H₄CN(2, 3, or 4) | H | CH | N | CH |
| 66 | OCH₂C₆H₄C₆H₄CONH₂(2, 3, or 4) | H | CH | N | CH |

TABLE VI

| Ex. # | X | Y | A | A¹ | A³ |
|---|---|---|---|---|---|
| 1 | CO$_2$Et | H | N | CH | N |
| 2 | CO$_2$H | H | N | CH | N |
| 3 | SO$_3$Et | H | N | CH | N |
| 4 | SO$_3$H | H | N | CH | N |
| 5 | PO(OEt)$_2$ | H | N | CH | N |
| 6 | PO(OH)$_2$ | H | N | CH | N |
| 7 | NHCH$_2$CO$_2$Et | H | N | CH | N |
| 8 | NHCH$_2$CO$_2$H | H | N | CH | N |
| 9 | OCH$_2$CO$_2$Et | H | N | CH | N |
| 10 | OCH$_2$CO$_2$H | H | N | CH | N |
| 11 | NHCH$_2$CH$_2$CO$_2$Et | H | N | CH | N |
| 12 | NHCH$_2$CH$_2$CO$_2$H | H | N | CH | N |
| 13 | OCH$_2$CH$_2$CO$_2$Et | H | N | CH | N |
| 14 | OCH$_2$CH$_2$CO$_2$H | H | N | CH | N |
| 15 | NHCH$_2$CH=CHCO$_2$Et | H | N | CH | N |
| 16 | NHCH$_2$CH=CHCO$_2$H | H | N | CH | N |
| 17 | OCH$_2$CH=CHCO$_2$Et | H | N | CH | N |
| 18 | OCH$_2$CH=CHCO$_2$H | H | N | CH | N |
| 19 | OCH$_2$CH$_2$PO(OEt)$_2$ | H | N | CH | N |
| 20 | OCH$_2$CH$_2$PO(OH)$_2$ | H | N | CH | N |
| 21 | OCH$_2$CH$_2$N(CH$_3$)$_2$ | H | N | CH | N |
| 22 | OCH$_2$CH$_2$N$^+$(CH$_3$)$_3$ Cl$^-$ | H | N | CH | N |
| 23 | SO$_2$NHEt | H | N | CH | N |
| 24 | CONHCH(CH$_3$)CO$_2$Et | H | N | CH | N |
| 25 | CONHCH(CH$_3$)CO$_2$H | H | N | CH | N |
| 26 | CONHCH(CH$_2$C$_6$H$_5$)CO$_2$Et | H | N | CH | N |
| 27 | CONHCH(CH$_2$C$_6$H$_5$)CO$_2$H | H | N | CH | N |
| 28 | NHCH$_2$CONH$_2$ | H | N | CH | N |
| 29 | NHCH$_2$CH$_2$CONH$_2$ | H | N | CH | N |
| 30 | OCH$_2$CONH$_2$ | H | N | CH | N |
| 31 | OCH$_2$CH$_2$CONH$_2$ | H | N | CH | N |
| 32 | OCH$_2$CH$_2$-tetrazole | H | N | CH | N |

TABLE VII

| Ex. # | X | Y | A | A¹ | A³ |
|---|---|---|---|---|---|
| 1 | H | CO$_2$Et | N | CH | N |
| 2 | H | CO$_2$H | N | CH | N |
| 3 | H | SO$_3$Et | N | CH | N |
| 4 | H | SO$_3$H | N | CH | N |
| 5 | H | PO(OEt)$_2$ | N | CH | N |
| 6 | H | PO(OH)$_2$ | N | CH | N |
| 7 | H | NHCH$_2$CO$_2$Et | N | CH | N |
| 8 | H | NHCH$_2$CO$_2$H | N | CH | N |
| 9 | H | OCH$_2$CO$_2$Et | N | CH | N |
| 10 | H | OCH$_2$CO$_2$H | N | CH | N |
| 11 | H | NHCH$_2$CH$_2$CO$_2$Et | N | CH | N |
| 12 | H | NHCH$_2$CH$_2$CO$_2$H | N | CH | N |
| 13 | H | OCH$_2$CH$_2$CO$_2$Et | N | CH | N |
| 14 | H | OCH$_2$CH$_2$CO$_2$H | N | CH | N |
| 15 | H | NHCH$_2$CH=CHCO$_2$Et | N | CH | N |
| 16 | H | NHCH$_2$CH=CHCO$_2$H | N | CH | N |
| 17 | H | OCH$_2$CH=CHCO$_2$Et | N | CH | N |
| 18 | H | OCH$_2$CH=CHCO$_2$H | N | CH | N |
| 19 | H | OCH$_2$CH$_2$PO(OEt)$_2$ | N | CH | N |
| 20 | H | OCH$_2$CH$_2$PO(OH)$_2$ | N | CH | N |
| 21 | H | OCH$_2$CH$_2$N(CH$_3$)$_2$ | N | CH | N |
| 22 | H | OCH$_2$CH$_2$N$^+$(CH$_3$)$_3$ Cl$^-$ | N | CH | N |
| 23 | H | SO$_2$NHEt | N | CH | N |
| 24 | H | CONHCH(CH$_3$)CO$_2$Et | N | CH | N |
| 25 | H | CONHCH(CH$_3$)CO$_2$H | N | CH | N |
| 26 | H | CONHCH(CH$_2$C$_6$H$_5$)CO$_2$Et | N | CH | N |
| 27 | H | CONHCH(CH$_2$C$_6$H$_5$)CO$_2$H | N | CH | N |
| 28 | H | NHCH$_2$CONH$_2$ | N | CH | N |
| 29 | H | NHCH$_2$CH$_2$CONH$_2$ | N | CH | N |
| 30 | H | OCH$_2$CONH$_2$ | N | CH | N |
| 31 | H | OCH$_2$CH$_2$CONH$_2$ | N | CH | N |
| 32 | H | OCH$_2$CH$_2$-tetrazole | N | CH | N |

TABLE VIII

| Ex. # | X | A |
|---|---|---|
| 1 | CO$_2$Et | CH |
| 2 | CO$_2$H | CH |
| 3 | OCH$_2$CH=CHCO$_2$Et | CH |
| 4 | OCH$_2$CH=CHCO$_2$H | CH |
| 5 | NHCH$_2$CO$_2$Et | CH |
| 6 | NHCH$_2$CO$_2$H | CH |
| 7 | OCH$_2$CO$_2$Et | CH |
| 8 | OCH$_2$CO$_2$H | CH |
| 9 | NHCH$_2$CH$_2$CO$_2$Et | CH |
| 10 | NHCH$_2$CH$_2$CO$_2$H | CH |
| 11 | OCH$_2$CH$_2$CO$_2$Et | CH |
| 12 | OCH$_2$CH$_2$CO$_2$H | CH |
| 13 | NHCH$_2$CH=CHCO$_2$Et | CH |
| 14 | NHCH$_2$CH=CHCO$_2$H | CH |
| 15 | OCH$_2$CH=CHCO$_2$Et | CH |
| 16 | OCH$_2$CH=CHCO$_2$H | CH |
| 17 | OCH$_2$CH$_2$PO(OEt)$_2$ | CH |
| 18 | OCH$_2$CH$_2$PO(OH)$_2$ | CH |
| 19 | OCH$_2$CH$_2$N(CH$_3$)$_2$ | CH |
| 20 | OCH$_2$CH$_2$N$^+$(CH$_3$)$_3$ Cl$^-$ | CH |
| 21 | CONHCH(CH$_3$)CO$_2$Et | CH |
| 22 | CONHCH(CH$_3$)CO$_2$H | CH |
| 23 | CONHCH(CH$_2$C$_6$H$_5$)CO$_2$Et | CH |
| 24 | CONHCH(CH$_2$C$_6$H$_5$)CO$_2$H | CH |
| 25 | NHCH$_2$CONH$_2$ | CH |
| 26 | NHCH$_2$CH$_2$CONH$_2$ | CH |
| 27 | OCH$_2$CONH$_2$ | CH |
| 28 | OCH$_2$CH$_2$CONH$_2$ | CH |
| 29 | OCH$_2$CH$_2$-tetrazole | CH |
| 30 | OCH$_2$CH$_2$C$_6$H$_5$ | CH |
| 31 | OCH$_2$C$_6$H$_5$ | CH |
| 32 | OCH$_2$C$_6$H$_4$—Cl(3) | CH |
| 33 | OCH$_2$C$_6$H$_4$—Cl(4) | CH |
| 34 | OCH$_2$C$_6$H$_4$—F(3) | CH |
| 35 | OCH$_2$C$_6$H$_4$—F(4) | CH |
| 36 | OCH$_2$C$_6$H$_4$—CF$_3$(3) | CH |
| 37 | OCH$_2$C$_6$H$_4$—CF$_3$(4) | CH |
| 38 | OCH$_2$C$_6$H$_4$—NO$_2$(3) | CH |
| 39 | OCH$_2$C$_6$H$_4$—NO$_2$(4) | CH |
| 40 | OCH$_2$C$_6$H$_4$—CH$_3$(3) | CH |
| 41 | OCH$_2$C$_6$H$_4$—CH$_3$(4) | CH |
| 42 | OCH$_2$C$_6$H$_4$—OCH$_3$(3) | CH |
| 43 | OCH$_2$C$_6$H$_4$—OCH$_3$(4) | CH |
| 44 | OCH$_2$C$_6$H$_4$—NHSO$_2$CH$_3$(3) | CH |

TABLE VIII-continued

![sulfonamide structure with X on aryl ring, A in ring, SO2NH-CH2CH2-NH2]

| Ex. # | X | A |
|---|---|---|
| 45 | OCH₂C₆H₄—NHSO₂CH₃(4) | CH |
| 46 | OCH₂C₆H₄—CN(3) | CH |
| 47 | OCH₂C₆H₄—CN(4) | CH |
| 48 | OCH₂C₆H₄—CONH₂(3) | CH |
| 49 | OCH₂C₆H₄—CONH₂(4) | CH |
| 50 | OCH₂C₆H₄—OCH₂CN(3) | CH |
| 51 | OCH₂C₆H₄—OCH₂CN(4) | CH |
| 52 | OCH₂C₆H₄—OCH₂CONH₂(3) | CH |
| 53 | OCH₂C₆H₄—OCH₂CONH₂(4) | CH |
| 54 | OCH₂C₆H₄CH₂CN(3) | CH |
| 55 | OCH₂C₆H₄CH₂CN(4) | CH |
| 56 | OCH₂C₆H₄CH₂CONH₂(3) | CH |
| 57 | OCH₂C₆H₄CH₂CONH₂(4) | CH |
| 58 | OCH₂C₆H₃(CN)₂(3,5) | CH |
| 59 | OCH₂C₆H₃(CN)₂(3,5) | CH |
| 60 | OCH₂C₆H₃(CONH₂)₂(3,5) | CH |
| 61 | OCH₂C₆H₃(CONH₂)₂(3,5) | CH |
| 62 | OCH₂C₆H₄C₆H₄CN(2, 3, or 4) | CH |
| 63 | OCH₂C₆H₄C₆H₄CONH₂(2, 3, or 4) | CH |

TABLE IX

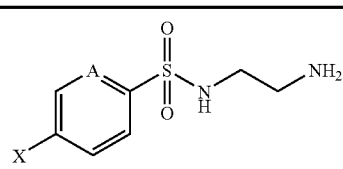

| Ex. # | X | A |
|---|---|---|
| 1 | NHCH₂CO₂Et | N |
| 2 | NHCH₂CO₂H | N |
| 3 | OCH₂CO₂Et | N |
| 4 | OCH₂CO₂H | N |
| 5 | NHCH₂CH₂CO₂Et | N |
| 6 | NHCH₂CH₂CO₂H | N |
| 7 | OCH₂CH₂CO₂Et | N |
| 8 | OCH₂CH₂CO₂H | N |
| 9 | NHCH₂CH=CHCO₂Et | N |
| 10 | NHCH₂CH=CHCO₂H | N |
| 11 | OCH₂CH=CHCO₂Et | N |
| 12 | OCH₂CH=CHCO₂H | N |
| 13 | NHCH₂CONH₂ | N |
| 14 | NHCH₂CH₂CONH₂ | N |
| 15 | OCH₂CONH₂ | N |
| 16 | OCH₂CH₂CONH₂ | N |
| 17 | OCH₂CH₂PO(OEt)₂ | N |
| 18 | OCH₂CH₂PO(OH)₂ | N |
| 19 | OCH₂CH₂N(CH₃)₂ | N |
| 20 | OCH₂CH₂N⁺(CH₃)₃ Cl⁻ | N |
| 21 | CONHCH(CH₃)CO₂Et | N |
| 22 | CONHCH(CH₃)CO₂H | N |
| 23 | CONHCH(CH₂C₆H₅)CO₂Et | N |
| 24 | CONHCH(CH₂C₆H₅)CO₂H | N |
| 25 | NHCH₂CONH₂ | N |
| 26 | NHCH₂CH₂CONH₂ | N |
| 27 | OCH₂CONH₂ | N |
| 28 | OCH₂CH₂CONH₂ | N |
| 29 | OCH₂CH₂-tetrazole | N |
| 30 | OCH₂CH₂C₆H₅ | N |
| 31 | OCH₂C₆H₅ | N |
| 32 | OCH₂C₆H₄—Cl(3) | N |
| 33 | OCH₂C₆H₄—Cl(4) | N |
| 34 | OCH₂C₆H₄—F(3) | N |
| 35 | OCH₂C₆H₄—F(4) | N |

TABLE IX-continued

| Ex. # | X | A |
|---|---|---|
| 36 | OCH₂C₆H₄—CF₃(3) | N |
| 37 | OCH₂C₆H₄—CF₃(4) | N |
| 38 | OCH₂C₆H₄—NO₂(3) | N |
| 39 | OCH₂C₆H₄—NO₂(4) | N |
| 40 | OCH₂C₆H₄—CH₃(3) | N |
| 41 | OCH₂C₆H₄—CH₃(4) | N |
| 42 | OCH₂C₆H₄—OCH₃(3) | N |
| 43 | OCH₂C₆H₄—OCH₃(4) | N |
| 44 | OCH₂C₆H₄—NHSO₂CH₃(3) | N |
| 45 | OCH₂C₆H₄—NHSO₂CH₃(4) | N |
| 46 | OCH₂C₆H₄—CN(3) | N |
| 47 | OCH₂C₆H₄—CN(4) | N |
| 48 | OCH₂C₆H₄—CONH₂(3) | N |
| 49 | OCH₂C₆H₄—CONH₂(4) | N |
| 50 | OCH₂C₆H₄—OCH₂CN(3) | N |
| 51 | OCH₂C₆H₄—OCH₂CN(4) | N |
| 52 | OCH₂C₆H₄—OCH₂CONH₂(3) | N |
| 53 | OCH₂C₆H₄—OCH₂CONH₂(4) | N |
| 54 | OCH₂C₆H₄CH₂CN(3) | N |
| 55 | OCH₂C₆H₄CH₂CN(4) | N |
| 56 | OCH₂C₆H₄CH₂CONH₂(3) | N |
| 57 | OCH₂C₆H₄CH₂CONH₂(4) | N |
| 58 | OCH₂C₆H₃(CN)₂(3,5) | N |
| 59 | OCH₂C₆H₃(CN)₂(3,5) | N |
| 60 | OCH₂C₆H₃(CONH₂)₂(3,5) | N |
| 61 | OCH₂C₆H₃(CONH₂)₂(3,5) | N |
| 62 | OCH₂C₆H₄C₆H₄CN(2, 3, or 4) | N |
| 63 | OCH₂C₆H₄C₆H₄CONH₂(2, 3, or 4) | N |

TABLE X

![benzamide structure with X on aryl, A in ring, C(O)NH-CH2CH2-NH2]

| Ex. # | X | A |
|---|---|---|
| 1 | OCH₂CH₂C₆H₅ | CH |
| 2 | OCH₂C₆H₅ | CH |
| 3 | OCH₂C₆H₄—Cl(3) | CH |
| 4 | OCH₂C₆H₄—Cl(4) | CH |
| 5 | OCH₂C₆H₄—F(3) | CH |
| 6 | OCH₂C₆H₄—F(4) | CH |
| 7 | OCH₂C₆H₄—CF₃(3) | CH |
| 8 | OCH₂C₆H₄—CF₃(4) | CH |
| 9 | OCH₂C₆H₄—NO₂(3) | CH |
| 10 | OCH₂C₆H₄—NO₂(4) | CH |
| 11 | OCH₂C₆H₄—OCH₃(3) | CH |
| 12 | OCH₂C₆H₄—OCH₃(4) | CH |
| 13 | OCH₂C₆H₄—NHSO₂CH₃(3) | CH |
| 14 | OCH₂C₆H₄—NHSO₂CH₃(4) | CH |
| 15 | OCH₂C₆H₄—CN(3) | CH |
| 16 | OCH₂C₆H₄—CN(4) | CH |
| 17 | OCH₂C₆H₄—CONH₂(3) | CH |
| 18 | OCH₂C₆H₄—CONH₂(4) | CH |
| 19 | OCH₂C₆H₄—OCH₂CN(3) | CH |
| 20 | OCH₂C₆H₄—OCH₂CN(4) | CH |
| 21 | OCH₂C₆H₄—OCH₂CONH₂(3) | CH |
| 22 | OCH₂C₆H₄—OCH₂CONH₂(4) | CH |
| 23 | OCH₂C₆H₄CH₂CN(3) | CH |
| 24 | OCH₂C₆H₄CH₂CN(4) | CH |
| 25 | OCH₂C₆H₄CH₂CONH₂(3) | CH |
| 26 | OCH₂C₆H₄CH₂CONH₂(4) | CH |

TABLE X-continued

Structure: X-C6H3(A)-C(=O)-NH-CH2CH2-NH2

| Ex. # | X | A |
|---|---|---|
| 27 | OCH$_2$C$_6$H$_5$CO$_2$Et(3) | CH |
| 28 | OCH$_2$C$_6$H$_5$CO$_2$H(3) | CH |
| 29 | OCH$_2$C$_6$H$_5$CO$_2$Et(4) | CH |
| 30 | OCH$_2$C$_6$H$_5$CO$_2$H(4) | CH |
| 31 | OCH$_2$C$_6$H$_5$CH$_2$CO$_2$Et(3) | CH |
| 32 | OCH$_2$C$_6$H$_5$CH$_2$CO$_2$H(3) | CH |
| 33 | OCH$_2$C$_6$H$_5$CH$_2$CO$_2$Et(4) | CH |
| 34 | OCH$_2$C$_6$H$_5$CH$_2$CO$_2$H(4) | CH |
| 35 | OCH$_2$C$_6$H$_5$OCH$_2$CO$_2$Et(3) | CH |
| 36 | OCH$_2$C$_6$H$_5$OCH$_2$CO$_2$H(3) | CH |
| 37 | OCH$_2$C$_6$H$_5$OCH$_2$CO$_2$Et(4) | CH |
| 38 | OCH$_2$C$_6$H$_5$OCH$_2$CO$_2$H(4) | CH |
| 39 | OCH$_2$C$_6$H$_3$(CN)$_2$(3,5) | CH |
| 40 | OCH$_2$C$_6$H$_3$(CN)$_2$(3,5) | CH |
| 41 | OCH$_2$C$_6$H$_3$(CONH$_2$)$_2$(3,5) | CH |
| 42 | OCH$_2$C$_6$H$_3$(CONH$_2$)$_2$(3,5) | CH |
| 43 | OCH$_2$C$_6$H$_4$C$_6$H$_4$CN(2, 3, or 4) | CH |
| 44 | OCH$_2$C$_6$H$_4$C$_6$H$_4$CONH$_2$(2, 3, or 4) | CH |
| 45 | OCH$_2$C$_6$H$_4$C$_6$H$_4$CO$_2$Et(2, 3, or 4) | CH |
| 46 | OCH$_2$C$_6$H$_4$C$_6$H$_4$CO$_2$H(2, 3, or 4) | CH |
| 47 | OCH$_2$C$_6$H$_4$—CH$_3$(3) | CH |
| 48 | OCH$_2$C$_6$H$_4$—CH$_3$(4) | CH |

TABLE XI

| Ex. # | X | A |
|---|---|---|
| 1 | OCH$_2$CH$_2$C$_6$H$_5$ | N |
| 2 | OCH$_2$C$_6$H$_5$ | N |
| 3 | OCH$_2$C$_6$H$_4$—Cl(3) | N |
| 4 | OCH$_2$C$_6$H$_4$—Cl(4) | N |
| 5 | OCH$_2$C$_6$H$_4$—F(3) | N |
| 6 | OCH$_2$C$_6$H$_4$—F(4) | N |
| 7 | OCH$_2$C$_6$H$_4$—CF$_3$(3) | N |
| 8 | OCH$_2$C$_6$H$_4$—CF$_3$(4) | N |
| 9 | OCH$_2$C$_6$H$_4$—NO$_2$(3) | N |
| 10 | OCH$_2$C$_6$H$_4$—NO$_2$(4) | N |
| 11 | OCH$_2$C$_6$H$_4$—NHSO$_2$CH$_3$(3) | N |
| 12 | OCH$_2$C$_6$H$_4$—NHSO$_2$CH$_3$(4) | N |
| 13 | OCH$_2$C$_6$H$_4$—CN(3) | N |
| 14 | OCH$_2$C$_6$H$_4$—CN(4) | N |
| 15 | OCH$_2$C$_6$H$_4$—CONH$_2$(3) | N |
| 16 | OCH$_2$C$_6$H$_4$—CONH$_2$(4) | N |
| 17 | OCH$_2$C$_6$H$_4$—OCH$_2$CN(3) | N |
| 18 | OCH$_2$C$_6$H$_4$—OCH$_2$CN(4) | N |
| 19 | OCH$_2$C$_6$H$_4$—OCH$_2$CONH$_2$(3) | N |
| 20 | OCH$_2$C$_6$H$_4$—OCH$_2$CONH$_2$(4) | N |
| 21 | OCH$_2$C$_6$H$_4$CH$_2$CN(3) | N |
| 22 | OCH$_2$C$_6$H$_4$CH$_2$CN(4) | N |
| 23 | OCH$_2$C$_6$H$_4$CH$_2$CONH$_2$(3) | N |
| 24 | OCH$_2$C$_6$H$_4$CH$_2$CONH$_2$(4) | N |
| 25 | OCH$_2$C$_6$H$_5$CO$_2$Et(3) | N |
| 26 | OCH$_2$C$_6$H$_5$CO$_2$H(3) | N |
| 27 | OCH$_2$C$_6$H$_5$CO$_2$Et(4) | N |
| 28 | OCH$_2$C$_6$H$_5$CO$_2$H(4) | N |
| 29 | OCH$_2$C$_6$H$_5$CH$_2$CO$_2$Et(3) | N |
| 30 | OCH$_2$C$_6$H$_5$CH$_2$CO$_2$H(3) | N |
| 31 | OCH$_2$C$_6$H$_5$CH$_2$CO$_2$Et(4) | N |
| 32 | OCH$_2$C$_6$H$_5$CH$_2$CO$_2$H(4) | N |

TABLE XI-continued

| Ex. # | X | A |
|---|---|---|
| 33 | OCH$_2$C$_6$H$_5$OCH$_2$CO$_2$Et(3) | N |
| 34 | OCH$_2$C$_6$H$_5$OCH$_2$CO$_2$H(3) | N |
| 35 | OCH$_2$C$_6$H$_5$OCH$_2$CO$_2$Et(4) | N |
| 36 | OCH$_2$C$_6$H$_5$OCH$_2$CO$_2$H(4) | N |
| 37 | OCH$_2$C$_6$H$_3$(CN)$_2$(3,5) | N |
| 38 | OCH$_2$C$_6$H$_3$(CN)$_2$(3,5) | N |
| 39 | OCH$_2$C$_6$H$_3$(CONH$_2$)$_2$(3,5) | N |
| 40 | OCH$_2$C$_6$H$_3$(CONH$_2$)$_2$(3,5) | N |
| 41 | OCH$_2$C$_6$H$_4$—OCH$_3$(3) | N |
| 42 | OCH$_2$C$_6$H$_4$—OCH$_3$(4) | N |
| 43 | OCH$_2$C$_6$H$_4$C$_6$H$_4$CN(2,3, or 4) | N |
| 44 | OCH$_2$C$_6$H$_4$C$_6$H$_4$CONH$_2$(2,3, or 4) | N |
| 45 | OCH$_2$C$_6$H$_4$C$_6$H$_4$CO$_2$Et(2,3, or 4) | N |
| 46 | OCH$_2$C$_6$H$_4$C$_6$H$_4$CO$_2$H(2,3, or 4) | N |
| 47 | OCH$_2$C$_6$H$_4$—CH$_3$(3) | N |
| 48 | OCH$_2$C$_6$H$_4$—CH$_3$(4) | N |

TABLE XII

| Ex. # | X | A |
|---|---|---|
| 1 | NHCH$_2$CH$_2$C$_6$H$_5$ | CH |
| 2 | NHCH$_2$C$_6$H$_5$ | CH |
| 3 | NHCH$_2$C$_6$H$_4$—Cl(3) | CH |
| 4 | NHCH$_2$C$_6$H$_4$—Cl(4) | CH |
| 5 | NHCH$_2$C$_6$H$_4$—F(3) | CH |
| 6 | NHCH$_2$C$_6$H$_4$—F(4) | CH |
| 7 | NHCH$_2$C$_6$H$_4$—CF$_3$(3) | CH |
| 8 | NHCH$_2$C$_6$H$_4$—CF$_3$(4) | CH |
| 9 | NHCH$_2$C$_6$H$_4$—NO$_2$(3) | CH |
| 10 | NHCH$_2$C$_6$H$_4$—NO$_2$(4) | CH |
| 11 | NHCH$_2$C$_6$H$_4$—NHSO$_2$CH$_3$(3) | CH |
| 12 | NHCH$_2$C$_6$H$_4$—NHSO$_2$CH$_3$(4) | CH |
| 13 | NHCH$_2$C$_6$H$_4$—CN(3) | CH |
| 14 | NHCH$_2$C$_6$H$_4$—CN(4) | CH |
| 15 | NHCH$_2$C$_6$H$_4$—CONH$_2$(3) | CH |
| 16 | NHCH$_2$C$_6$H$_4$—CONH$_2$(4) | CH |
| 17 | NHCH$_2$C$_6$H$_4$—OCH$_2$CN(3) | CH |
| 18 | NHCH$_2$C$_6$H$_4$—OCH$_2$CN(4) | CH |
| 19 | NHCH$_2$C$_6$H$_4$—OCH$_2$CONH$_2$(3) | CH |
| 20 | NHCH$_2$C$_6$H$_4$—OCH$_2$CONH$_2$(4) | CH |
| 21 | NHCH$_2$C$_6$H$_4$CH$_2$CN(3) | CH |
| 22 | NHCH$_2$C$_6$H$_4$CH$_2$CN(4) | CH |
| 23 | NHCH$_2$C$_6$H$_4$CH$_2$CONH$_2$(3) | CH |
| 24 | NHCH$_2$C$_6$H$_4$CH$_2$CONH$_2$(4) | CH |
| 25 | NHCH$_2$C$_6$H$_5$CO$_2$Et(3) | CH |
| 26 | NHCH$_2$C$_6$H$_5$CO$_2$H(3) | CH |
| 27 | NHCH$_2$C$_6$H$_5$CO$_2$Et(4) | CH |
| 28 | NHCH$_2$C$_6$H$_5$CO$_2$H(4) | CH |
| 29 | NHCH$_2$C$_6$H$_5$CH$_2$CO$_2$Et(3) | CH |
| 30 | NHCH$_2$C$_6$H$_5$CH$_2$CO$_2$H(3) | CH |
| 31 | NHCH$_2$C$_6$H$_5$CH$_2$CO$_2$Et(4) | CH |
| 32 | NHCH$_2$C$_6$H$_5$CH$_2$CO$_2$H(4) | CH |
| 33 | NHCH$_2$C$_6$H$_5$OCH$_2$CO$_2$Et(3) | CH |
| 34 | NHCH$_2$C$_6$H$_5$OCH$_2$CO$_2$H(3) | CH |
| 35 | NHCH$_2$C$_6$H$_5$OCH$_2$CO$_2$Et(4) | CH |
| 36 | NHCH$_2$C$_6$H$_5$OCH$_2$CO$_2$H(4) | CH |
| 37 | NHCH$_2$C$_6$H$_3$(CN)$_2$(3,5) | CH |
| 38 | NHCH$_2$C$_6$H$_3$(CN)$_2$(3,5) | CH |

TABLE XII-continued

Structure: X-C6H3(A)-C(=O)-NH-CH2CH2-NH2

| Ex. # | X | A |
|---|---|---|
| 39 | NHCH2C6H3(CONH2)2(3,5) | CH |
| 40 | NHCH2C6H3(CONH2)2(3,5) | CH |
| 41 | NHCH2C6H4—OCH3(3) | CH |
| 42 | NHCH2C6H4—OCH3(4) | CH |
| 43 | NHCH2C6H4C6H4CN(2,3, or 4) | CH |
| 44 | NHCH2C6H4C6H4CONH2(2,3, or 4) | CH |
| 45 | NHCH2C6H4C6H4CO2Et(2,3, or 4) | CH |
| 46 | NHCH2C6H4C6H4CO2H(2,3, or 4) | CH |
| 47 | NHCH2C6H4—CH3(3) | CH |
| 48 | NHCH2C6H4—CH3(4) | CH |

TABLE XIII

| Ex. # | X | A |
|---|---|---|
| 1 | NHCH2CH2C6H5 | N |
| 2 | NHCH2C6H5 | N |
| 3 | NHCH2C6H4—Cl(3) | N |
| 4 | NHCH2C6H4—Cl(4) | N |
| 5 | NHCH2C6H4—F(3) | N |
| 6 | NHCH2C6H4—F(4) | N |
| 7 | NHCH2C6H4—CF3(3) | N |
| 8 | NHCH2C6H4—CF3(4) | N |
| 9 | NHCH2C6H4—NO2(3) | N |
| 10 | NHCH2C6H4—NO2(4) | N |
| 11 | NHCH2C6H4—NHSO2CH3(3) | N |
| 12 | NHCH2C6H4—NHSO2CH3(4) | N |
| 13 | NHCH2C6H4—CN(3) | N |
| 14 | NHCH2C6H4—CN(4) | N |
| 15 | NHCH2C6H4—CONH2(3) | N |
| 16 | NHCH2C6H4—CONH2(4) | N |
| 17 | NHCH2C6H4—OCH2CN(3) | N |
| 18 | NHCH2C6H4—OCH2CN(4) | N |
| 19 | NHCH2C6H4—OCH2CONH2(3) | N |
| 20 | NHCH2C6H4—OCH2CONH2(4) | N |
| 21 | NHCH2C6H4CH2CN(3) | N |
| 22 | NHCH2C6H4CH2CN(4) | N |
| 23 | NHCH2C6H4CH2CONH2(3) | N |
| 24 | NHCH2C6H4CH2CONH2(4) | N |
| 25 | NHCH2C6H5CO2Et(3) | N |
| 26 | NHCH2C6H5CO2H(3) | N |
| 27 | NHCH2C6H5CO2Et(4) | N |
| 28 | NHCH2C6H5CO2H(4) | N |
| 29 | NHCH2C6H5CH2CO2Et(3) | N |
| 30 | NHCH2C6H5CH2CO2H(3) | N |
| 31 | NHCH2C6H5CH2CO2Et(4) | N |
| 32 | NHCH2C6H5CH2CO2H(4) | N |
| 33 | NHCH2C6H5OCH2CO2Et(3) | N |
| 34 | NHCH2C6H5OCH2CO2H(3) | N |
| 35 | NHCH2C6H5OCH2CO2Et(4) | N |
| 36 | NHCH2C6H5OCH2CO2H(4) | N |
| 37 | NHCH2C6H3(CN)2(3,5) | N |
| 38 | NHCH2C6H3(CN)2(3,5) | N |
| 39 | NHCH2C6H3(CONH2)2(3,5) | N |
| 40 | NHCH2C6H3(CONH2)2(3,5) | N |
| 41 | NHCH2C6H4—OCH3(3) | N |
| 42 | NHCH2C6H4—OCH3(4) | N |
| 43 | NHCH2C6H4C6H4CN(2,3, or 4) | N |
| 44 | NHCH2C6H4C6H4CONH2(2,3, or 4) | N |

TABLE XIII-continued

| Ex. # | X | A |
|---|---|---|
| 45 | NHCH2C6H4C6H4CO2Et(2,3, or 4) | N |
| 46 | NHCH2C6H4C6H4CO2H(2,3, or 4) | N |
| 47 | NHCH2C6H4—CH3(3) | N |
| 48 | NHCH2C6H4—CH3(4) | N |

TABLE XIV

| Ex. # | X | A |
|---|---|---|
| 1. | O(CH2CH2O)2CH2CH2OH | CH |
| 2. | O(CH2CH2O)2CH2CH2OH | N |
| 3. | O(CH2CH2O)2CH2CH2OCH3 | CH |
| 4. | O(CH2CH2O)2CH2CH2OCH3 | N |
| 5. | O(CH2CH2O)3CH2CH2OH | CH |
| 6. | O(CH2CH2O)3CH2CH2OH | N |
| 7. | O(CH2CH2O)3CH2CH2OCH3 | CH |
| 8. | O(CH2CH2O)3CH2CH2OCH3 | N |
| 9. | O(CH2CH2O)4CH2CH2OH | CH |
| 10. | O(CH2CH2O)4CH2CH2OH | N |
| 11. | O(CH2CH2O)4CH2CH2OCH3 | CH |
| 12. | O(CH2CH2O)4CH2CH2OCH3 | N |
| 13. | O(CH2CH2O)5CH2CH2OH | CH |
| 14. | O(CH2CH2O)5CH2CH2OH | N |
| 15. | O(CH2CH2O)5CH2CH2OCH3 | CH |
| 16. | O(CH2CH2O)5CH2CH2OCH3 | N |
| 17. | O(CH2CH2O)7CH2CH2OH | CH |
| 18. | O(CH2CH2O)7CH2CH2OH | N |
| 19. | O(CH2CH2O)7CH2CH2OCH3 | CH |
| 20. | O(CH2CH2O)7CH2CH2OCH3 | N |
| 21. | O(CH2CH2O)9CH2CH2OH | CH |
| 22. | O(CH2CH2O)9CH2CH2OH | N |
| 23. | O(CH2CH2O)9CH2CH2OCH3 | CH |
| 24. | O(CH2CH2O)9CH2CH2OCH3 | N |
| 25. | O(CH2CH2O)11CH2CH2OCH3 | CH |
| 26. | O(CH2CH2O)11CH2CH2OCH3 | N |

Numerous modifications and variations of the present invention are possible in light of the above teachings. It is therefore to be understood that within the scope of the appended claims, the invention may be practiced otherwise that as specifically described herein.

What is claimed is:
1. A compound of formula I, or a stereoisomer or a pharmaceutically acceptable salt thereof:

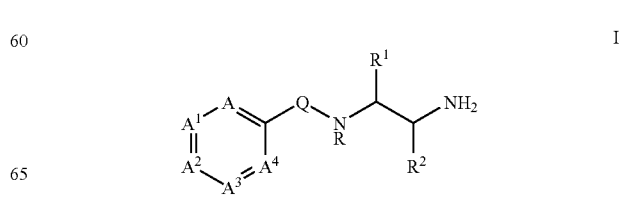

I wherein:

A is N;

$A^1$ and $A^3$ are CH;

$A^2$ is CX;

$A^4$ is CY;

R, at each occurrence, is independently selected from H and $C_{1-6}$ alkyl;

$R^1$ is selected from H and $C_{1-6}$ alkyl;

$R^2$ is selected from H and $C_{1-6}$ alkyl;

Q is C=O;

X is selected from H, $OR^3$, $NR^3Z$, OZ, SZ, $SO_2OR^3$, $SO_2NR^3R^4$, $CO_2R^3$, $CONR^3R^4$, $PO(OR^3)_2$, $(CH_2)_mCO_2R$, $(CH_2)_mCONR_2$, NR—$C_{2-4}$ alkenyl, $NRSO_2CH_3$, $NR(CH_2)_nCO_2R$, $CH_2$-aryl, $O(CH_2)_n$-biphenyl, $O(CH_2)_n$-biphenyl-$(CH_2)_mCO_2R$, $O(CH_2)_n$-biphenyl-$(CH_2)_mCN$, $O(CH_2)_n$-biphenyl-$(CH_2)_mCON(R)_2$, $NR(CH_2)_n$-biphenyl-$(CH_2)_mCO_2R$, $NR(CH_2)_n$-biphenyl-$(CH_2)_mCN$, $NR(CH_2)_n$-biphenyl, $NR(CH_2)_n$-biphenyl-$(CH_2)_mCON(R)_2$, $O(CH_2)_n$-aryl, $O(CH_2)_n$-heteroaryl, $NR(CH_2)_n$-aryl, $NR(CH_2)_n$-heteroaryl, $O(CH_2)_n$-aryl$(CH_2)_mCO_2R$, $O(CH_2)_n$-aryl-$C_{2-6}$ alkenyl-$CO_2R$, $O(CH_2)_n$-aryl$(CH_2)_mCN$, $O(CH_2)_n$-aryl$(CH_2)_mCON(R)_2$, $O(CH_2)_n$-aryl$(CH_2)_m$—$PO(OR)_2$, $O(CH_2)_n$-aryl-$O(CH_2)_nCO_2R$, $O(CH_2)_n$-aryl-O—$C_{2-6}$ alkenyl-$CO_2R$, $O(CH_2)_n$-arylO$(CH_2)_nCN$, $O(CH_2)_n$-arylO$(CH_2)_nCON(R)_2$, $O(CH_2)_n$-arylO$(CH_2)_n$—$PO(OR)_2$, $O(CH_2)_n$-aryl-$NR(CH_2)_nCO_2R$, $O(CH_2)_n$-aryl-$NRC_{2-6}$ alkenyl-$CO_2R$, $O(CH_2)_n$-aryl-$NR(CH_2)_nCN$, $O(CH_2)_n$-aryl-$NR(CH_2)_nCON(R)_2$, $O(CH_2)_n$-aryl-$NR(CH_2)_n$—$PO(OR)_2$, $NR(CH_2)_n$-aryl$(CH_2)_mCO_2R$, $NR(CH_2)_n$-aryl-$C_{2-6}$ alkenyl-$CO_2R$, $NR(CH_2)_n$-aryl$(CH_2)_mCN$, $NR(CH_2)_n$-aryl$(CH_2)_mCON(R)_2$, $NR(CH_2)_n$-aryl$(CH_2)_m$—$PO(OR)_2$, $NR(CH_2)_n$-aryl-$NR(CH_2)_nCO_2R$, $NR(CH_2)_n$-aryl-NR—$C_{2-6}$ alkenyl-$CO_2R$, $NR(CH_2)_n$-aryl-$NR(CH_2)_nCN$, $NR(CH_2)_n$-aryl-$NR(CH_2)_nCON(R)_2$, $NR(CH_2)_n$-aryl-$NR(CH_2)_nPO(OR)_2$, $NR(CH_2)_n$-arylO$(CH_2)_nCO_2R$, $NR(CH_2)_n$-aryl-O—$C_{2-6}$ alkenyl-$CO_2R$, $NR(CH_2)_n$-arylO$(CH_2)_nCN$, $NR(CH_2)_n$-aryl-$O(CH_2)_nCON(R)_2$, $NR(CH_2)_n$-arylO$(CH_2)_nPO(OR)_2$, $O(CH_2)_n$-heteroaryl$(CH_2)_mCO_2R$, $O(CH_2)_n$-heteroaryl-$C_{2-6}$ alkenyl-$CO_2R$, $O(CH_2)_n$-heteroaryl-$(CH_2)_mCN$, $O(CH_2)_n$-heteroaryl$(CH_2)_mCON(R)_2$, $O(CH_2)_n$-heteroaryl$(CH_2)_m$—$PO(OR)_2$, $O(CH_2)_n$-heteroaryl-$O(CH_2)_nCO_2R$, $O(CH_2)_n$-heteroaryl-O—$C_{2-6}$ alkenyl-$CO_2R$, $O(CH_2)_n$-heteroarylO$(CH_2)_nCN$, $O(CH_2)_n$-heteroarylO$(CH_2)_nCON(R)_2$, $O(CH_2)_n$-heteroarylO$(CH_2)_n$—$PO(OR)_2$, $O(CH_2)_n$-heteroaryl-$NR(CH_2)_nCO_2R$, $O(CH_2)_n$-heteroaryl-NR—$C_{2-6}$ alkenyl-$CO_2R$, $O(CH_2)_n$-heteroaryl-$NR(CH_2)_nCN$, $O(CH_2)_n$-heteroaryl-$NR(CH_2)_nCON(R)_2$, $O(CH_2)_n$-heteroaryl-$NR(CH_2)_n$—$PO(OR)_2$, $NR(CH_2)_n$-heteroaryl$(CH_2)_mCO_2R$, $NR(CH_2)_n$-heteroaryl-$C_{2-6}$ alkenyl-$CO_2R$, $NR(CH_2)_n$-heteroaryl, $NR(CH_2)_n$-heteroaryl$(CH_2)_mCN$, $NR(CH_2)_n$-heteroaryl$(CH_2)_mCON(R)_2$, $NR(CH_2)_n$-heteroaryl$(CH_2)_m$—$PO(OR)_2$, $NR(CH_2)_n$-heteroaryl-$NR(CH_2)_nCO_2R$, $NR(CH_2)_n$-heteroaryl-NR—$C_{2-6}$ alkenyl-$CO_2R$, $NR(CH_2)_n$heteroaryl-$NR(CH_2)_nCN$, $NR(CH_2)_n$-heteroaryl-$NR(CH_2)_nCON(R)_2$, $NR(CH_2)_n$-heteroaryl-$NR(CH_2)_nPO(OR)_2$, $NR(CH_2)_n$-heteroaryl-$O(CH_2)_nCO_2R$, $NR(CH_2)_n$-heteroaryl-O—$C_{2-6}$ alkenyl-$CO_2R$, $NR(CH_2)_n$-heteroaryl-$O(CH_2)_nCN$, $NR(CH_2)_n$-heteroaryl-$O(CH_2)_nCON(R)_2$, $NR(CH_2)_n$-heteroarylO$(CH_2)_nPO(OR)_2$, and $O(CH_2CH_2O)_pCH_2CH_2OR^3$, where heteroaryl is a 5-12 membered ring system consisting of carbon atoms and from 1-4 heteroatoms selected from N, O, and S, and wherein aryl, heteroaryl, and biphenyl are substituted with 1-2 $X^2$;

$X^2$, at each occurrence, is independently selected from H, OR, $C_{1-4}$ alkyl, $C_{1-4}$ alkyloxy, fluoro-$C_{1-4}$ alkyloxy, $C_{2-4}$ alkenyl, $C_{2-4}$ alkynyl, halogen, $CF_3$, nitro, —CN, $CON(R)_2$, and $SO_2N(R)C_{1-4}$alkyl;

Y is selected from H, $OR^3$, $NR^3Z$, OZ, SZ, $SO_2OR^3$, $SO_2NR^3R^4$, $CO_2R^3$, $CONR^3R^4$, $PO(OR^3)_2$, $CF_3$, $CON(R)_2$, $SO_2N(R)C_{1-4}$alkyl and $NHSO_2R$;

provided that when Q is C=O and A, $A^1$, $A^2$, $A^3$, and $A^4$ are other than $N^+$—$O^-$, then at least one of X and Y is present and is other than H, OH, $OC_{1-6}$ alkyl, $OC_{2-6}$ alkenyl, and aryl-$C_{1-6}$ alkyl-O—;

Z, at each occurrence, is independently selected from $(CH_2)_nCO_2R^3$, $CH_2CH$=$CHCO_2R^3$, $(CH_2)_nCN$, $(CH_2)_nCONR^3R^4$, $CH_2CH$=CHCN, $CH_2CH$=$CHCON(R^3)_2$, $(CH_2)_nPO(OR^3)_2$, $(CH_2)_nSO_3R^3$, and $(CH_2)_nN^+(R^3)_3G^-$;

$G^-$ is a counterion;

$R^3$, at each occurrence, is independently selected from H, $C_{1-6}$ alkyl, $C_{2-6}$ alkenyl, and aryl-$C_{1-6}$ alkyl-;

$R^4$, at each occurrence, is independently selected from H, $C_{1-6}$ alkyl, phenyl, and $CH(L)CO_2R^3$;

L is selected from H, $C_{1-6}$ alkyl, —$(CH_2)_m$-phenyl, —$(CH_2)_n$—O—$C_{1-6}$ alkyl, and —$(CH_2)_n$—S—$C_{1-6}$ alkyl;

m, at each occurrence, is independently selected from 0, 1, 2, 3, and 4;

n, at each occurrence, is independently selected from 1, 2, 3, and 4; and, p is selected from 1, 2, 3, 4, 5, 6, 7, 8, 9, 10, and 11.

2. A compound of claim 1, wherein the compound is of formula Ia, or a stereoisomer or a pharmaceutically acceptable salt thereof:

Ia wherein:

A is N;

$A^1$ and $A^3$ are CH;

R, at each occurrence, is independently selected from H and $C_{1-4}$ alkyl;

$R^1$ is selected from H and $C_{1-4}$ alkyl;

$R^2$ is selected from H and $C_{1-4}$ alkyl;

X is selected from H, $OR^3$, $NR^3Z$, OZ, SZ, $SO_2NR^3R^4$, $CONR^3R^4$, $(CH_2)_mCONR_2$, NR—$C_{2-4}$ alkenyl, $NRSO_2CH_3$, $CH_2$-aryl, $O(CH_2)_n$-biphenyl, $O(CH_2)_n$-biphenyl-$(CH_2)_mCN$, $O(CH_2)_n$-biphenyl-$(CH_2)_mCON(R)_2$, $NR(CH_2)_n$-biphenyl, $NR(CH_2)_n$-biphenyl-$(CH_2)_mCN$, $NR(CH_2)_n$-biphenyl-$(CH_2)_mCON(R)_2$, $O(CH_2)_n$-aryl, $O(CH_2)_n$-heteroaryl, $NR(CH_2)_n$-aryl, $NR(CH_2)_n$-heteroaryl, $O(CH_2)_n$-aryl$(CH_2)_mCN$, $O(CH_2)_n$-aryl$(CH_2)_mCON(R)_2$, $O(CH_2)_n$-arylO$(CH_2)_nCN$, $O(CH_2)_n$-arylO$(CH_2)_nCON(R)_2$, $O(CH_2)_n$-aryl-$NR(CH_2)_nCN$, $O(CH_2)_n$-aryl-$NR(CH_2)_nCON(R)_2$, $NR(CH_2)_n$-aryl$(CH_2)_mCN$, $NR(CH_2)_n$-aryl$(CH_2)_mCON(R)_2$, $NR(CH_2)_n$-aryl-$NR(CH_2)_nCN$, $NR(CH_2)_n$-aryl-$NR(CH_2)_nCON(R)_2$, $NR(CH_2)_n$-arylO$(CH_2)_nCN$, $NR(CH_2)_n$-aryl-$O(CH_2)_nCON(R)_2$, $O(CH_2)_n$-heteroaryl-$(CH_2)_mCN$, $O(CH_2)_n$-heteroaryl$(CH_2)_mCON$ (R)$_2$, O(CH$_2$)$_n$-heteroarylO(CH$_2$)$_n$CN, O(CH$_2$)$_n$-heteroarylO(CH$_2$)$_n$CON(R)$_2$, O(CH$_2$)$_n$-heteroaryl-NR(CH$_2$)$_n$CN, O(CH$_2$)$_n$-heteroaryl-NR(CH$_2$)$_n$CON(R)$_2$, NR(CH$_2$)$_n$-heteroaryl(CH$_2$)$_m$CN, NR(CH$_2$)$_n$-heteroaryl(CH$_2$)$_m$CON(R)$_2$, NR(CH$_2$)$_n$-heteroaryl-NR(CH$_2$)$_n$CN, NR(CH$_2$)$_n$-heteroaryl-NR(CH$_2$)$_n$CON(R)$_2$, NR(CH$_2$)$_n$-heteroaryl-O(CH$_2$)$_n$CN, NR(CH$_2$)$_n$-heteroaryl-O(CH$_2$)$_n$CON(R)$_2$, and O(CH$_2$CH$_2$O)$_p$CH$_2$CH$_2$OR$^3$, where heteroaryl is a 5-12 membered ring system consisting of carbon atoms and from 1-4 heteroatoms selected from N, O, and S, and wherein aryl, heteroaryl, and biphenyl are substituted with 1-2 X$^2$;

X$^2$, at each occurrence, is independently selected from H, OR, C$_{1-4}$ alkyl, C$_{2-4}$ alkenyl, C$_{2-4}$ alkynyl, halogen, CF$_3$, nitro, —CN, CON(R)$_2$, and SO$_2$N(R)C$_{1-4}$alkyl;

Y is selected from SO$_2$OR$^3$, CO$_2$R$^3$, PO(OR$^3$)$_2$, SO$_2$N(R)C$_{1-4}$alkyl, and NHSO$_2$R;

Z is selected from (CH$_2$)$_n$CONR$^3$R$^4$, CH$_2$CH=CHCON(R$^3$)$_2$, and (CH$_2$)$_n$N$^+$(R$^3$)$_3$G$^-$;

G$^-$ is selected from Cl$^-$ and Br$^-$;

R$^3$, at each occurrence, is independently selected from H, C$_{1-4}$ alkyl, C$_{2-4}$ alkenyl, and benzyl;

R$^4$, at each occurrence, is independently selected from H, C$_{1-4}$ alkyl, phenyl, and CH(L)CO$_2$R$^3$; and, L is selected from H, CH$_3$, CH$_2$CH$_3$, CH(CH$_3$)$_2$, CH$_2$CH(CH$_3$)$_2$, CH(CH$_3$)CH$_2$CH$_3$, CH$_2$CH$_2$SCH$_3$, phenyl, and benzyl.

3. A compound of claim 1, wherein the compound is of formula Ia, or a stereoisomer or a pharmaceutically acceptable salt thereof:

wherein:
A is N;
A$^1$ and A$^3$ are CH;
R, at each occurrence, is independently selected from H and C$_{1-4}$ alkyl;
R$^1$ is selected from H and C$_{1-4}$ alkyl;
R$^2$ is selected from H and C$_{1-4}$ alkyl;
X is selected from SO$_2$OR$^3$, PO(OR$^3$)$_2$, (CH$_2$)$_m$CO$_2$R, NR(CH$_2$)$_n$CO$_2$R, O(CH$_2$)$_n$-biphenyl-(CH$_2$)$_m$CO$_2$R, NR(CH$_2$)$_n$-biphenyl-(CH$_2$)$_m$CO$_2$R, O(CH$_2$)$_n$-aryl(CH$_2$)$_m$CO$_2$R, O(CH$_2$)$_n$-aryl-C$_{2-6}$ alkenyl-CO$_2$R, O(CH$_2$)$_n$-aryl(CH$_2$)$_m$—PO(OR)$_2$, O(CH$_2$)$_n$-aryl-O(CH$_2$)$_n$CO$_2$R, O(CH$_2$)$_n$-aryl-O—C$_{2-6}$ alkenyl-CO$_2$R, O(CH$_2$)$_n$-arylO(CH$_2$)$_n$—PO(OR)$_2$, O(CH$_2$)$_n$-aryl-NR(CH$_2$)$_n$CO$_2$R, O(CH$_2$)$_n$-aryl-NRC$_{2-6}$ alkenyl-CO$_2$R, O(CH$_2$)$_n$-aryl-NR(CH$_2$)$_n$—PO(OR)$_2$, NR(CH$_2$)$_n$-aryl(CH$_2$)$_m$CO$_2$R, NR(CH$_2$)$_n$-aryl-C$_{2-6}$ alkenyl-CO$_2$R, NR(CH$_2$)$_n$-aryl(CH$_2$)$_m$—PO(OR)$_2$, NR(CH$_2$)$_n$-aryl-NR(CH$_2$)$_n$CO$_2$R, NR(CH$_2$)$_n$-aryl-NR—C$_{2-6}$ alkenyl-CO$_2$R, NR(CH$_2$)$_n$-aryl-NR(CH$_2$)$_n$PO(OR)$_2$, NR(CH$_2$)$_n$-arylO(CH$_2$)$_n$CO$_2$R, NR(CH$_2$)$_n$-aryl-O—C$_{2-6}$ alkenyl-CO$_2$R, NR(CH$_2$)$_n$-arylO(CH$_2$)$_n$PO(OR)$_2$, O(CH$_2$)$_n$-heteroaryl(CH$_2$)$_m$CO$_2$R, O(CH$_2$)$_n$-heteroaryl-C$_{2-6}$ alkenyl-CO$_2$R, O(CH$_2$)$_n$-heteroaryl(CH$_2$)$_m$—PO(OR)$_2$, O(CH$_2$)$_n$-heteroaryl-O(CH$_2$)$_n$CO$_2$R, O(CH$_2$)$_n$-heteroaryl-O—C$_{2-6}$ alkenyl-CO$_2$R, O(CH$_2$)$_n$-heteroarylO(CH$_2$)$_n$—PO(OR)$_2$, O(CH$_2$)$_n$-heteroaryl-NR(CH$_2$)$_n$CO$_2$R, O(CH$_2$)$_n$-heteroaryl-NR—C$_{2-6}$ alkenyl-CO$_2$R, O(CH$_2$)$_n$-heteroaryl-NR(CH$_2$)$_n$—PO(OR)$_2$, NR(CH$_2$)$_n$-heteroaryl(CH$_2$)$_m$CO$_2$R, NR(CH$_2$)$_n$-heteroaryl-C$_{2-6}$ alkenyl-CO$_2$R, NR(CH$_2$)$_n$-heteroaryl(CH$_2$)$_m$—PO(OR)$_2$, NR(CH$_2$)$_n$-heteroaryl-NR(CH$_2$)$_n$CO$_2$R, NR(CH$_2$)$_n$-heteroaryl-NR—C$_{2-6}$ alkenyl-CO$_2$R, NR(CH$_2$)$_n$-heteroaryl-NR(CH$_2$)$_n$PO(OR)$_2$, NR(CH$_2$)$_n$-heteroaryl-O(CH$_2$)$_n$CO$_2$R, NR(CH$_2$)$_n$-heteroaryl-O—C$_{2-6}$ alkenyl-CO$_2$R, NR(CH$_2$)$_n$-heteroarylO(CH$_2$)$_n$PO(OR)$_2$, and O(CH$_2$CH$_2$O)$_p$CH$_2$CH$_2$OR$^3$, where heteroaryl is a 5-12 membered ring system consisting of carbon atoms and from 1-4 heteroatoms selected from N, O, and S, and wherein aryl, heteroaryl, and biphenyl are substituted with 1-2 X$^2$;

X$^2$, at each occurrence, is independently selected from H, OR, C$_{1-4}$ alkyl, C$_{2-4}$ alkenyl, C$_{2-4}$ alkynyl, halogen, CF$_3$, nitro, —CN, CON(R)$_2$, and SO$_2$N(R)C$_{1-4}$alkyl;

Y is selected from H, OW, NR$^3$Z, OZ, SZ, SO$_2$NR$^3$R$^4$, CONR$^3$R$^4$, CF$_3$, CN, CON(R)$_2$, SO$_2$N(R)C$_{1-4}$alkyl, and NHSO$_2$R;

Z is selected from (CH$_2$)$_n$CONR$^3$R$^4$, CH$_2$CH=CHCON(R$^3$)$_2$, and (CH$_2$)$_n$N$^+$(R$^3$)$_3$G$^-$;

G$^-$ is selected from Cl$^-$ and Br$^-$;

R$^3$, at each occurrence, is independently selected from H, C$_{1-4}$ alkyl, C$_{2-4}$ alkenyl, and benzyl;

R$^4$, at each occurrence, is independently selected from H, C$_{1-4}$ alkyl, phenyl, and CH(L)CO$_2$R$^3$; and, L is selected from H, CH$_3$, CH$_2$CH$_3$, CH(CH$_3$)$_2$, CH$_2$CH(CH$_3$)$_2$, CH(CH$_3$)CH$_2$CH$_3$, CH$_2$CH$_2$SCH$_3$, phenyl, and benzyl.

4. A compound of claim 1, wherein the compound is of formula Ib, or a stereoisomer or a pharmaceutically acceptable salt thereof:

wherein:
A is N;
A$^1$ is CH;
R, at each occurrence, is independently selected from H and C$_{1-4}$ alkyl;
R$^1$ is selected from H and C$_{1-4}$ alkyl;
R$^2$ is selected from H and C$_{1-4}$ alkyl;
X is selected from H, OR$^3$, NR$^3$Z, OZ, SZ, SO$_2$NR$^3$R$^4$, CONR$^3$R$^4$, (CH$_2$)$_m$CONR$_2$, NR—C$_{2-4}$ alkenyl, NRSO$_2$CH$_3$, CH$_2$-aryl, O(CH$_2$)$_n$-biphenyl, O(CH$_2$)$_n$-biphenyl-(CH$_2$)$_m$CN, O(CH$_2$)$_n$-biphenyl-(CH$_2$)$_m$CON(R)$_2$, NR(CH$_2$)$_n$-biphenyl, NR(CH$_2$)$_n$-biphenyl-(CH$_2$)$_m$CN, NR(CH$_2$)$_n$-biphenyl-(CH$_2$)$_m$CON(R)$_2$, O(CH$_2$)$_n$-aryl, O(CH$_2$)$_n$-heteroaryl, NR(CH$_2$)$_n$-aryl, NR(CH$_2$)$_n$-heteroaryl, O(CH$_2$)$_n$-aryl(CH$_2$)$_m$CN, O(CH$_2$)$_n$-aryl(CH$_2$)$_m$CON(R)$_2$, O(CH$_2$)$_n$-arylO(CH$_2$)$_n$CN, O(CH$_2$)$_n$-arylO(CH$_2$)$_n$CON(R)$_2$, O(CH$_2$)$_n$-aryl-NR(CH$_2$)$_n$CN, O(CH$_2$)$_n$-aryl-NR(CH$_2$)$_n$CON(R)$_2$, NR(CH$_2$)$_n$-aryl(CH$_2$)$_m$CN, NR(CH$_2$)$_n$-aryl(CH$_2$)$_m$CON(R)$_2$, NR(CH$_2$)$_n$-aryl-NR(CH$_2$)$_n$CN, NR(CH$_2$)$_n$-aryl-NR(CH$_2$)$_n$CON(R)$_2$, NR(CH$_2$)$_n$-arylO(CH$_2$)$_n$CN, NR(CH$_2$)$_n$-aryl-O(CH$_2$)$_n$CON(R)$_2$, O(CH$_2$)$_n$-heteroaryl-(CH$_2$)$_m$CN, O(CH$_2$)$_n$-heteroaryl(CH$_2$)$_m$CON (R)₂, O(CH₂)ₙ-heteroaryl O(CH₂)ₙCN, O(CH₂)ₙ-heteroarylO(CH₂)ₙCON(R)₂, O(CH₂)ₙ-heteroaryl-NR(CH₂)ₙCN, O(CH₂)ₙ-heteroaryl-NR(CH₂)ₙCON(R)₂, NR(CH₂)ₙ-heteroaryl(CH₂)ₘCN, NR(CH₂)ₙ-heteroaryl(CH₂)ₘCON(R)₂, NR(CH₂)ₙ heteroaryl-NR(CH₂)ₙCN, NR(CH₂)ₙ-heteroaryl-NR(CH₂)ₙCON(R)₂, NR(CH₂)ₙ-heteroaryl-O(CH₂)ₙCN, NR(CH₂)ₙ-heteroaryl-O(CH₂)ₙCON(R)₂, and O(CH₂CH₂O)ₚCH₂CH₂OR³, where heteroaryl is a 5-12 membered ring system consisting of carbon atoms and from 1-4 heteroatoms selected from N, O, and S, and wherein aryl, heteroaryl, and biphenyl are substituted with 1-2 X²;

X², at each occurrence, is independently selected from H, OR, $C_{1-4}$ alkyl, $C_{2-4}$ alkenyl, $C_{2-4}$ alkynyl, halogen, $CF_3$, nitro, —CN, CON(R)₂, and SO₂N(R)$C_{1-4}$-alkyl;

Y is selected from SO₂OR³, CO₂R³, PO(OR³)₂, SO₂N(R)$C_{1-4}$alkyl and NHSO₂R;

Z is selected from (CH₂)ₙCONR³R⁴, CH₂CH=CHCON(R³)₂, and (CH₂)ₙN±(R³)₃G⁻;

G⁻ is selected from Cl⁻ and Br⁻;

R³, at each occurrence, is independently selected from H, $C_{1-4}$ alkyl, $C_{2-4}$ alkenyl, and benzyl;

R⁴, at each occurrence, is independently selected from H, $C_{1-4}$ alkyl, phenyl, and CH(L)CO₂R³; and, L is selected from H, CH₃, CH₂CH₃, CH(CH₃)₂, CH₂CH(CH₃)₂, CH(CH₃)CH₂CH₃, CH₂CH₂SCH₃, phenyl, and benzyl.

5. A compound of claim 1, wherein the compound is of formula Ib, or a stereoisomer or a pharmaceutically acceptable salt thereof:

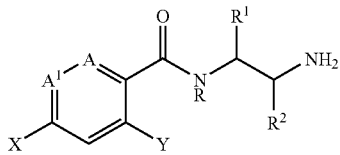

Ib wherein:
A is N;
A¹ is CH;
R, at each occurrence, is independently selected from H and $C_{1-4}$ alkyl;
R¹ is selected from H and $C_{1-4}$ alkyl;
R² is selected from H and $C_{1-4}$ alkyl;
X is selected from SO₂OR³, PO(OR³)₂, (CH₂)ₘCO₂R, NR(CH₂)ₙCO₂R, O(CH₂)ₙ-biphenyl-(CH₂)ₘCO₂R, NR(CH₂)ₙ-biphenyl-(CH₂)ₘCO₂R, O(CH₂)ₙ-aryl(CH₂)ₘCO₂R, O(CH₂)ₙ-aryl-$C_{2-6}$ alkenyl-CO₂R, O(CH₂)ₙ-aryl(CH₂)ₘ—PO(OR)₂, O(CH₂)ₙ-aryl-O(CH₂)ₙCO₂R, O(CH₂)ₙ-aryl-O-$C_{2-6}$ alkenyl-CO₂R, O(CH₂)ₙ-arylO(CH₂)ₙ—PO(OR)₂, O(CH₂)ₙ-aryl-NR(CH₂)ₙCO₂R, O(CH₂)ₙ-aryl-NR$C_{2-6}$ alkenyl-CO₂R, O(CH₂)ₙ-aryl-NR(CH₂)ₙ—PO(OR)₂, NR(CH₂)ₙ-aryl(CH₂)ₘCO₂R, NR(CH₂)ₙ-aryl-$C_{2-6}$ alkenyl-CO₂R, NR(CH₂)ₙ-aryl(CH₂)ₘ—PO(OR)₂, NR(CH₂)ₙ-aryl-NR(CH₂)ₙCO₂R, NR(CH₂)ₙ-aryl-NR—$C_{2-6}$ alkenyl-CO₂R, NR(CH₂)ₙ-aryl-NR(CH₂)ₙPO(OR)₂, NR(CH₂)ₙ-arylO(CH₂)ₙCO₂R, NR(CH₂)ₙ-aryl-O—$C_{2-6}$ alkenyl-CO₂R, NR(CH₂)ₙ-arylO(CH₂)ₙPO(OR)₂, O(CH₂)ₙ-heteroaryl(CH₂)ₘCO₂R, O(CH₂)ₙ-heteroaryl-$C_{2-6}$ alkenyl-CO₂R, O(CH₂)ₙ-heteroaryl(CH₂)ₘ—PO(OR)₂, O(CH₂)ₙ-heteroaryl-O(CH₂)ₙCO₂R, O(CH₂)ₙ-heteroaryl-O—$C_{2-6}$ alkenyl-CO₂R, O(CH₂)ₙ-heteroarylO(CH₂)ₙ—PO(OR)₂, O(CH₂)ₙ-heteroaryl-NR(CH₂)ₙCO₂R, O(CH₂)ₙ-heteroaryl-NR—$C_{2-6}$ alkenyl-CO₂R, O(CH₂)ₙ-heteroaryl-NR(CH₂)ₙ—PO(OR)₂, NR(CH₂)ₙ-heteroaryl(CH₂)ₘCO₂R, NR(CH₂)ₙ-heteroaryl-$C_{2-6}$ alkenyl-CO₂R, NR(CH₂)ₙ-heteroaryl(CH₂)ₘ—PO(OR)₂, NR(CH₂)ₙ-heteroaryl(CH₂)ₙCO₂R, NR(CH₂)ₙ-heteroaryl-NR—$C_{2-6}$ alkenyl-CO₂R, NR(CH₂)ₙ-heteroaryl-NR(CH₂)ₙPO(OR)₂, NR(CH₂)ₙ-heteroaryl-O(CH₂)ₙCO₂R, NR(CH₂)ₙ-heteroaryl-O—$C_{2-6}$ alkenyl-CO₂R, NR(CH₂)ₙ-heteroarylO(CH₂)ₙPO(OR)₂, and O(CH₂CH₂O)ₚCH₂CH₂OR³, where heteroaryl is a 5-12 membered ring system consisting of carbon atoms and from 1-4 heteroatoms selected from N, O, and S, and wherein aryl, heteroaryl, and biphenyl are substituted with 1-2 X²;

X², at each occurrence, is independently selected from H, OR, $C_{1-4}$ alkyl, $C_{2-4}$ alkenyl, $C_{2-4}$ alkynyl, halogen, $CF_3$, nitro, —CN, CON(R)₂, and SO₂N(R)$C_{1-4}$alkyl;

Y is selected from H, OW, NR³Z, OZ, SZ, SO₂NR³R⁴, CONR³R⁴, $CF_3$, CON(R)₂, SO₂N(R)$C_{1-4}$alkyl and NHSO₂R;

Z is selected from (CH₂)ₙCONR³R⁴, CH₂CH=CHCON(R³)₂, and (CH₂)ₙN±(R³)₃G⁻;

G⁻ is selected from Cl⁻ and Br⁻;

R³, at each occurrence, is independently selected from H, $C_{1-4}$ alkyl, $C_{2-4}$ alkenyl, and benzyl;

R⁴, at each occurrence, is independently selected from H, $C_{1-4}$ alkyl, phenyl, and CH(L)CO₂R³; and, L is selected from H, CH₃, CH₂CH₃, CH(CH₃)₂, CH₂CH(CH₃)₂, CH(CH₃)CH₂CH₃, CH₂CH₂SCH₃, phenyl, and benzyl.

6. A compound of claim 1, wherein the compound is of formula Ic, or a stereoisomer or a pharmaceutically acceptable salt thereof:

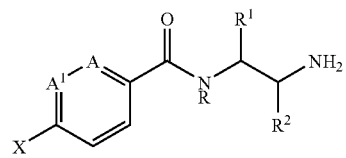

Ic wherein:
A is N;
A¹ is CH;
R, at each occurrence, is independently selected from H and $C_{1-4}$ alkyl;
R¹ is selected from H and $C_{1-4}$ alkyl;
R² is selected from H and $C_{1-4}$ alkyl;
X is selected from NR³Z, SZ, SO₂NR³R⁴, CONR³R⁴, (CH₂)ₘCONR₂, NR—$C_{2-4}$ alkenyl, NRSO₂CH₃, CH₂-aryl, O(CH₂)ₙ-biphenyl, O(CH₂)ₙ-biphenyl-(CH₂)ₘCN, O(CH₂)ₙ-biphenyl-(CH₂)ₘCON(R)₂, NR(CH₂)ₙ-biphenyl, NR(CH₂)ₙ-biphenyl-(CH₂)ₘCN, NR(CH₂)ₙ-biphenyl-(CH₂)ₘCON(R)₂, O(CH₂)ₙ-aryl, O(CH₂)ₙ-heteroaryl, NR(CH₂)ₙ-aryl, NR(CH₂)ₙ-heteroaryl, O(CH₂)ₙ-aryl(CH₂)ₘCN, O(CH₂)ₙ-aryl(CH₂)ₘCON(R)₂, O(CH₂)ₙ-arylO(CH₂)ₙCN, O(CH₂)ₙ-arylO(CH₂)ₙCON(R)₂, O(CH₂)ₙ-aryl-NR(CH₂)ₙCN, O(CH₂)ₙ-aryl-NR(CH₂)ₙCON(R)₂, NR(CH₂)ₙ-aryl(CH₂)ₘCN, NR(CH₂)ₙ-aryl(CH₂)ₘCON(R)₂, NR(CH₂)ₙ-aryl-NR(CH₂)ₙCN, NR(CH₂)ₙ-aryl-NR(CH₂)ₙCON(R)₂, NR(CH₂)ₙ-arylO(CH₂)ₙCN, NR(CH₂)ₙ-aryl-O(CH₂)ₙCON(R)₂, O(CH₂)ₙ-heteroaryl-(CH₂)ₘCN, O(CH₂)ₙ-heteroaryl(CH₂)ₘCON (R)$_2$, O(CH$_2$)$_n$-heteroaryl O(CH$_2$)$_n$CN, O(CH$_2$)$_n$-heteroarylO(CH$_2$)$_n$CON(R)$_2$, O(CH$_2$)$_n$-heteroaryl-NR(CH$_2$)$_n$CN, O(CH$_2$)$_n$-heteroaryl-NR(CH$_2$)$_n$CON(R)$_2$, NR(CH$_2$)$_n$-heteroaryl(CH$_2$)$_m$CN, NR(CH$_2$)$_n$-heteroaryl(CH$_2$)$_m$CON(R)$_2$, NR(CH$_2$)$_n$ heteroaryl-NR(CH$_2$)$_n$CN, NR(CH$_2$)$_n$-heteroaryl-NR(CH$_2$)$_n$CON(R)$_2$, NR(CH$_2$)$_n$-heteroaryl-O(CH$_2$)$_n$CN, NR(CH$_2$)$_n$-heteroaryl-O(CH$_2$)$_n$CON(R)$_2$, and O(CH$_2$CH$_2$O)$_p$CH$_2$CH$_2$OR$^3$, where heteroaryl is a 5-12 membered ring system consisting of carbon atoms and from 1-4 heteroatoms selected from N, O, and S, and wherein aryl, heteroaryl, and biphenyl are substituted with 1-2 X$^2$;

X$^2$, at each occurrence, is independently selected from H, OR, C$_{1-4}$ alkyl, C$_{2-4}$ alkenyl, C$_{2-4}$ alkynyl, halogen, CF$_3$, nitro, —CN, CON(R)$_2$, and SO$_2$N(R)C$_{1-4}$alkyl;

Z is (CH$_2$)$_n$N$^+$(R$^3$)$_3$G$^-$;

G$^-$ is selected from Cl$^-$ and Br$^-$;

R$^3$, at each occurrence, is independently selected from H, C$_{1-4}$ alkyl, and benzyl;

R$^4$, at each occurrence, is independently selected from H, C$_{1-4}$ alkyl, and CH(L)CO$_2$R$^3$; and, L is selected from H, CH$_3$, CH$_2$CH$_3$, CH(CH$_3$)$_2$, CH$_2$CH(CH$_3$)$_2$, CH(CH$_3$)CH$_2$CH$_3$, CH$_2$CH$_2$SCH$_3$, phenyl, and benzyl.

7. A compound of claim 1, wherein the compound is selected from Table IV, or a stereoisomer or pharmaceutically acceptable salt thereof:

TABLE IV

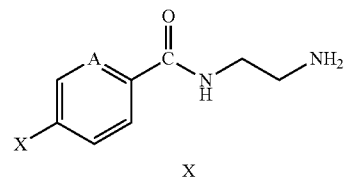

| Ex. # | X | Y | A | A$^1$ | A$^3$ |
|---|---|---|---|---|---|
| 1 | CO$_2$Et | H | N | CH | CH |
| 2 | CO$_2$H | H | N | CH | CH |
| 3 | SO$_3$Et | H | N | CH | CH |
| 4 | SO$_3$H | H | N | CH | CH |
| 5 | PO(OEt)$_2$ | H | N | CH | CH |
| 6 | PO(OH)$_2$ | H | N | CH | CH |
| 7 | NHCH$_2$CO$_2$Et | H | N | CH | CH |
| 8 | NHCH$_2$CO$_2$H | H | N | CH | CH |
| 9 | OCH$_2$CO$_2$Et | H | N | CH | CH |
| 10 | OCH$_2$CO$_2$H | H | N | CH | CH |
| 11 | NHCH$_2$CH$_2$CO$_2$Et | H | N | CH | CH |
| 12 | NHCH$_2$CH$_2$CO$_2$H | H | N | CH | CH |
| 13 | OCH$_2$CH$_2$CO$_2$Et | H | N | CH | CH |
| 14 | OCH$_2$CH$_2$CO$_2$H | H | N | CH | CH |
| 15 | NHCH$_2$CH=CHCO$_2$Et | H | N | CH | CH |
| 16 | NHCH$_2$CH=CHCO$_2$H | H | N | CH | CH |
| 17 | OCH$_2$CH=CHCO$_2$Et | H | N | CH | CH |
| 18 | OCH$_2$CH=CHCO$_2$H | H | N | CH | CH |
| 19 | OCH$_2$CH$_2$PO(OEt)$_2$ | H | N | CH | CH |
| 20 | OCH$_2$CH$_2$PO(OH)$_2$ | H | N | CH | CH |
| 21 | OCH$_2$CH$_2$N(CH$_3$)$_2$ | H | N | CH | CH |
| 22 | OCH$_2$CH$_2$N$^+$(CH$_3$)$_3$Cl$^-$ | H | N | CH | CH |
| 23 | SO$_2$NHEt | H | N | CH | CH |
| 24 | CONHCH(CH$_3$)CO$_2$Et | H | N | CH | CH |
| 25 | CONHCH(CH$_3$)CO$_2$H | H | N | CH | CH |
| 26 | CONHCH(CH$_2$C$_6$H$_5$)CO$_2$Et | H | N | CH | CH |
| 27 | CONHCH(CH$_2$C$_6$H$_5$)CO$_2$H | H | N | CH | CH |
| 28 | NHCH$_2$CONH$_2$ | H | N | CH | CH |
| 29 | NHCH$_2$CH$_2$CONH$_2$ | H | N | CH | CH |
| 30 | OCH$_2$CONH$_2$ | H | N | CH | CH |
| 31 | OCH$_2$CH$_2$CONH$_2$ | H | N | CH | CH. |

8. A compound of claim 1, wherein the compound is selected from Table XI, or a stereoisomer or pharmaceutically acceptable salt thereof:

TABLE XI

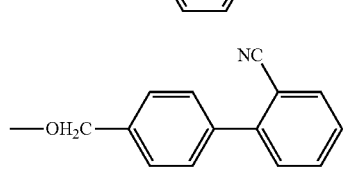

| Ex. # | X | A |
|---|---|---|
| 5 | OCH$_2$C$_6$H$_4$—F(3) | N |
| 6 | OCH$_2$C$_6$H$_4$—F(4) | N |
| 7 | OCH$_2$C$_6$H$_4$—CF$_3$(3) | N |
| 8 | OCH$_2$C$_6$H$_4$—CF$_3$(4) | N |
| 9 | OCH$_2$C$_6$H$_4$—NO$_2$(3) | N |
| 10 | OCH$_2$C$_6$H$_4$—NO$_2$(4) | N |
| 11 | OCH$_2$C$_6$H$_4$—NHSO$_2$CH$_3$(3) | N |
| 12 | OCH$_2$C$_6$H$_4$—NHSO$_2$CH$_3$(4) | N |
| 13 | OCH$_2$C$_6$H$_4$—CN(3) | N |
| 14 | OCH$_2$C$_6$H$_4$—CN(4) | N |
| 15 | OCH$_2$C$_6$H$_4$—CONH$_2$(3) | N |
| 16 | OCH$_2$C$_6$H$_4$—CONH$_2$(4) | N |
| 17 | OCH$_2$C$_6$H$_4$—OCH$_2$CN(3) | N |
| 18 | OCH$_2$C$_6$H$_4$—OCH$_2$CN(4) | N |
| 19 | OCH$_2$C$_6$H$_4$—OCH$_2$CONH$_2$(3) | N |
| 20 | OCH$_2$C$_6$H$_4$—OCH$_2$CONH$_2$(4) | N |
| 21 | OCH$_2$C$_6$H$_4$CH$_2$CN(3) | N |
| 22 | OCH$_2$C$_6$H$_4$CH$_2$CN(4) | N |
| 23 | OCH$_2$C$_6$H$_4$CH$_2$CONH$_2$(3) | N |
| 24 | OCH$_2$C$_6$H$_4$CH$_2$CONH$_2$(4) | N |
| 25 | OCH$_2$C$_6$H$_4$CO$_2$Et(3) | N |
| 26 | OCH$_2$C$_6$H$_4$CO$_2$H(3) | N |
| 27 | OCH$_2$C$_6$H$_4$CO$_2$Et(4) | N |
| 28 | OCH$_2$C$_6$H$_4$CO$_2$H(4) | N |
| 29 | OCH$_2$C$_6$H$_4$CH$_2$CO$_2$Et(3) | N |
| 30 | OCH$_2$C$_6$H$_4$CH$_2$CO$_2$H(3) | N |
| 31 | OCH$_2$C$_6$H$_4$CH$_2$CO$_2$Et(4) | N |
| 32 | OCH$_2$C$_6$H$_4$CH$_2$CO$_2$H(4) | N |
| 33 | OCH$_2$C$_6$H$_4$OCH$_2$CO$_2$Et(3) | N |
| 34 | OCH$_2$C$_6$H$_4$OCH$_2$CO$_2$H(3) | N |
| 35 | OCH$_2$C$_6$H$_4$OCH$_2$CO$_2$Et(4) | N |
| 36 | OCH$_2$C$_6$H$_4$OCH$_2$CO$_2$H(4) | N |
| 37 | OCH$_2$C$_6$H$_3$(CN)$_2$(3,5) | N |
| 38 | OCH$_2$C$_6$H$_3$(CN)$_2$(3,5) | N |
| 39 | OCH$_2$C$_6$H$_3$(CONH$_2$)$_2$(3,5) | N |
| 40 | OCH$_2$C$_6$H$_3$(CONH$_2$)$_2$(3,5) | N |
| 41 | OCH$_2$C$_6$H$_4$—OCH$_3$(3) | N |
| 42 | OCH$_2$C$_6$H$_4$—OCH$_3$(4) | N |
| 43 | 2'-CN-biphenyl-2-CH$_2$O— | N |
| 43' | 2'-CN-biphenyl-3-CH$_2$O— | N |
| 43" | 2'-CN-biphenyl-4-CH$_2$O— | N |

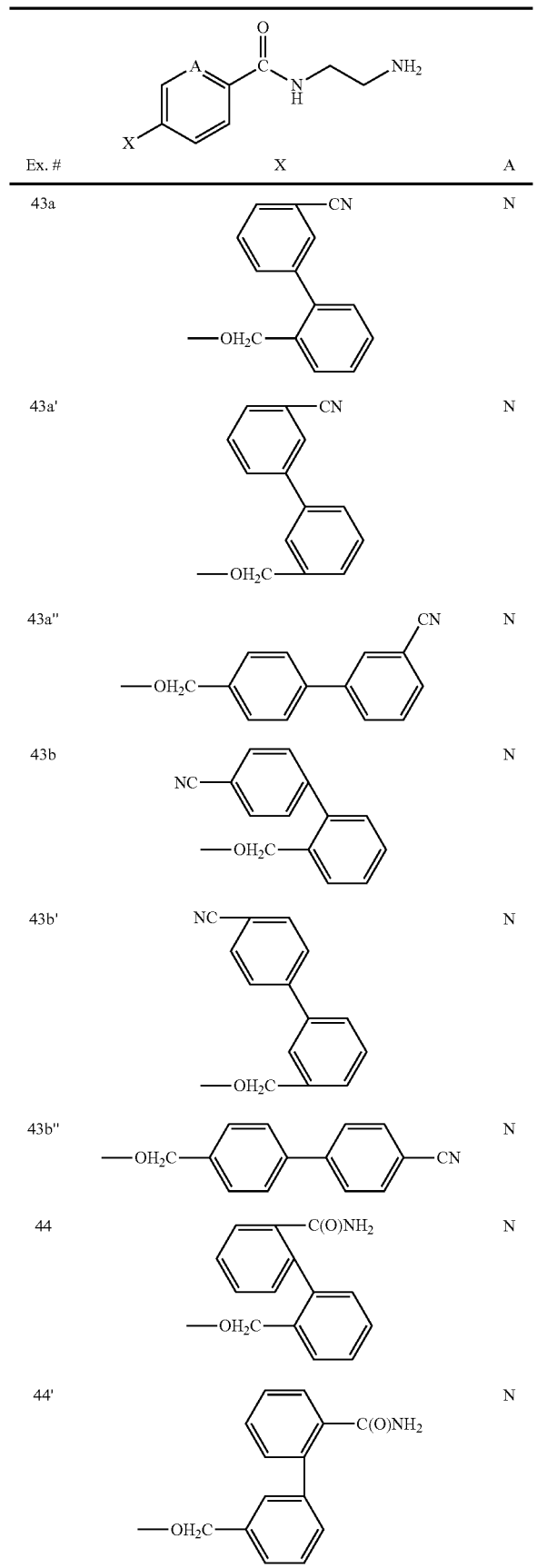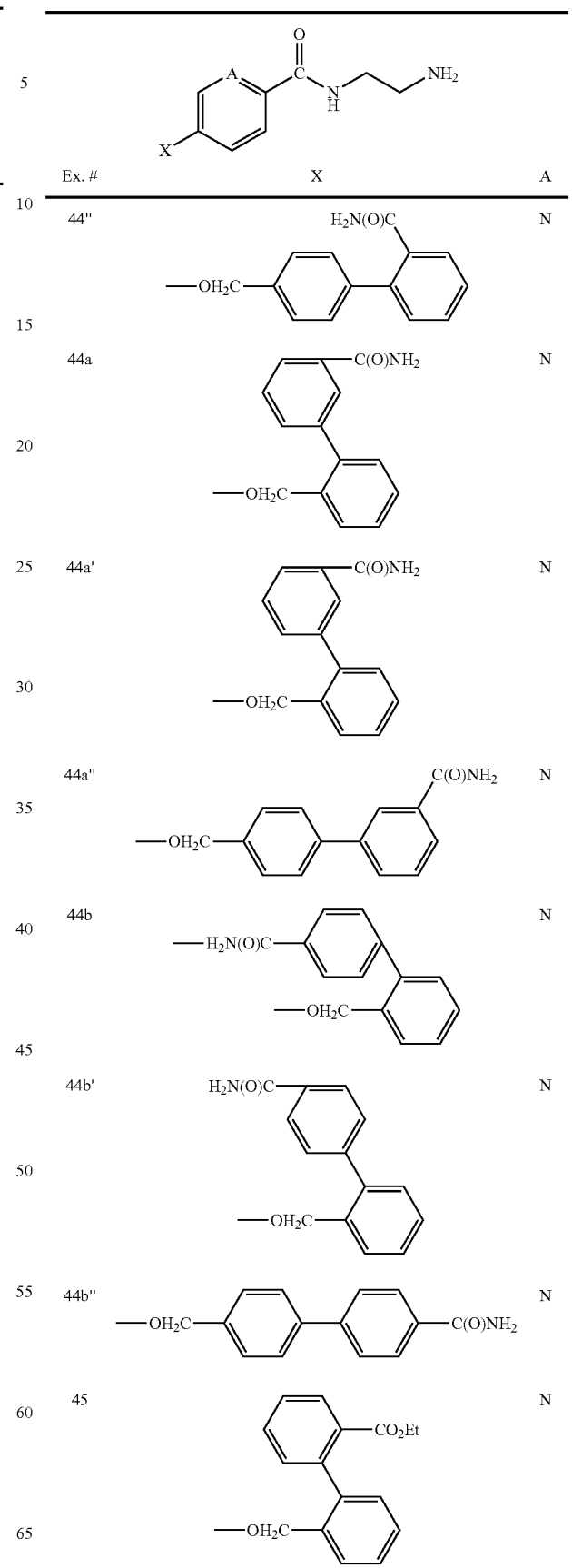

TABLE XI-continued

[Structure: benzamide with A in ring, X substituent, and N-(2-aminoethyl) group]

| Ex. # | X | A |
|---|---|---|
| 45' | 2'-(CO₃Et)-biphenyl-3-ylmethyl (—OH₂C—) | N |
| 45'' | 2'-(EtO₂C)-biphenyl-4-ylmethyl (—OH₂C—) | N |
| 45a | 3'-(CO₂Et)-biphenyl-2-ylmethyl (—OH₂C—) | N |
| 45a' | 3'-(CO₂Et)-biphenyl-3-ylmethyl (—OH₂C—) | N |
| 45a'' | 3'-(CO₂H)-biphenyl-4-ylmethyl (—OH₂C—) | N |
| 45b | 4'-(EtO₂C)-biphenyl-2-ylmethyl (—OH₂C—) | N |
| 45b' | 4'-(EtO₂C)-biphenyl-3-ylmethyl (—OH₂C—) | N |
| 45b'' | 4'-(CO₂Et)-terphenyl-4-ylmethyl | N |
| 46 | 2'-(CO₂H)-biphenyl-2-ylmethyl (—OH₂C—) | N |
| 46' | 2'-(CO₂H)-biphenyl-3-ylmethyl (—OH₂C—) | N |
| 46'' | 2'-(HO₂C)-biphenyl-4-ylmethyl (—OH₂C—) | N |
| 46a | 3'-(CO₂H)-biphenyl-2-ylmethyl (—OH₂C—) | N |
| 46a' | 3'-(CO₂H)-biphenyl-3-ylmethyl (—OH₂C—) | N |
| 46a'' | 3'-(CO₂H)-biphenyl-4-ylmethyl (—OH₂C—) | N |
| 46b | 4'-(HO₂C)-biphenyl-2-ylmethyl (—OH₂C—) | N |

TABLE XI-continued

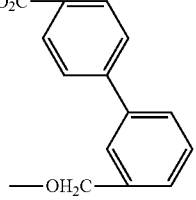

| Ex. # | X | A |
|---|---|---|
| 46b' | 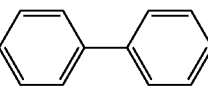 HO$_2$C-biphenyl-OH$_2$C- | N |
| 46b" | -OH$_2$C-biphenyl-CO$_2$H | N |
| 47 | OCH$_2$C$_6$H$_4$—CH$_3$(3) | N |
| 48 | OCH$_2$C$_6$H$_4$—CH$_3$(4) | N | wherein the number or numbers in the parentheses indicate the point of attachment of the substituent on the C$_6$H$_4$ or the C$_6$H$_3$ ring.

9. A compound of claim 1, wherein the compound is selected from Table XIII, or a stereoisomer or pharmaceutically acceptable salt thereof:

TABLE XIII

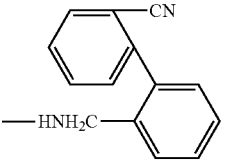

| Ex. # | X | A |
|---|---|---|
| 1 | NHCH$_2$CH$_2$C$_6$H$_5$ | N |
| 2 | NHCH$_2$C$_6$H$_5$ | N |
| 3 | NHCH$_2$C$_6$H$_4$—Cl(3) | N |
| 4 | NHCH$_2$C$_6$H$_4$—Cl(4) | N |
| 5 | NHCH$_2$C$_6$H$_4$—F(3) | N |
| 6 | NHCH$_2$C$_6$H$_4$—F(4) | N |
| 7 | NHCH$_2$C$_6$H$_4$—CF$_3$(3) | N |
| 8 | NHCH$_2$C$_6$H$_4$—CF$_3$(4) | N |
| 9 | NHCH$_2$C$_6$H$_4$—NO$_2$(3) | N |
| 10 | NHCH$_2$C$_6$H$_4$—NO$_2$(4) | N |
| 11 | NHCH$_2$C$_6$H$_4$—NHSO$_2$CH$_3$(3) | N |
| 12 | NHCH$_2$C$_6$H$_4$—NHSO$_2$CH$_3$(4) | N |
| 13 | NHCH$_2$C$_6$H$_4$—CN(3) | N |
| 14 | NHCH$_2$C$_6$H$_4$—CN(4) | N |
| 15 | NHCH$_2$C$_6$H$_4$—CONH$_2$(3) | N |
| 16 | NHCH$_2$C$_6$H$_4$—CONH$_2$(4) | N |
| 17 | NHCH$_2$C$_6$H$_4$—OCH$_2$CN(3) | N |
| 18 | NHCH$_2$C$_6$H$_4$—OCH$_2$CN(4) | N |
| 19 | NHCH$_2$C$_6$H$_4$—OCH$_2$CONH$_2$(3) | N |
| 20 | NHCH$_2$C$_6$H$_4$—OCH$_2$CONH$_2$(4) | N |
| 21 | NHCH$_2$C$_6$H$_4$CH$_2$CN(3) | N |
| 22 | NHCH$_2$C$_6$H$_4$CH$_2$CN(4) | N |
| 23 | NHCH$_2$C$_6$H$_4$CH$_2$CONH$_2$(3) | N |
| 24 | NHCH$_2$C$_6$H$_4$CH$_2$CONH$_2$(4) | N |
| 25 | NHCH$_2$C$_6$H$_4$CO$_2$Et(3) | N |
| 26 | NHCH$_2$C$_6$H$_4$CO$_2$H(3) | N |
| 27 | NHCH$_2$C$_6$H$_4$CO$_2$Et(4) | N |
| 28 | NHCH$_2$C$_6$H$_4$CO$_2$H(4) | N |
| 29 | NHCH$_2$C$_6$H$_4$CH$_2$CO$_2$Et(3) | N |
| 30 | NHCH$_2$C$_6$H$_4$CH$_2$CO$_2$H(3) | N |
| 31 | NHCH$_2$C$_6$H$_4$CH$_2$CO$_2$Et(4) | N |

TABLE XIII-continued

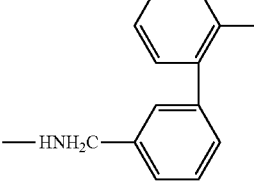

| Ex. # | X | A |
|---|---|---|
| 32 | NHCH$_2$C$_6$H$_4$CH$_2$CO$_2$H(4) | N |
| 33 | NHCH$_2$C$_6$H$_4$OCH$_2$CO$_2$Et(3) | N |
| 34 | NHCH$_2$C$_6$H$_4$OCH$_2$CO$_2$H(3) | N |
| 35 | NHCH$_2$C$_6$H$_4$OCH$_2$CO$_2$Et(4) | N |
| 36 | NHCH$_2$C$_6$H$_4$OCH$_2$CO$_2$H(4) | N |
| 37 | NHCH$_2$C$_6$H$_3$(CN)$_2$(3,5) | N |
| 38 | NHCH$_2$C$_6$H$_3$(CN)$_2$(3,5) | N |
| 39 | NHCH$_2$C$_6$H$_3$(CONH$_2$)$_2$(3,5) | N |
| 40 | NHCH$_2$C$_6$H$_3$(CONH$_2$)$_2$(3,5) | N |
| 41 | NHCH$_2$C$_6$H$_4$—OCH$_3$(3) | N |
| 42 | NHCH$_2$C$_6$H$_4$—OCH$_3$(4) | N |
| 43 | 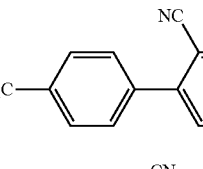 | N |
| 43' | 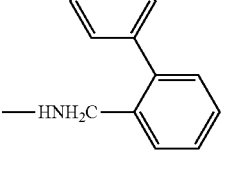 | N |
| 43" | 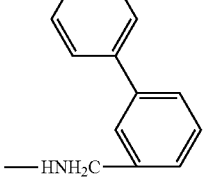 | N |
| 43a | 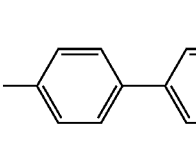 | N |
| 43a' |  | N |
| 43a" | -HNH$_2$C-biphenyl-CN | N |

TABLE XIII-continued

Structure: X—[benzene ring with A]—C(=O)—NH—CH₂CH₂—NH₂

| Ex. # | X | A |
|---|---|---|
| 43b | 4'-CN-biphenyl-2-yl-CH₂NH— | N |
| 43b' | 4'-CN-biphenyl-3-yl-CH₂NH— | N |
| 43b" | —HNH₂C—biphenyl—CN (4,4') | N |
| 44 | 2'-C(O)NH₂-biphenyl-2-yl-CH₂NH— | N |
| 44' | 2'-C(O)NH₂-biphenyl-3-yl-CH₂NH— | N |
| 44" | 2'-C(O)NH₂-biphenyl-4-yl-CH₂NH— | N |
| 44a | 3'-C(O)NH₂-biphenyl-2-yl-CH₂NH— | N |
| 44a' | 3'-C(O)NH₂-biphenyl-3-yl-CH₂NH— | N |
| 44a" | 3'-C(O)NH₂-biphenyl-4-yl-CH₂NH— | N |
| 44b | 4'-C(O)NH₂-biphenyl-2-yl-CH₂NH— | N |
| 44b' | 4'-C(O)NH₂-biphenyl-3-yl-CH₂NH— | N |
| 44b" | —HNH₂C—biphenyl—C(O)NH₂ (4,4') | N |
| 45 | 2'-CO₂Et-biphenyl-2-yl-CH₂NH— | N |
| 45' | 2'-CO₂Et-biphenyl-3-yl-CH₂NH— | N |
| 45" | 2'-CO₂Et-biphenyl-4-yl-CH₂NH— | N |
| 45a | 3'-CO₂Et-biphenyl-2-yl-CH₂NH— | N |

TABLE XIII-continued

[Structure: X-C₆H₃(A)-C(=O)-NH-CH₂CH₂-NH₂]

| Ex. # | X | A |
|---|---|---|
| 45a' | biphenyl with CO₂Et (3'-position) and HNH₂C- (4-position) | N |
| 45a" | biphenyl with CO₂H (3'-position) and —HNH₂C (4-position) | N |
| 45b | biphenyl with EtO₂C- (4'-position) and —HNH₂C (2-position) | N |
| 45b' | biphenyl with EtO₂C- (3'-position) and —HNH₂C (2-position) | N |
| 45b" | biphenyl with —HNH₂C (4-position) and —CO₂Et (4'-position) | N |
| 46 | biphenyl with CO₂H (2'-position) and —HNH₂C (2-position) | N |
| 46' | biphenyl with CO₂H (2'-position) and —HNH₂C (3-position) | N |
| 46" | biphenyl with HO₂C (2'-position) and —HNH₂C (4-position) | N |

TABLE XIII-continued

[Structure: X-C₆H₃(A)-C(=O)-NH-CH₂CH₂-NH₂]

| Ex. # | X | A |
|---|---|---|
| 46a | biphenyl with CO₂H (3'-position) and —HNH₂C (2-position) | N |
| 46a' | biphenyl with CO₂H (3'-position) and —HNH₂C (3-position) | N |
| 46a" | biphenyl with CO₂H (3'-position) and —OH₂C (4-position) | N |
| 46b | biphenyl with HO₂C (4'-position) and —HNH₂C (2-position) | N |
| 46b' | biphenyl with HO₂C (4'-position) and —HNH₂C (3-position) | N |
| 46b" | biphenyl with —HNH₂C (4-position) and —CO₂H (4'-position) | N |
| 47 | NHCH₂C₆H₄—CH₃(3) | N |
| 48 | NHCH₂C₆H₄—CH₃(4) | N | wherein the number or numbers in the parentheses indicate the point of attachment of the substituent on the C₆H₄ or the C₆H₃ ring.

10. A compound of claim 1, wherein the compound is selected from Table XIV, or a stereoisomer or pharmaceutically acceptable salt thereof:

TABLE XIV

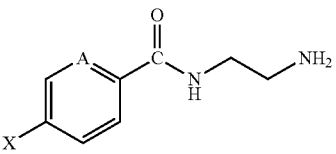

| Ex # | X | A |
|---|---|---|
| 1. | O(CH$_2$CH$_2$O)$_2$CH$_2$CH$_2$OH | N |
| 2. | O(CH$_2$CH$_2$O)$_2$CH$_2$CH$_2$OCH$_3$ | N |
| 3. | O(CH$_2$CH$_2$O)$_3$CH$_2$CH$_2$OH | N |
| 4. | O(CH$_2$CH$_2$O)$_3$CH$_2$CH$_2$OCH$_3$ | N |
| 5. | O(CH$_2$CH$_2$O)$_4$CH$_2$CH$_2$OH | N |
| 6. | O(CH$_2$CH$_2$O)$_4$CH$_2$CH$_2$OCH$_3$ | N |
| 7. | O(CH$_2$CH$_2$O)$_5$CH$_2$CH$_2$OH | N |
| 8. | O(CH$_2$CH$_2$O)$_5$CH$_2$CH$_2$OCH$_3$ | N |
| 9. | O(CH$_2$CH$_2$O)$_7$CH$_2$CH$_2$OH | N |
| 10. | O(CH$_2$CH$_2$O)$_7$CH$_2$CH$_2$OCH$_3$ | N |
| 11. | O(CH$_2$CH$_2$O)$_9$CH$_2$CH$_2$OH | N |
| 12. | O(CH$_2$CH$_2$O)$_9$CH$_2$CH$_2$OCH$_3$ | N |
| 13. | O(CH$_2$CH$_2$O)$_{11}$CH$_2$CH$_2$OCH$_3$ | N |

11. A pharmaceutical composition, comprising: a therapeutically effective amount of a compound of claim 1 and a pharmaceutically acceptable carrier.

12. A pharmaceutical composition, comprising: a therapeutically effective amount of a compound of claim 2 and a pharmaceutically acceptable carrier.

13. A pharmaceutical composition, comprising: a therapeutically effective amount of a compound of claim 3 and a pharmaceutically acceptable carrier.

14. A pharmaceutical composition, comprising: a therapeutically effective amount of a compound of claim 4 and a pharmaceutically acceptable carrier.

15. A pharmaceutical composition, comprising: a therapeutically effective amount of a compound of claim 5 and a pharmaceutically acceptable carrier.

16. A pharmaceutical composition, comprising: a therapeutically effective amount of a compound of claim 6 and a pharmaceutically acceptable carrier.

17. A pharmaceutical composition, comprising: a therapeutically effective amount of a compound of claim 6 and a pharmaceutically acceptable carrier.

18. A pharmaceutical composition, comprising: a therapeutically effective amount of a compound of claim 8 and a pharmaceutically acceptable carrier.

19. A pharmaceutical composition, comprising: a therapeutically effective amount of a compound of claim 9 and a pharmaceutically acceptable carrier.

20. A pharmaceutical composition, comprising: a therapeutically effective amount of a compound of claim 10 and a pharmaceutically acceptable carrier.

\* \* \* \* \*